(12) United States Patent
Reznik et al.

(10) Patent No.: US 9,827,283 B2
(45) Date of Patent: *Nov. 28, 2017

(54) XANTHOPHYLL COMPOSITIONS AND METHODS OF USE

(71) Applicant: Novus International Inc., St. Charles, MO (US)

(72) Inventors: Gary Reznik, St. Charles, MO (US); Joan Carles Ferrater Martorell, Reus (ES); David Ribera, Reus (ES); Antonio Viso, Reus (ES); Juan Antonio Fernandez, Reus (ES); Delfin Ferrus, Reus (ES); Scott Hine, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/860,324

(22) Filed: Sep. 21, 2015

(65) Prior Publication Data

US 2016/0074456 A1    Mar. 17, 2016

Related U.S. Application Data

(63) Continuation of application No. 14/106,012, filed on Dec. 13, 2013, now Pat. No. 9,271,935.

(Continued)

(51) Int. Cl.
| | |
|---|---|
| *A61K 9/14* | (2006.01) |
| *A61K 36/28* | (2006.01) |
| *A61K 31/047* | (2006.01) |
| *C11C 1/02* | (2006.01) |
| *C09F 1/04* | (2006.01) |
| *A23K 20/179* | (2016.01) |

(Continued)

(52) U.S. Cl.
CPC ............ *A61K 36/28* (2013.01); *A23K 20/179* (2016.05); *A23K 50/75* (2016.05); *A23K 50/80* (2016.05); *A61K 9/14* (2013.01); *A61K 31/047* (2013.01); *C09F 1/04* (2013.01); *C11C 1/025* (2013.01); *A61K 47/46* (2013.01)

(58) Field of Classification Search
None
See application file for complete search history.

(56) References Cited

U.S. PATENT DOCUMENTS

| | | |
|---|---|---|
| 2,906,760 A | 9/1959 | Palmquist et al. |
| 3,523,138 A | 8/1970 | Grant |

(Continued)

FOREIGN PATENT DOCUMENTS

| | | | | |
|---|---|---|---|---|
| CN | 1610662 A | * | 4/2005 | ........... C07C 403/24 |
| CN | 101433528 A | | 5/2009 | |

(Continued)

OTHER PUBLICATIONS

Machine Translation of ES 2,265,787 A1 from Google Translate. Translation Obtained by Examiner on Sep. 7, 2016. Original Publiation Date in Spanish—Feb. 16, 2007. 19 printed pages.*

(Continued)

*Primary Examiner* — Isaac Shomer
(74) *Attorney, Agent, or Firm* — Polsinelli PC

(57) ABSTRACT

The present invention encompasses a carotenoid composition, a process for producing a carotenoid composition, and methods of use thereof.

23 Claims, 24 Drawing Sheets

Related U.S. Application Data

(60) Provisional application No. 61/739,074, filed on Dec. 19, 2012.

(51) Int. Cl.
  *A23K 50/75* (2016.01)
  *A23K 50/80* (2016.01)
  *A61K 47/46* (2006.01)

(56) References Cited

U.S. PATENT DOCUMENTS

| | | |
|---|---|---|
| 3,535,426 A | 10/1970 | Hawks |
| 3,997,679 A | 12/1976 | Salkin |
| 4,088,791 A * | 5/1978 | Jones ................. A23C 1/16 426/250 |
| 4,522,743 A * | 6/1985 | Horn ................. C07C 403/24 426/540 |
| 4,772,710 A | 9/1988 | von Magius |
| 5,079,016 A * | 1/1992 | Tood, Jr. ............. A23L 3/3472 426/250 |
| 5,382,714 A * | 1/1995 | Khachik ............. C07C 35/21 568/816 |
| 5,453,447 A | 9/1995 | End et al. |
| 5,523,494 A | 6/1996 | Torres-Cardona et al. |
| 5,648,564 A | 7/1997 | Ausich et al. |
| 5,811,609 A | 9/1998 | Vilstrup et al. |
| 5,854,015 A | 12/1998 | Garnett et al. |
| 5,863,953 A | 1/1999 | Luddecke et al. |
| 5,968,251 A | 10/1999 | Auweter et al. |
| 5,998,678 A | 12/1999 | Sanroma Virgili et al. |
| 6,262,284 B1 | 7/2001 | Khachik |
| 6,329,557 B1 | 12/2001 | Rodriguez et al. |
| 6,376,722 B1 | 4/2002 | Sanz et al. |
| 6,380,442 B1 | 4/2002 | Madhavi et al. |
| 6,504,067 B1 | 1/2003 | Montoya-Olvera et al. |
| 6,689,400 B2 | 2/2004 | Majeed |
| 6,743,953 B2 | 6/2004 | Sebastian et al. |
| 6,863,914 B1 | 3/2005 | Auweter et al. |
| 7,045,643 B2 | 5/2006 | Estrella De Castro et al. |
| 7,150,890 B2 | 12/2006 | Rosales et al. |
| 7,179,930 B2 | 2/2007 | Bhaskaran et al. |
| 7,271,298 B2 | 9/2007 | Xu et al. |
| 7,446,101 B1 | 11/2008 | Madhavi et al. |
| 7,527,820 B2 | 5/2009 | Allen et al. |
| 7,622,599 B2 | 11/2009 | Swaminathan et al. |
| 7,629,007 B2 | 12/2009 | Pena |
| 7,758,884 B2 | 7/2010 | Kaw et al. |
| 7,812,198 B2 | 10/2010 | Eidenberger |
| 7,875,751 B2 | 1/2011 | Chuang et al. |
| 7,943,804 B2 | 5/2011 | King et al. |
| 8,008,532 B2 | 8/2011 | Mehta |
| 8,034,983 B2 | 10/2011 | Du et al. |
| 8,192,773 B2 | 6/2012 | Leow et al. |
| 9,271,935 B2 * | 3/2016 | Reznik ................. A61K 9/14 |
| 2003/0232892 A1 | 12/2003 | Guerra-santos et al. |
| 2004/0044085 A1 | 3/2004 | Kumar et al. |
| 2004/0126338 A1 | 7/2004 | Ausich et al. |
| 2004/0131748 A1 | 7/2004 | Allen et al. |
| 2005/0079223 A1 | 4/2005 | Estrella De Castro et al. |
| 2005/0139145 A1 | 6/2005 | Quesnel et al. |
| 2005/0182280 A1 | 8/2005 | Bhaskaran et al. |
| 2007/0032683 A1 | 2/2007 | Xu et al. |
| 2007/0098820 A1 | 5/2007 | Bortlik et al. |
| 2007/0148193 A1 | 6/2007 | Behnam |
| 2008/0051591 A1 | 2/2008 | Swaminathan et al. |
| 2008/0181960 A1 | 7/2008 | Doney |
| 2010/0081850 A1 | 4/2010 | Swaminathan et al. |
| 2010/0121112 A1 | 5/2010 | Chuang et al. |
| 2010/0137646 A1 | 6/2010 | Du |
| 2010/0240933 A1 | 9/2010 | King et al. |
| 2010/0267838 A1 | 10/2010 | Kopsel |
| 2010/0305366 A1 | 12/2010 | Liu et al. |
| 2011/0027418 A1 | 2/2011 | Horgan et al. |
| 2011/0065805 A1 | 3/2011 | Kumar et al. |
| 2011/0282083 A1 | 11/2011 | Reilly et al. |
| 2012/0107380 A1 * | 5/2012 | Tuinstra ................. A61K 8/345 424/401 |

FOREIGN PATENT DOCUMENTS

| | | | |
|---|---|---|---|
| CN | 102481011 A * | 5/2012 | ........... A61K 31/047 |
| EP | 1371641 A1 | 12/2003 | |
| EP | 1716210 A1 | 11/2006 | |
| EP | 1968396 A2 | 9/2008 | |
| ES | 2265787 A1 * | 2/2007 | |
| ES | 2281276 A1 | 9/2007 | |
| ES | 2281277 A1 | 9/2007 | |
| ES | 2327888 A1 | 11/2009 | |
| WO | 2012099571 A1 | 7/2012 | |

OTHER PUBLICATIONS

English Translation of Chinese Patent document CN 102481011 A. Translation Obtained by Examiner on Jul. 13, 2017. Document originally published in Chinese on May 30, 2012. 11 printed pages.*
English Translation of Chinese Patent document CN 1610662 A. Translation Obtained by Examiner on Jul. 13, 2017. Document originally published in Chinese on Apr. 27, 2005. 5 printed pages.*
Office Action from related Colombian Patent Application No. 15 159523, dated Aug. 11, 2015.
Office Action from related Australian Patent Application No. 2013363208, dated Sep. 24, 2015.
Morales, et al., "Fecundity compromises attractiveness when pigments are scarce," Oxford Journals Behavioral Ecology, vol. 20, Issue 1, 2008, pp. 117-123.
ISA Brown, Commercial Management Guide, 2009-2010, pp. 1-40.
Extended European Search Report for related application No. EP 13865831, 11 pages.
Examination report dated Oct. 10, 2016 for related application No. AU 2016203807, 5 pages.
Examination report dated Jun. 27, 2016 for related application No. CN 201380073294, 39 pages.
European search report dated May 4, 2016 for related application No. EP 13865831, 11 pages.
Notice of Allowance for related application No. TW 102146982, 12 pages.
Office Action dated Jan. 17, 2017 for related U.S. Appl. No. 14/860,328, 16 pages.
Office Action from related Colombian Patent Application No. 15 159523, dated Dec. 5, 2016, 15 pages.
Office Action from related Chinese Patent Application No. 201380073294.4, dated Mar. 15, 2017, 36 pages.
Office Action from related Australian Patent Application No. 2016203807, dated Mar. 22, 2017, 3 pages.

* cited by examiner

XANTHOPHYLL COMPOSITIONS AND METHODS OF USE

CROSS-REFERENCE TO RELATED APPLICATIONS

This application is a continuation of U.S. Ser. No. 14/106,012, filed Dec. 13, 2013 which claims priority to U.S. Ser. No. 61/739,074, filed Dec. 19, 2012, each of which is hereby incorporated by reference in its entirety.

FIELD OF THE INVENTION

The present invention encompasses a carotenoid composition, a process for producing a carotenoid composition, and methods of use thereof.

BACKGROUND OF THE INVENTION

Carotenoids, including lutein and other xanthophylls, are natural compounds used in pigmenting compositions. They may be found in extracts of several different plants, including marigold and paprika plants. These plant extracts, referred to as oleoresins, are processed into formulations of carotenoids that may be used in a variety of industries.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A shows X-40; FIG. 2B shows XCT.

FIG. 3A shows X-40; FIG. 3B shows XCT.

FIG. 5A shows melting at 40° C.; FIG. 5B shows melting at 80° C.; FIG. 5C shows melting at 150° C.; and FIG. 5D shows melting at 200° C.

FIG. 15A shows the FTIR spectra for X-40 and XCT. FIG. 15B shows an expansion of the region from 1800 to 600 $cm^{-1}$. FIG. 15C shows Raman spectra of X-40 and XCT.

SUMMARY OF THE INVENTION

Figure 1:
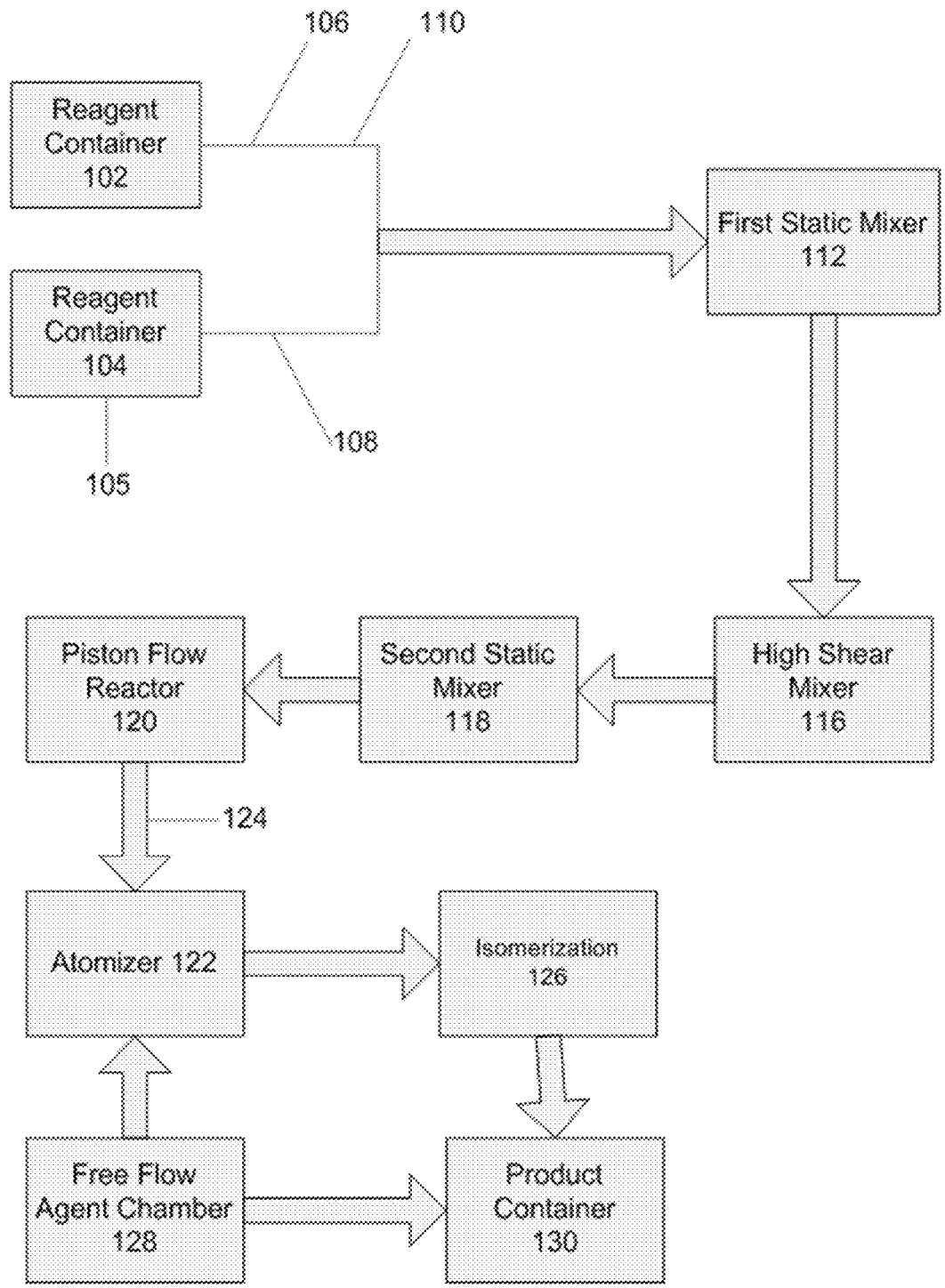
FIG. 1 shows a schematic of a continuous flow apparatus described herein.

In some aspects, the present disclosure provides a composition, the composition comprising soap derived from the saponification of a natural carotenoid-containing oleoresin, wherein the soap contains non-esterified xanthophyll particles, and retains greater than 80% total xanthophyll concentration when stored at room temperature, in an oxygen permeable dark bag, for three months.

In another aspect, the present disclosure provides a composition comprising soap derived from the saponification of a natural carotenoid-containing oleoresin, wherein the soap contains non-esterified xanthophyll particles, and 90% of the non-esterified xanthophyll particles are less than 0.5 microns across the largest diameter.

In still another aspect, a method for creating a final product with a non-esterified carotenoid composition of greater than 10% is provided. The process comprises (a) alkaline saponification of a natural carotenoid-containing oleoresin, wherein the saponification occurs in the presence of a metal hydroxide, with intimate mixing, and occurs at a temperature between about 110° C. to about 180° C., resulting in a composition comprising non-esterified carotenoids, (b) atomization of the resulting soap comprising non-esterified carotenoids to produce an atomized soap, and (c) isomerization of the non-esterified carotenoids, wherein the atomized soap is heated such that greater than 80% of the non-esterified carotenoids present are in the all-trans isomer configuration, and the non-esterified carotenoid concentration of the final soap product is greater than 10%.

In still another alternative aspect, a process for creating an aqueous product from water and a final product with a non-esterified carotenoid concentration of greater than 10% is provided. The process comprises (a) alkaline saponification of a natural carotenoid-containing oleoresin, wherein the saponification occurs in the presence of a metal hydroxide, with intimate mixing, and occurs at a temperature between about 110° C. to about 180° C., resulting in a soap comprising non-esterified carotenoids, (b) isomerization of the non-esterified carotenoids, wherein the soap is heated such that greater than 80% of the non-esterified carotenoids present are in the all-trans isomer configuration, to produce a non-esterified carotenoid concentration of the final soap product is greater than 10%, and (c) contacting the final soap product with water in sufficient amounts to create an aqueous product having from 5% to about 25% of the final soap product.

Other aspects and features of the present disclosure are provided herein.

DETAILED DESCRIPTION OF THE INVENTION

The present invention encompasses a carotenoid composition, a process of producing the carotenoid formulation, and methods of using the carotenoid composition. Advantageously, a carotenoid composition of the invention has improved bioavailability and increased coloring efficiency compared to carotenoid compositions produced by other means.

I. Composition

One aspect of the present invention encompasses a composition comprising a soap derived from the saponification of a natural carotenoid-containing oleoresin. Such a soap contains non-esterified xanthophyll particles. A soap of the invention also comprises the remaining components of the original natural carotenoid-containing oleoresin.

A composition of the invention may either be liquid or a solid, e.g. granules or a powder. Generally speaking the moisture content of a solid composition of the invention is below 10%. In some embodiments, the moisture content is below 10, 9, 8, 7, 6, 5, 4, 3, 2, or 1%. In exemplary embodiments, the moisture content is below 3%. In further exemplary embodiments, the moisture content is below 2%.

(a) Natural Carotenoid-Containing Oleoresin

A composition of the invention comprises a soap derived from the saponification of a natural carotenoid-containing oleoresin. The term "oleoresin," as used herein, refers to a composition comprising a plant extract. The phrase "carotenoid-containing oleoresin" refers to an oleoresin that contains one or more carotenoids, which are organic pigments. Finally, as used herein, the phrase "natural carotenoid-containing oleoresin" refers to a carotenoid-containing oleoresin derived from a plant.

Suitable examples of natural carotenoid-containing oleoresins are known in the art. For instance, a natural carotenoid-containing oleoresin may be a marigold oleoresin, or may be a paprika oleoresin, or a combination thereof. In one embodiment the natural carotenoid-containing oleoresin is a marigold oleoresin. For instance, the marigold oleoresin may be a *Tagetes erecta, Tagetes patula, Tagetes tenuifolia, Tagetes pumila* or a *Tagetes hybrid* oleoresin. In another embodiment, the natural carotenoid-containing oleoresin is a paprika oleoresin. For instance, the paprika oleoresin may be a *Capsicum annum linn, Capsicum bacatum, Capsicum buforum* or *Capsicum frutescens* oleoresin. In other embodiments, the natural carotenoid-containing oleoresin is a combination of marigold and paprika oleoresin. For instance, a natural carotenoid-containing oleoresin may comprise a ratio of about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10 marigold oleoresin to paprika oleoresin.

Methods of preparing an oleoresin from a plant are known in the art. Alternatively, the oleoresin may be purchased.

(b) Non-Esterified Xanthophyll Particles

A composition of the invention comprises non-esterified xanthophyll particles. As used herein, the phrase "xanthophyll particles" refers to xanthophyll, regardless of whether the xanthophyll is crystalline or amorphous. Various ratios of crystalline xanthophyll to amorphous xanthophyll are envisioned, ranging from about 100% crystalline to about 100% amorphous. In one embodiment, a composition of the invention comprises both crystalline and amorphous xanthophyll. In another embodiment, a composition of the invention comprises at least about 10%, 20%, 30%, 40%, 50%, 60%, 70%, 80%, 90% crystalline xanthophyll. In yet another embodiment, a composition of the invention comprises at least about 10%, 20%, 30%, 40%, 50%, 60%, 70%, 80%, 90% amorphous xanthophyll.

The phrase "non-esterified" as used herein, refers to xanthophyll that has been hydrolyzed from a fatty acid ester. As detailed in Section III of this application, a xanthophyll may be hydrolyzed from a fatty acid ester via saponification of the natural carotenoid-containing oleoresin.

The term "xanthophyll" refers to a carotenoid that comprises at least one oxygen atom. Such a compound may also be referred to as a phylloxanthin. Suitable xanthophylls include those found in a natural carotenoid-containing oleoresin. For example, suitable xanthophylls may include lutein, zeaxanthin, neoxanthin, violaxanthin, α- and β-cryptoxanthin, capsanthin and capsorubin. In one embodiment, a composition of the invention comprises at least one type of xanthophyll. In another embodiment, a composition of the invention comprises at least two types of xanthophylls. In yet another embodiment, a composition of the invention comprises at least three types of xanthophylls. In an exemplary embodiment, a composition of the invention comprises lutein. In another exemplary embodiment, a composition of the invention comprises zeaxanthin. In a further exemplary embodiment, a composition of the invention comprises both lutein and zeaxanthin.

i. Size Across the Largest Diameter

Generally speaking, the size of the xanthophyll particles in a composition of the invention is small, e.g. less than 1 micron. This refers to the size of the largest diameter of the particle. This small size contributes to both increased bioavailability and increased stability, when compared to larger particle sizes.

In some embodiments, at least about 90, 91, 92, 93, 94, 95, 96, 97, 98, 99, or 100% of the non-esterified xanthophyll particles are less than 1.0 microns across the largest diameter. In other embodiments, at least about 90, 91, 92, 93, 94, 95, 96, 97, 98, 99, or 100% of the non-esterified xanthophyll particles are less than 0.9 microns across the largest diameter. In certain embodiments, at least about 90, 91, 92, 93, 94, 95, 96, 97, 98, 99, or 100% of the non-esterified xanthophyll particles are less than 0.8 microns across the largest diameter. In several embodiments, at least about 90, 91, 92, 93, 94, 95, 96, 97, 98, 99, or 100% of the non-esterified xanthophyll particles are less than 0.7 microns across the largest diameter. In select embodiments, at least about 80, 81, 82, 83, 84, 85, 86, 87, 88, 89, 90, 91, 92, 93, 94, 95, 96, 97, 98, 99, or 100% of the non-esterified xanthophyll particles are less than 0.6 microns across the largest diameter.

In one embodiment, at least about 75% of the non-esterified xanthophyll particles are less than 0.5 microns across the largest diameter. For instance, in some embodiments, at least about 75, 76, 77, 78, 79, 80, 81, 82, 83, 84, 85, 86, 87, 88, 89, or 90% of the non-esterified xanthophyll particles are less than 0.5 microns across the largest diameter. In other embodiments, at least about 91, 92, 93, 94, 95, 96, 97, 98, or 99% of the non-esterified xanthophyll particles are less than 0.5 microns across the largest diameter. In one embodiment, at least about 90% of the non-esterified xanthophyll particles are less than 0.5 microns across the largest diameter.

In an alternative embodiment, at least about 75% of the non-esterified xanthophyll particles are less than 0.4 microns across the largest diameter. For instance, in some embodiments, at least about 75, 76, 77, 78, 79, 80, 81, 82, 83, 84, 85, 86, 87, 88, 89, or 90% of the non-esterified xanthophyll particles are less than 0.4 microns across the largest diameter.

ii. Amount of Non-Esterified Xanthophyll Particles

Advantageously, a composition of the invention comprises a high concentration of non-esterified xanthophyll particles. For instance, in one embodiment, a composition of the invention comprises about 75 mg of non-esterified xanthophyll per gram of soap derived from the saponification of a natural carotenoid-containing oleoresin. In other embodiments, a composition of the invention comprises at least about 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, or 110 mg of non-esterified xanthophyll per gram of soap derived from the saponification of a natural carotenoid-containing oleoresin. In still other embodiments, a composition of the invention comprises about 100, 101, 102, 103, 104, 105, 106, 107, 108, 109, 110, 111, 112, 113, 114, 115, 116, 117, 118, 119 or 120 mg of non-esterified xanthophyll per gram of soap derived from the saponification of a natural carotenoid-containing oleoresin. In an exemplary embodiment, a composition of the invention comprises about 90 mg to about 110 mg of non-esterified xanthophyll per gram of soap derived from the saponification of a natural carotenoid-containing oleoresin. In a further exemplary embodiment, a composition of the invention comprises at least about 99 mg of non-esterified xanthophyll per gram of soap derived from the saponification of a natural carotenoid-containing oleoresin. In an embodiment where dioxin removal from the oleoresin is conducted, a composition of the invention comprises about 110, 111, 112, 113, 114, 115, 116, 117, 118, 119 or 120, 121, 122, 123, 124, 125, 126, 127, 128, 129, 130, 131, 132, 133, 134, 135, 136, 137, 138, 139, 140 mg of non-esterified xanthophyll per gram of soap derived from the saponification of a natural carotenoid-containing oleoresin.

In certain embodiments, a dry composition of the invention is at least 5, at least 6, at least 7, at least 8, at least 9, at least 10, at least 11, at least 12, at least 13, at least 14, at least 15% xanthophyll or higher. For instance, a dry composition of the invention may be at least about 8, 8.25, 8.5, 8.75, 9, 9.25, 9.5, 9.75, 10, 10.25, 10.5, 10.75, or 11% xanthophyll. In an exemplary embodiment, a dry composition of the invention is at least about 9.5% xanthophyll. In a further exemplary embodiment, a dry composition of the invention is at least about 10% xanthophyll. In another alternative embodiment, with dioxin removal from the oleoresin, the concentration of xanthophyll can go higher. In such aspects, the composition may be at least 9, 9.25, 9.5, 9.75, 10, 10.25, 10.5, 10.75, 11, 11.25, 11.5, 11.75, 12, 12.25, 12.5, 12.75, 13, 13.25, 13.5, 13.75, 14, 14.25, 14.5, 14.75, 15, 15.25, 15.5, 15.75, 16% or higher.

In other embodiments, a liquid composition of the invention is at least 0.5, at least 1, at least 2, or at least 3% xanthophyll. For instance, a liquid composition of the invention may be at least about 0.5, 0.75, 1.0, 1.25, 1.5, 1.75, 2.0, 2.25, 2.5, 2.75, or 3.0% xanthophyll. In an exemplary embodiment, a liquid composition of the invention is at least about 1% xanthophyll. In a further exemplary embodiment, a liquid composition of the invention comprises between about 1% and about 3% xanthophyll.

iii. Isomerism

As is known in the art, xanthophylls may exist as different isomers. In particular, they may exist as cis isomers, or all trans isomers. Methods of determining the amount of a cis isomer, or the amount of all trans isomer, in a composition are also known in the art. For instance, see the Examples included herewith. Generally speaking, a composition of the invention may comprise at least about 50% of the all trans isomer. In some embodiments, a composition of the invention may comprise at least about 50, 55, 60, 65, 70, 75, 80, 85, 90, 95, or 99% of the all trans isomer. In other embodiments, a composition of the invention may comprise at least about 75, 76, 77, 78, 79, 80, 81, 82, 83, 84, or 85% of the all trans isomer. In exemplary embodiments, a composition of the invention may comprise at least about 80% of the all trans isomer.

(c) Stability

The xanthophyll particles of a composition of the invention are remarkably stable. For instance, if a composition of the invention is stored at room temperature, in an oxygen permeable bag, at least about 80% of the initial xanthophyll concentration is present at one month. In one embodiment, at room temperature and in an oxygen permeable bag, at least about 80, 81, 82, 83, 84, 85, 86, 87, 88, 89, 90, 91, 92, 93, 94, 95, 96, 97, 98, 99, or 100% of the initial total xanthophyll concentration is present at one month. In an exemplary embodiment, at room temperature and in an oxygen permeable bag, at least about 98, 99, or 100% of the initial total xanthophyll concentration is present at one month.

In another embodiment, at room temperature and in an oxygen permeable bag, at least about 80, 81, 82, 83, 84, 85, 86, 87, 88, 89, 90, 91, 92, 93, 94, 95, 96, 97, 98, 99, or 100% of the initial total xanthophyll concentration is present at three months. In an exemplary embodiment, at room temperature and in an oxygen permeable bag, at least about 92, 93, 94, 95, 96, 97, 98, 99, or 100% of the initial total xanthophyll concentration is present at three months.

In still another embodiment, at room temperature and in an oxygen permeable bag, at least about 85, 86, 87, 88, 89, 90, 91, 92, 93, 94, 95, 96, 97, or 98% of the initial total xanthophyll concentration is present at six months. In an exemplary embodiment, at room temperature and in an oxygen permeable bag, at least about 90% of the initial total xanthophyll concentration is present at six months.

In yet another embodiment, at room temperature and in an oxygen permeable bag, at least about 85, 86, 87, 88, 89, 90, 91, 92, 93, 94, 95, 96, 97, or 98% of the initial total xanthophyll concentration is present at nine months. In an exemplary embodiment, at room temperature and in an oxygen permeable bag, at least about 85, 86, 87, 88, 89, or 90% of the initial total xanthophyll concentration is present at nine months.

In embodiments where a composition of the invention is stored at 50° C. in an impermeable bag, at least about 90, 91, 92, 93, 94, 95, 96, 97, 98, 99, or 100% of the initial total xanthophyll concentration is present at up to about six months. In an exemplary embodiment, at least about 95, 96, 97, 98, 99, or 100% of the initial total xanthophyll concentration is present at up to about six months.

In other embodiments where a composition of the invention is stored at 50° C. in an impermeable bag, at least about 85, 86, 87, 88, 89, 90, 91, 92, 93, 94, 95, 96, 97, 98, 99, or 100% of the initial total xanthophyll concentration is present at nine months. In an exemplary embodiment, at least about 85, 86, 87, 88, 89, or 90% of the initial total xanthophyll concentration is present at nine months.

In a further exemplary embodiment, a composition of the invention, mixed with animal feed and stored at room temperature in a dark, oxygen permeable bag, maintains at least about 90% of the initial xanthophyll concentration after one month, and in some embodiments, maintains at least 90, 91, 92, 93, or 94% of the initial xanthophyll concentration after one month. In a still further exemplary embodiment, a composition of the invention, mixed with animal feed and stored at room temperature in a dark, oxygen permeable bag, maintains at least about 80% of the initial xanthophyll concentration after three, four, or six months, and in some embodiments, maintains at least about 80, 81, 82, 83, 84, 85, 86, 87, 88, 89, or 90% of the initial xanthophyll concentration after three, four, or six months.

(d) Formulations

A composition of the invention may either be a liquid or a solid. When the composition is a solid, the soap particles (which are comprised, in part, of non-esterified xanthophyll particles) are typically between about 40 microns to about 300 microns across the longest particle diameter. These particles may also form aggregates, ranging in size up to about 850 microns. In one embodiment, 90% of the soap particles or aggregates are between about 40 microns and about 850 microns. In another embodiment, 90% of the soap particles or aggregates are between about 70 microns and 700 microns. In yet another embodiment, 90% of the soap particles or aggregates are between about 100 microns and 550 microns. In still yet another embodiment, 90% of the soap particles or aggregates are between about 200 microns and about 500 microns. Such a soap contains non-esterified xanthophyll particles.

In certain embodiments, a composition of the invention may be formulated by itself, or as a part of a feed. A dry feed supplement may be uniformly dispersed throughout a liquid, a liquid food, a dry food, grain, protein products, feed supplements, or mixtures thereof.

In some embodiments, a composition of the invention may be formulated as an aqueous formulation. An aqueous formulation may be a solution, dispersion, or an emulsion. The aqueous formulation may be added directly to the drinking water of an animal or it may be mixed into or applied to a dry or liquid food.

(e) Antioxidants

A composition of the invention may also include at least one antioxidant. A variety of antioxidants or combination of antioxidants are suitable for use in a composition of the invention. The antioxidant may comprise a quinoline compound. Typically, the quinoline compound will be a substituted 1,2-dihydroquinoline. Substituted 1,2-dihydroquinoline compounds suitable for use in the invention generally comprise Formula (I):

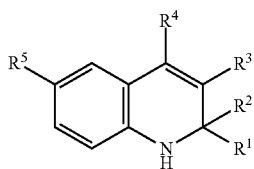

wherein:

$R^1$, $R^2$, $R^3$ and $R^4$ are independently selected from the group consisting of hydrogen and an alkyl group having from 1 to about 6 carbons; and $R^5$ is an alkoxy group having from 1 to about 12 carbons.

In an iteration, the substituted 1,2-dihydroquinoline comprises Formula (I), wherein:

$R^1$, $R^2$, $R^3$ and $R^4$ are independently selected from the group consisting of hydrogen and an alkyl group having from 1 to about 4 carbons;

and $R^5$ is an alkoxy group having from 1 to about 4 carbons.

In one preferred embodiment, the substituted 1,2-dihydroquinoline will be 6-ethoxy-1,2-dihydro-2,2,4-trimethylquinoline comprising Formula (II):

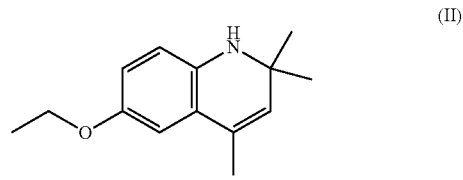 [SMILES: CCOc1ccc2c(c1)C(C)=CC(C)(C)N2]

The compound, 6-ethoxy-1,2-dihydro-2,2,4-trimethylquinoline, commonly known as ethoxyquin, is sold under the trademark AGRADO®. The present invention also encompasses salts of ethoxyquin and other compounds comprising Formula (I). Ethoxyquin and other compounds having Formula (I) may be purchased commercially from Novus International, Inc. (St. Louis, Mo.) or made in accordance with methods generally known in the art, for example, as detailed in U.S. Pat. No. 4,772,710, which is hereby incorporated by reference in its entirety.

A variety of other antioxidants are suitable for use in a composition of the present invention. In some embodiments, the antioxidant may be a compound that interrupts the free-radical chain of oxidative reactions by protonating free radicals, thereby inactivating them. Alternatively, the antioxidant may be a compound that scavenges the reactive oxygen species. In still other embodiments, the antioxidant may be a synthetic compound, a semi-synthetic compound, or a natural (or naturally-derived) compound.

Suitable antioxidants may include, but are not limited to, ascorbic acid and its salts, ascorbyl palmitate, ascorbyl stearate, anoxomer, n-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline (ethoxyquin), ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, n-hydroxysuccinic acid, hydroxytryrosol, hydroxyurea, rice bran extract, lactic acid and its salts, lecithin, lecithin citrate; r-alpha-lipoic acid, lutein, lycopene, malic acid, maltol, 5-methoxy tryptamine, methyl gallate, monoglyceride citrate; monoisopropyl citrate; morin, betanaphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof.

Exemplary antioxidants may include synthetic substituted phenolic compounds, such as tertiary butyl hydroquinone (TBHQ), butylated hydroxyanisole (BHA), or butylated hydroxytoluene (BHT); 6-ethoxy-1,2-dihydro-2,2,4-trimethylquinoline (ethoxyquin); gallic acid derivatives, such as n-propyl gallate; vitamin C derivatives, such as ascorbyl palmitate; lecithin; and vitamin E compounds, such as, alpha-tocopherol.

A composition of the invention may comprise at least one antioxidant. In some embodiments, a composition of the invention may comprise more than one antioxidant. By formulating a combination of antioxidants in this manner, a broad spectrum of fat sources, including fat sources relatively high in unsaturated fatty acids, may be utilized with a composition of the invention, such as in the animal feed ration or water source.

(f) Other Components

In certain embodiments, a composition of the invention may comprise other components, such as a carrier, a preservative, a free flow agent, etc. In certain embodiments, a composition of the invention may comprise a free flow agent. Suitable free flow agents are known in the art, and may comprise, for instance, a salt of stearic acid, $SiO_2$ and/or talc. In some embodiments, the free flow agent may be present in an amount of 0% to 15% by weight of the total composition, more preferably, the amount of the free flow agent is between 3% and 15%, or between 5% and 10%. Similarly, a composition of the invention may comprise a preservative. Suitable preservatives are known in the art. In still other embodiments, the composition may comprise an emulsifier. Suitable emulsifiers may comprise, for instance, a non-ionic emulsifier derived from propylene glycol or polyethyleneglycol ricinoleate (E-484).

(g) Exemplary Embodiments

In an exemplary embodiment, a composition of the invention is derived from marigold oleoresin. In another exemplary embodiment, 90% of the xanthophyll particles of a composition of the invention are less than 0.5 microns, the final soap product contains at least about 75 mg xanthophylls per gram of soap, and 80% of the non-esterified xanthophylls are the all-trans isomer. In a further exemplary embodiment, a composition of the invention comprises ethoxyquin. In still another exemplary embodiment, 98% of the xanthophyll present initially remains after one month at room temperature when stored in an oxygen permeable bag.

In another exemplary embodiment, a powder composition of the invention comprises between about 70% to about 99% marigold soap, between about 0% to about 15% free flow agent, between about 0.1% to about 3% metal hydroxide, between about 0.1% to about 2% moisture, and about 0% to about 1% antioxidant, such as ethoxyquin.

In yet another exemplary embodiment, a powder composition of the invention comprises between about 75% to about 95% marigold soap, between about 0% to about 15% free flow agent, and between about 0% to about 8% stearic acid.

In still another exemplary embodiment, a powder composition of the invention comprises between about 75% to about 95% marigold soap, between about 0% to about 15% $SiO_2$, and between about 0% to about 8% stearic acid.

In a further exemplary embodiment, a powder composition of the invention comprises between about 75% to about 95% marigold soap, between about 0% to about 15% talc, and between about 0% to about 8% stearic acid.

In a further exemplary embodiment, a powder composition of the invention comprises between about 75% to about 95% marigold soap, between about 0% to about 6% $SiO_2$, between about 2% to about 10% talc, and between about 0% to about 8% stearic acid.

In some exemplary embodiments, a liquid composition of the invention comprises between about 5 to about 25% marigold soap, between about 0 to about 0.6% antioxidant, such as ethoxyquin, between about 0 to about 1% emulsifier, and between about 82 to about 89% water. In a further exemplary embodiment, a liquid composition of the invention comprises between 0.5 and 3% xanthophylls, between about 0 to about 0.6% antioxidant, such as ethoxyquin, between about 0 to about 1% emulsifier, and between about 82 to about 89% water.

In other exemplary embodiments, a liquid composition of the invention comprises between about 5 to about 25% marigold soap, between about 0 to about 0.6% antioxidant, such as ethoxyquin, between about 0 to about 1% glyceryl polyethyleneglycol ricinoleate (E-484), and between about 82 to about 89% water. In a further exemplary embodiment, a liquid composition of the invention comprises between about 0 to about 3% xanthophylls, between about 0 to about 0.6% antioxidant, such as ethoxyquin, between about 0 to about 1% glyceryl polyethyleneglycol ricinoleate (E-484), and between about 82 to about 89% water.

II. Feed Rations

Another aspect of the present invention encompasses an animal feed. An animal feed of the invention comprises a composition as detailed in Section I above. The exact formulation of the animal feed composition is not critical to the present invention. Feed ingredients are selected according to the nutrient requirements of the particular animal for which the feed is intended; these requirements depend, interalia, upon the age and stage of development of the animal, the sex of the animal, and other factors. Feed ingredients may be grouped into eight classes on the basis of their composition and their use in formulating diets: dry forages and roughages; pasture, range plants and forages fed fresh; silages; energy feeds; protein supplements; mineral supplements; vitamin supplements; and additives. See National Research Council (U.S.) Subcommittee on Feed Composition, United States-Canadian Tables of Feed Composition, 3d rev., National Academy Press, pp. 2, 145 (1982). These classes are, to a certain extent, arbitrary, as some feed ingredients could be classified in more than one class. Typically, a feed formulation will also depend upon the costs associated with each ingredient, with the least-expensive composition of ingredients that gives the needed nutrients being the preferred formulation.

By way of non-limiting example, in one embodiment, the animal feed ration is formulated for poultry. As noted above, feed formulations depend in part upon the age and stage of development of the animal to be fed. Leeson and Summers (Nutrition of the Chicken, 4$^{th}$ ed., pp. 502-510, University Books, 2001) describe several representative poultry diets for pullets, layers, broilers and broiler breeders. For example, most chicken diets contain energy concentrates such as corn, oats, wheat, barley, or sorghum; protein sources such as soybean meal, other oilseed meals (e.g., peanut, sesame, safflower, sunflower, etc.), cottonseed meal, animal protein sources (meat and bone meal, dried whey, fish meal, etc.), grain legumes (e.g., dry beans, field peas, etc.), and alfalfa; and vitamin and mineral supplements, if necessary (for instance, meat and bone meal is high in calcium and phosphorous, and thus these minerals do not need to be supplemented in a feed ration containing meat and bone meal).

In another embodiment, the animal feed ration is formulated for swine. The feed formulation will vary for piglets, grower and finisher pigs, gilt development, gestating sows, and lactating sows. Swine feed formulations typically comprise grains (e.g., corn, barley, grain sorghum, oats, soybeans, wheat, etc.), crude proteins (e.g., fish meal, gluten meal, meat meal, soybean meal, tankage, which is the residue that remains after rendering fat in a slaughterhouse, etc.), crude fat (e.g., fish oils, vegetable oils, animal fats, yellow grease, etc.), supplemental amino acids (e.g., lysine, methionine or methionine analogs, etc), vitamins, minerals, and other supplemental agents.

In another embodiment, the animal ration is formulated for aquatic animals, for example in an aquaculture feed. As appreciated by a skilled aquaculturist, the feed formulation depends upon the organism being cultured and the developmental stage of the organism. Typical aquaculture preparations contain energy sources, e.g., protein from animal blood meal, meat and bone meal, poultry meal, crab meal, fish meal, shrimp meal, squid meal, and krill; protein/carbohydrates from plants (e.g., alginates, canola, corn, corn gluten, cottonseed meal, kelp meal, molasses, legumes, peanut meal, rice, soybeans, soy protein concentrate, soybean meal, wheat, and wheat gluten); and oils (e.g., fish oil, vegetable oil). The feed preparation may be further supplemented with amino acids (e.g., arginine, histidine, isoleucine, lysine, methionine, phenylalanine, threonine, tryptophan, and valine); vitamins, minerals, and other supplemental agents.

In another embodiment, the animal ration is formulated for a ruminant animal. The nutrient and energy content of many common ruminant feed ingredients have been measured and are available to the public. The National Research Council has published books that contain tables of common ruminant feed ingredients and their respective measured nutrient and energy content. Additionally, estimates of nutrient and maintenance energy requirements are provided for growing and finishing cattle according to the weight of the cattle. National Academy of Sciences, Nutrient Requirements of Beef Cattle, Appendix Tables 1-19, 192-214, National Academy Press, (2000); Nutrient Requirements of Dairy Cattle (2001), each incorporated herein in its entirety. This information can be utilized by one skilled in the art to estimate the nutritional and maintenance energy requirements of cattle with non-functional rumens, such as calves under about 500 lbs in weight, or cattle with functional rumens, such as growing cattle or dairy cattle.

(a) Additional Ingredients

A composition of the invention may be provided to the animal in the form of a feed premix or feed supplement. The premix will generally be added to various formulations of grain concentrates and forages to formulate a total animal feed ration. As will be appreciated by the skilled artisan, the particular premix formulation can and will vary depending upon the feed ration and animal that the feed ration will be fed to. In addition to combinations of the invention, the premix may further optionally include one or more of a mixture of natural amino acids, analogs of natural amino acids, vitamins and derivatives thereof, enzymes, animal drugs, hormones, effective microorganisms, preservatives, and flavors.

In one embodiment, the feed premix may include one or more amino acids. Suitable examples of amino acids, depending upon the formulation, may include alanine, arginine, asparagines, aspartate, cysteine, glutamate, glutamine, glycine, histidine, isoleucine, leucine, lysine, methionine, phenylalanine, proline, serine, threonine, tryptophan, tyrosine, and valine. Other amino acids usable as feed additives include, by way of non-limiting example, N-acylamino acids, hydroxy homologue compounds, and physiologically acceptable salts thereof, such as hydrochlorides, hydrosulfates, ammonium salts, potassium salts, calcium salts, magnesium salts and sodium salts of amino acids.

In still another embodiment, a feed premix may include vitamins or derivatives of vitamins. Examples of suitable vitamins and derivatives thereof may include vitamin A, vitamin A palmitate, vitamin A acetate, β-carotene, vitamin D (e.g., $D_2$, $D_3$, and $D_4$), vitamin E, menadione sodium bisulfite, vitamin B (e.g., thiamin, thiamin hydrochloride, riboflavin, nicotinic acid, nicotinic amide, calcium pantothenate, pantothenate choline, pyridoxine hydrochloride, cyanocobalamin, biotin, folic acid, p-aminobenzoic acid), vitamin K, vitamin Q, vitamin F, and vitamin C.

In yet another embodiment, a feed premix may include one or more enzymes. Suitable examples of enzymes may include protease, amylase, lipase, cellulase, xylanase, glucanase, pectinase, phytase, hemicellulase and other physiologically effective enzymes.

In still another embodiment, a feed premix may include a drug approved for use in animals. Non-limiting examples of suitable animal drugs may include antibiotics such as tetracycline type (e.g., chlortetracycline and oxytetracycline), amino sugar type, ionophores (e.g., rumensin, virginiamycin, and bambermycin) and macrolide type antibiotics.

In an additional embodiment, a feed premix may include a hormone. Suitable hormones may include estrogen, stilbestrol, hexestrol, tyroprotein, glucocorticoids, insulin, glucagon, gastrin, calcitonin, somatotropin, and goitradien.

In an additional embodiment, a feed premix may include a substance to increase the palatability of the feed ration. Suitable examples of such substances may include natural sweeteners, such as molasses, and artificial sweeteners such as saccharin and aspartame.

As will be appreciated by the skilled artisan, any of the substances that may be included in a premix comprising a composition of the invention can be used alone or in combination with one another. The concentration of these additives will depend upon the animal the premix is intended for, and the desired result.

(b) Encapsulation

In yet another embodiment, the product is encapsulated. As used herein, an encapsulated composition is a composition that has been packaged in a material. In many cases, encapsulation provides protection from degradation from light, heat, oxygen and moisture. Encapsulation may also provide release under specific conditions or protect an active ingredient from degrading before reaching a point in the digestive system where it can be absorbed. Encapsulation, in some instances, is provided by spray coating or spray drying, extrusion, coating which generally involves forcing a core material in a molten wall material through a die into a bath of desiccant liquid. Upon contacting the liquid, the coating material hardens forming the outer encapsulation. Encapsulation may be provided, in some instances, by inclusion complexation, or molecular inclusion, using, for example, cyclodextrin. In still another embodiments, encapsulation may be provided by coacervation, emulsion phase separation, or liposome entrapment. In another, exemplary embodiment, the product is not encapsulated.

III. Process

In another aspect, the invention encompasses a continuous process for creating a final soap product with a non-esterified carotenoid concentration of greater than 10%. The process comprises (a) alkaline saponification of a natural carotenoid-containing oleoresin, wherein the saponification occurs in the presence of a metal hydroxide, with intimate mixing, and occurs at a temperature between about 110° C. to about 180° C. resulting in a soap comprising non-esterified carotenoids, (b) atomization of the soap from step (a), and (c) isomerization of the non-esterified carotenoids, wherein the atomized soap is heated such that greater than 80% or more of the non-esterified carotenoids present in the soap in the all-trans isomer configuration, and the non-esterified carotenoid concentration of the final product is greater than 10%. In certain embodiments, the soap is also dried. Drying may be performed, for instance, during atomization, after atomization, before isomerization, during isomerization, after isomerization, or a combination thereof.

(a) Alkaline Saponification

The process comprises alkaline saponification of a natural carotenoid-containing oleoresin, wherein the saponification occurs in the presence of a metal hydroxide, with intimate mixing, and occurs at a temperature between about 110° C. to about 180° C. resulting in a soap composition comprising non-esterified carotenoids. Through this process, the carotenoids found in the natural carotenoid-containing oleoresin which are initially bound to fatty acids through ester moieties may be released by hydrolysis, or de-esterification from the fatty acid moiety. The result is non-esterified carotenoids, or carotenoids no longer bound as fatty esters within the soap.

i. Natural Carotenoid-Containing Oleoresin

The natural carotenoid-containing oleoresin to be saponified is fed into the continuous flow apparatus. Depending on how the natural carotenoid-containing oleoresin was extracted from the plant, suitable oleoresins may be 100% solvent free (e.g. supercritical extraction) or contain trace amounts of solvent (for example volatile organic solvents including but not limited to butane and hexane). In some embodiments, the natural carotenoid-containing oleoresin is purchased from a commercial supplier. The natural carotenoid-containing oleoresin may contain an antioxidant as it is purchased, or an antioxidant may be mixed with the natural carotenoid-containing oleoresin. In some embodiments, a surfactant, solvent, or free flow agent is mixed with the natural carotenoid-containing oleoresin prior to the process.

ii. Antioxidant

In some embodiments, an antioxidant is additionally introduced into the continuous flow apparatus either as an added ingredient or as premixed with another reagent, such as, the oleoresin. Suitable antioxidants may include, but are not limited to, those listed in Section I(e) above.

The antioxidant may be provided in an amount between about 0.25% and about 5% to the natural carotenoid-containing oleoresin on a weight basis. In some embodiments, the antioxidant may be provided in an amount of 0.25%, about 0.5%, about 0.75%, about 1%, about 2%, about 3%, about 4%, or about 5% on a weight basis to the natural carotenoid-containing oleoresin. In one preferred embodiment, the antioxidant is provided on a 3% weight basis to the natural carotenoid-containing oleoresin. The antioxidant may be provided pre-mixed with the natural carotenoid-containing oleoresin or may be provided separately.

iii. Proton Acceptor

Saponification occurs in the presence of a proton acceptor, or a strong base which may be a alkaline reagent. In some embodiments, saponification is achieved in the presence of a metal hydroxide. Suitable metal hydroxides, include, but are not limited to, sodium hydroxide, potassium hydroxide, calcium hydroxide, and magnesium hydroxide. In one preferred embodiment, the proton acceptor is potassium hydroxide.

The metal hydroxide is generally present in a solution which is preferably an aqueous solution. In some embodiments, the metal hydroxide solution ranges from about 10% to about 70%, or, in other embodiments the solution ranges from about 20% to about 60%. In other embodiments, the metal hydroxide is present in about a 10% solution, about a 20% solution, about a 30% solution, about a 40% solution, about a 50% solution, about a 60% solution, or about a 70% solution. In one preferred embodiment, the metal hydroxide is a 50% aqueous solution of potassium hydroxide.

The ratio of natural carotenoid-containing oleoresin to metal hydroxide can and will vary in alternate embodiments, and may be influenced by the concentration of the metal hydroxide and the rate of introduction in the continuous flow apparatus. In some embodiments, the ratio of the metal hydroxide solution to the natural carotenoid-containing oleoresin is about 10% to about 50% on a weight basis, or more preferably from about 28 to about 30%. In some embodiments, the ratio of the metal hydroxide solution to the natural carotenoid-containing oleoresin is about 10%, about 15%, about 20%, about 25%, about 30%, about 35%, about 40%, about 45%, or about 50% on a weight by weight basis.

iv. Temperature

Heat is provided to the saponification step to facilitate the reaction. In general, the temperature may range from about 110° C. to about 180° C. The heat may be provided by heating devices in connection with the continuous flow apparatus. These devices may be set at temperatures ranging from about 110° C. to about 120° C., from about 115° C. to about 125° C., from about 120° C. to about 130° C., from about 125° C. to about 135° C., from about 130° C. to about 140° C., from about 135° C. to about 145° C., from about 140° C. to about 150° C., from about 145° C. to about 155° C., from about 150° C. to about 160° C., from about 165° C. to about 175° C., from about 170° C. to about 180° C. In one preferred embodiment, the heating is provided by a jacketing device surrounding the continuous flow apparatus which is set to about 140° C.

v. Pre-Heating

In one embodiment, the solution containing the proton acceptor, the natural carotenoid-containing oleoresin, or both are pre-heated prior to contacting. The reagents may be preheated in a reagent container prior to entering the continuous flow apparatus, or may be heated in the continuous flow apparatus prior to contacting of the two reagents. Heating can be provided by a variety of sources including through conduction or convection. Exemplary heating sources include heating jackets, heat exchangers, and the like.

Preferably, the natural carotenoid-containing oleoresin is pre-heated and maintained in a reagent container prior to entry in the continuous flow apparatus. In such embodiments, the heated natural carotenoid-containing oleoresin exhibits enhanced flowability and pumpability in the continuous flow apparatus. The natural carotenoid-containing oleoresin may be maintained at a temperature ranging from about 50° C. to about 70° C. In certain embodiments, the natural carotenoid-containing oleoresin is heated to a temperature of about 50° C., about 55° C., about 60° C., about 65° C., or about 70° C. In one preferred embodiment, the natural carotenoid-containing oleoresin is heated to a temperature of about 60° C. prior to introduction into the continuous flow apparatus.

The proton acceptor may be pre-heated prior to contacting with the natural carotenoid-containing oleoresin. The metal hydroxide may be heated to a temperature ranging from about 60° C. to about 150° C. More preferably, the metal hydroxide is heated to a temperature of about ranging from about 80° C. to about 90° C. In alternate embodiments, the metal hydroxide is heated to a temperature of about 75° C., about 80° C., about 85° C. or about 90° C. In one preferred embodiment, the metal hydroxide is heated to a temperature of 90° C. by a plates heat exchanger within the continuous flow apparatus.

vi. Intimate Mixing

The saponification step comprises intimate mixing. Intimate mixing, as used herein, refers to high shear mixing, homogenization, such as through a homogenizer (including a rotor stator type homogenizer, a high pressure homogenizer), sonification, or through ultrasonification. In one preferred embodiment, mixing is provided by a high shear mixer within the continuous flow apparatus. In some embodiments, intimate mixing is provided in combination with other kinds of mixing, for example, static mixing.

(b) Atomization

The process further comprises a step where the non-esterified carotenoid soap produced in step (a) is atomized. Methods of atomization are known in the art. For instance, the atomization step may be achieved through spraying the product comprising the non-esterified carotenoids produced in step (a) through a nozzle or spinning disc into the spraying chamber. A gas flow may also be introduced into the atomizing chamber as either a counter or co-current in relation to the spraying flow direction. As the liquid product from (a) is released, the soap composition containing the non-esterified carotenoids is distributed as small droplets into the gas stream. The sprayed droplets may be dried or cooled by the gas. The gas may be atmospheric air or an inert gas chosen from argon, nitrogen, and combinations thereof. In some embodiments, a gas stream is used to deliver an additional free flow agent which is distributed amongst the atomized soap droplets as they pass through the atomizer.

i. Temperature

The temperature that atomization takes place at may range from about 15° C. to about 100° C. More preferably, the temperature within the atomizer ranges from about 30° C. to about 80° C. In alternate embodiments, the temperature within the atomizer is about 45° C., about 55° C., about 65° C., or about 75° C. In one preferred embodiment, the temperature in the atomizer is about 50° C.

ii. Free Flow Agent

A free flow agent may be used to enhance the flowability of the final soap product. The free flow agent may be introduced during atomization through a gas stream in the atomizer. The free flow agent may be selected from free flow agents known in the art. Suitable examples may include, but are not limited to, tricalcium phosphate, powdered cellulose, calcium stearate, magnesium stearate, sodium bicarbonate, sodium ferrocyanide, calcium ferrocyanide, potassium ferrocyanide, bone phosphate, sodium silicate, silicon dioxide, calcium silicate, magnesium trisilicate, talcum powder, sodium aluminum silicate, potassium aluminum silicate, calcium aluminosilicate, bentonite, aluminum silicate, stearic acid, polydimethylsiloxane, glucose, maltodextrin, hydrophobically modified starch, and the like. In one preferred embodiment, the free flow agent is silicon dioxide. In another preferred embodiment, the free flow agent is talc.

The amount of free flow agent which is added may range from about 3% to about 15%, or more preferably from about 5% to about 10% of the weight of the final soap product. In some embodiments, the free flow agent is about 0.5%, about 1%, about 1.5%, about 2%, about 2.5%, about 3%, about 4%, about 5%, about 6%, about 7%, about 8%, about 9%, about 10%, about 11%, about 12%, about 13%, or about 14%, or about 15% of the weight of the final soap product.

iii. Moisture Content

The atomizer may reduce the moisture content of the product exiting the atomizer. In certain embodiments, the moisture content of the product after atomization is between about 5% and about 15%, more preferably between about 10% and about 13%. In certain embodiments, the moisture content of the product exiting the atomizer is about 5%, about 6%, about 7%, about 8%, about 9%, about 10%, about 11%, about 12%, about 13%, about 14%, or about 15%.

(c) Isomerization

The continuous flow process further comprises isomerization of the non-esterified carotenoids, wherein the atomized soap is heated such that greater than 80% of the non-esterified carotenoids present are in the all-trans isomer configuration, and the non-esterified carotenoid concentration of the final product is greater than 10%.

Isomerization transforms cis-xanthophylls to all-trans-isomers and is generally achieved with thermal heating. Thermal heating may be provided to the product in a number of ways including through a fluid bed dryer, a heated vibrating conveyer, an oven or a thermal processor.

The temperature at which isomerization is conducted can and will vary in different embodiments, and over the course of the isomerization step. The temperature may range from about 40° C. to about 120° C. In some embodiments, the isomerization step may be conducted at a temperature ranging from about 75° C. to about 80° C., about 80° C. to about 85° C., about 85° C. to about 90° C., about 90° C. to about 95° C., about 95° C. to about 100° C., or about 100° C. to about 105° C.

Isomerization may be conducted over a period of time from about 1 hour to about 48 hours. In some embodiments, isomerization is conducted over a period of time of about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours or about 24 hours. In one embodiment, isomerization occurs at a temperature between about 75° C. and about 95° C. over a period ranging from about 1 hour to about 3 hours.

In some embodiments, isomerization may occur in more than one temperature stage. Isomerization may be conducted at a first range of temperatures from about 40° C. to about 60° C. Without being bound to any theory, it is thought that thermal contact at the first range of temperatures may decrease moisture content from about 2% to about 5%. The first temperature may be maintained for a period of about 15 minutes to about 2 hours. A second range of temperatures is used to increase the all-trans isomer content. The second range of temperatures may range from about 70° C. to about 90° C. and the second temperature may be maintained for a period ranging from about 30 minutes to about 3 hours. In one preferred embodiment, isomerization is conducted at a first temperature of about 50° C. for about 30 minutes and at a second temperature of 80° C. for about 1.5 hours. In an alternate embodiment, temperature is increased over the course of the reaction from a lower temperature ranging from about 40° C. to about 60° C. to a higher temperature ranging from about 70° C. to about 90° C.

In some embodiments, the isomerization takes place under an inert atmosphere. The inert atmosphere may be chosen, by way of non-limiting example, from argon, nitrogen, or combinations thereof. In one preferred embodiment, isomerization is conducted in the presence of nitrogen gas.

In some embodiments, greater than 70% of the non-esterified carotenoids present after atomization are all-trans isomers. In other embodiments, greater than 75%, or 80%, or 85%, or 90% of the carotenoids are transformed to the all-trans isomer. The isomerization step may increase the total all-trans carotenoid content of the final soap product. Isomerization may increase the all-trans carotenoid content by greater than 5%, or greater than 10%, or greater than 15% of the final soap product. In one embodiment, the total all-trans carotenoid content of the final soap product is greater than 10%.

After isomerization the final soap product may be transferred to a product container. The final soap product possesses the properties described in Section I. In some embodiments, additional agents such as free flow agents may be added to the product after isomerization, in addition to those added during the atomization step.

(d) Continuous Flow Apparatus

The process is conducted in a continuous flow manner in a continuous flow apparatus. By "continuous flow" it is meant that the reaction takes place in motion within a reactor or that starting materials and conditions are continually added and withdrawn as produced. A schematic of the continuous flow apparatus and related equipment is shown in FIG. 1. While the preferred method is continuous, it is also possible to perform the method in a discontinuous fashion. That is to say, the method may be stopped and re-started at a different time or in a different physical location.

Referring to FIG. 1, a first solution of the metal hydroxide within a first reagent container 102 may be conducted through a first conduit 106 to a first static mixer 112. A second solution comprising the natural carotenoid-containing oleoresin within a second reagent container 104 may be transferred into a first static mixer 112 through a second conduit 108. In one embodiment, reagent container 104 is heated by a heat transfer device 105. The heat transfer device may be chosen from, without limitation, electric heaters, inductive heaters, gas heaters, oil heaters, ceramic heaters and the like, or more particularly from plates heat exchangers and tube heat exchangers. In one embodiment, a heat transfer device 110 is used to heat the metal hydroxide as it passes through the continuous flow apparatus.

The conduits 106 and 108 may be controllable transfer pumps that pump reagents from the reagent containers across the conduits to the first static mixer 112. The conduits may be controllable pressure pumps that pressurize the reagents stored within the reagent containers to predetermined pressures selected to move the reagents out of the containers at desired transfer rates, and any combination thereof. Non-limiting examples of pumps suitable for use as transfer pumps include gear pumps, diaphragm pumps, centrifugal pumps, piston pumps, and peristaltic pumps. In certain embodiments, the conduits are peristaltic pumps and are responsible, in addition to the size of various parts of the continuous flow apparatus, for the flow rate.

The flow rate for the continuous process may vary in different embodiments. In particular, the flow rate may be higher or lower depending on the production requirements and other factors known to the skilled artisan. In some embodiments, the flow rate may range between 100 kg/hr and 300 kg/hr, or from 50 kg/hr to 250 kg/hr, or 50 kg/hr to 300 kg/hr. In some embodiments, the flow rate may range from about 50 kg/hr to about 100 kg/hr, from about 75 kg/hr to about 125 kg/hr, from about 100 kg/hr to about 150 kg/hr, from about 125 kg/hr to about 175 kg/hr, from about 150 kg/hr to about 200 kg/hr, from about 175 kg/hr to about 225 kg/hr, from about 200 kg/hr to about 250 kg/hr, from about 225 kg/hr to about 275 kg/hr, from about 250 kg/hr to about 300 kg/hr. In other embodiments, the flow rate may range from about 100 kg/hr to about 200 kg/hr, from about 150 kg/hr to about 250 kg/hr, from about 200 kg/hr to about 300 kg/hr. In preferred embodiments, the flow rate ranges from about 150 kg/hr to about 250 kg/hr.

The first static mixer 112 receives reagents continuously. The first static mixer is generally tube-shaped and can be straight, curved, or a combination of straight and curved tubes. The static mixer contains a variety of elements inside the tubes giving patterns of flow and providing mixing to the reagents as they pass through the tube. The elements may provide mixing, for example, by creating laminar flow or for example by creating radial mixing. The first static mixer has a diameter and length that, in conjunction with the flow rate, achieves a particular residence time for the reagents.

In some embodiments, the first static mixer has a diameter of about 20 mm to about 150 mm. In some embodiments, the first static mixer has a diameter from about 20 mm to about 30 mm, from about 25 mm to about 35 mm, from about 30 mm to about 40 mm, from about 35 mm to about 45 mm, from about 40 mm to about 50 mm, from about 45 mm to about 55 mm, from about 50 mm to about 60 mm, from about 55 mm to about 65 mm, from about 60 mm to about 70 mm, from about 65 mm to about 75 mm, from about 70 mm to about 80 mm, from about 75 mm to about 85 mm, from about 80 mm to about 90 mm, from about 95 mm to about 105 mm, from about 100 mm to about 110 mm, from about 105 mm to about 115 mm, from about 110 mm to about 120 mm, from about 115 mm to about 125 mm, from about 120 mm to about 130 mm, from about 125 mm to about 135 mm, from about 130 mm to about 140 mm, from about 135 mm to about 145 mm, from about 140 mm to about 150 mm. In one preferred embodiment, the diameter of the first static mixer is 50 mm.

In one embodiment, the first static mixer 112 is connected to a high shear mixer 116, which provides intimate mixing in addition to the static mixer. In one embodiment, a four blade slotted cylinder stator is utilized. The size of the stator can and will vary depending on other parameters. The rotations per minute (rpm) of the blades can vary in different embodiments. In some embodiments, the speed ranges from 2000 rpm to about 3500 rpm. In certain embodiments the speed is 2000 rpm, 2100 rpm, 2200 rpm, 2300 rpm, 2400 rpm, 2500 rpm, 2600 rpm, 2700 rpm, 2800 rpm, 2900 rpm, 3000 rpm, 3100 rpm, 3200 rpm, 3300 rpm, 3400 rpm, or 3500 rpm.

The high shear mixer 116 may be connected directly or by way of additional tubing to a second static mixer 118. Where there is a second static mixer, the second static mixer 118 may be tube shaped and can be straight, curved, or a combination of straight and curved. In some embodiments, the second static mixer has a diameter of about 20 mm to about 200 mm. In some embodiments, the first static mixer has a diameter from about 20 mm to about 30 mm, from about 25 mm to about 35 mm, from about 30 mm to about 40 mm, from about 35 mm to about 45 mm, from about 40 mm to about 50 mm, from about 45 mm to about 55 mm, from about 50 mm to about 60 mm, from about 55 mm to about 65 mm, from about 60 mm to about 70 mm, from about 65 mm to about 75 mm, from about 70 mm to about 80 mm, from about 75 mm to about 85 mm, from about 80 mm to about 90 mm, from about 95 mm to about 105 mm, from about 100 mm to about 110 mm, from about 105 mm to about 115 mm, from about 110 mm to about 120 mm, from about 115 mm to about 125 mm, from about 120 mm to about 130 mm, from about 125 mm to about 135 mm, from about 130 mm to about 140 mm, from about 135 mm to about 145 mm, from about 140 mm to about 150 mm. In one preferred embodiment, the diameter of the first static mixer is 125 mm.

Temperature may also be controlled during static mixing by heat transfer devices. In some embodiments, the first and second static mixers are jacketed with a heat transfer device to maintain the passing liquid at a given temperature.

The residence time from the introduction of the reagents to the end of the second static mixer may range from about 30 seconds to about 5 minutes, and is dependent, in part, on temperature. Generally speaking, for higher temperatures, less residence time is required. Similarly, for lower temperatures, higher residence time is required. In some embodiments, the residence time is about 30 seconds, 45 seconds, about 1 minute, about 1.5 minutes, about 2 minutes, about 2.5 minutes, about 3 minutes, about 3.5 minutes, about 4 minutes, about 4.5 minutes or about 5 minutes. In one embodiment, the residence time is about 95 seconds.

The second static mixer is connected either directly or through additional tubing to the Piston Flow Reactor 120. The piston flow reactor is a tubular reactor which may be divided into separate compartments, each comprising a smaller tubular reactor. In some embodiments the tubular reactor comprises four tubular reactors. Temperature is controlled within the piston flow reactor. In one embodiment, the piston flow reactor is jacketed to a temperature above 100° C. In one embodiment, the piston flow reactor is jacketed to a temperature ranging from about 130° C. to about 150° C. In one preferred embodiment, the jacket temperature is about 140° C. The piston flow reactor is preferably oriented upward such that the tubular apparatus directs the flow of reagents perpendicular to the ground longer than they are oriented parallel to the ground. The residence time in the Piston Flow Reactor can and will vary, preferably from about 5 minutes to about 10 minutes. In particular embodiments, the residence time in the piston flow reactor is 5 minutes, 6 minutes, 7 minutes, 8 minutes, 9 minutes, or 10 minutes. In one preferred embodiment, the residence time is 8 minutes.

Pressure within the continuous flow apparatus may be regulated through a barometric sensing device and one or more valves 124 found along the continuous flow apparatus. The valves are releasably sealed to the environment surrounding the continuous flow apparatus. When pressure reaches a threshold level, the valves may be opened to release gas to the environment surrounding the continuous flow apparatus. In preferred embodiments, the valve 124 is positioned before the atomizer 122.

The atomizer 122 may comprise a spinning circular disc for the introduction of the product from the piston flow reactor. The spinning of the disc may result in a spray of the liquid. Near the spinning disc, one or more gas blowers may be present such that the gas and sprayed liquid are in contact as they move through the atomizing chamber. Drying and/or solidification of the liquid product containing the non-esterified carotenoids may occur at this point. In some embodiments, the one or more gas blowers may contain a stream of free flow agent from the free flow agent container 128. The free flow agent may additionally be blown into the chamber such that it comes in contact with the sprayed product to form a dried product containing the free flow agent as it moves through the continuous flow apparatus.

The liquid product may be introduced to the atomizer with a feed rate ranging from about 100 kg/hr to about 300 kg/hour, or from about 50 kg/hr to about 250 kg/hr, or from about 150 kg/hr to 250 kg/hour. In some embodiments, the feed rate may range from about 50 kg/hr to about 100 kg/hr, from about 75 kg/hr to about 125 kg/hr, from about 100 kg/hr to about 150 kg/hr, from about 125 kg/hr to about 175 kg/hr, from about 150 kg/hr to about 200 kg/hr, from about 175 kg/hr to about 225 kg/hr, from about 200 kg/hr to about 250 kg/hr, from about 225 kg/hr to about 275 kg/hr, from about 250 kg/hr to about 300 kg/hr. In other embodiments, the flow rate may range from about 100 kg/hr to about 200 kg/hr, from about 150 kg/hr to about 250 kg/hr, from about 200 kg/hr to about 300 kg/hr. In a preferred embodiment the feed rate is about 150 kg/hr.

In some embodiments, the spinning disk feed to the atomizer has a speed of about 10,000 rpm to about 30,000 rpm, or more preferably from about 20,000 rpm to about 25,000 rpm. In particular embodiments, the spinning disk feed is about 20,000 rpm, about 21,000 rpm, about 22,000 rpm, about 23,000 rpm, about 24,000 rpm, or about 25,000 rpm.

The residence time in the atomizer can and will vary among various embodiments. In one embodiment, the mean residence time will range from about 10 and about 14 seconds. In other embodiments, the mean residence time is about 10 seconds, about 11 seconds, about 12 seconds, about 13 seconds, and about 14 seconds.

The chamber dimensions for the atomizer may range from a diameter of about 2000 mm to about 2500 mm. In alternate embodiments, the chamber dimensions for the atomizer may range from about 2200 mm to about 2400 mm. In one preferred embodiment, the chamber dimensions for the atomizer are about 2300 mm.

The gasses introduced into the atomizer are introduced with a particular flow rate. This flow rate may range from about 2500 $m^3$/hour to about 3500 $m^3$/hour. In some embodiments, the flow rate for the gasses introduced into the atomizer range from about 2900 $m^3$/hour and 3100 $m^3$/hour. In a preferred embodiment, the flow rate is about 3000 $m^3$/hour.

The atomizer is connected either directly to or through a series of tubes to the isomerization apparatus 126. The reagents from the atomizer 122 are fed into the isomerization apparatus 126. The isomerization apparatus may be a closed tank with a series of rotating circular trays inside the tank. The reagents are fed to a top rotating tray, where additional rotating trays are directly below the top rotating tray. After each rotation the products are dropped onto a lower tray and leveled by stationary baffles as the tray rotates. The closed tank may be heated to a certain temperature and may additionally have a flowing gas.

From the isomerization apparatus, the reagents may be fed into a product container 130. The product container may be sized and configured to accept product from the continuous flow apparatus. In some embodiments, the product container is connected to a free flow agent container 128, which optionally may contain the same free flow agent as the atomizer 122. The free flow agent may be blown into the product container 130 via an air stream to increase the percentage of the free flow agent.

The various components of the continuous flow apparatus may be made of a variety of suitable materials. Suitable examples of materials may include, but are not limited to, metal (including stainless steel, brass), glass (including, but not limited to, borosilicate glasses), and polymers (including, but not limited to, fluorinated poly(ethylene) (FPE), fluorinated ethylene poly(propylene) (FEP), high density poly(ethylene) (HDPE), poly(chlorotrifluoroethylene) (PCT), poly(ether ether ketone) (PEEK), poly(tetrafluoroethylene) (PTFE), poly(vinyl fluoride) (PVF), perfluoroalkoxy (PFA) polymers, and combinations or copolymers thereof).

(e) Optional Process for Liquid Formulation

In one alternative embodiment, the process produces a liquid formulation. In such embodiments, the atomization step (b) is not performed, but rather the product produced in step (a) is isomerized as described in (c) and then is quenched in a water tank. A continuous flow reactor as described in section (d) and shown in FIG. 1 may be modified such that the atomizer is not present and the isomerized product is directed to a water tank where the isomerized product is diluted in water.

The ratio of isomerized product to water can and will vary. In some embodiments, the solution ranges from about a 0.25% solution to about a 10% solution in water. In other embodiments the solution ranges from about a 0.5% solution in water to about a 5% solution in water. In one preferred embodiment the solution is about a 1% solution in water to about a 2% solution in water.

In one embodiment, the isomerization of the non-esterified carotenoids, wherein the diluted soap is heated such that greater than 80% of the non-esterified carotenoids present are in the all-trans isomer configuration, produces a non-esterified carotenoid concentration of the final soap product is greater than 10%.

In still another alternative embodiment, the process produces a liquid formulation. In such embodiments, the atomization step (b) is not performed, but rather the product produced in step (a) is quenched in a water tank and then is isomerized as described in section (c).

IV. Methods of Using a Composition of the Invention

A composition of the invention may be used to increase the carotenoid content of various articles, including animal products. Such methods include methods of increasing pigmenting efficiency. A composition of the invention may also be used to improve animal health or performance. Additionally, a composition of the invention may be used to aid in the preservation of feed compositions. Each of these methods are discussed in more detail below.

(a) Methods of Increasing the Carotenoid Content of an Article

A composition of the invention may be used to increase the carotenoid content of an article. For instance, a composition of the invention may be used to increase the carotenoid content of an animal feed or an animal supplement. In such embodiments, the method comprises combining a composition of the invention with an animal feed or an animal supplement. For instance, an animal feed or supplement may comprise about 100, 95, 90, 85, 80, 75, 70, 65, 60, 55, 50, 45, 40, 35, 30, 25, 20, 15, 10, or 5% of an animal feed or an animal supplement.

In some embodiments, a composition of the invention may be fed to an animal to increase the carotenoid content of certain animal products. In such embodiments, a composition of the invention may be fed to the animal by itself, or as a part of an animal feed or animal supplement. For example, poultry (or other egg laying fowl) may be fed a composition of the invention, either alone or as part of a poultry feed or supplement to increase the carotenoid content of egg yolk, or the carotenoid content of broiler chicken skin, feet, or other organs.

The amount of carotenoid composition to administer to an animal to increase the carotenoid content of an animal product may be determined using methods well known in the art. Generally speaking the amount may range from between about 1 mg xanthophyll/kg complete feed to about 100 mg xanthophylls/kg complete feed. In some embodiments, the amount of carotenoid composition to administer may be about 1, 5, 10, 15, 20, 25, 30, 35, 40, 45, 50, 55, 60, 65, 70, 75, 80, 85, 90, 95, 100, or more than 100 mg xanthophyll/kg feed. In other embodiments, the amount may be about 1, 2, 3, 4, 5, 6, 7, 8, 9, or 10 mg xanthophylls/kg complete feed.

A composition of the invention may be used to increase the pigmenting of a product, especially a food product for human consumption. For example, a composition of the invention may be used to provide pigmenting to egg yolk (for a variety of fowl), the flesh of certain animals consumed by humans (such as broiler skin, or the flesh or meat of certain aquaculture, including fish), or other organs of animals consumed by humans. Advantageously, an equal amount of a composition of the invention has a greater pigmenting efficiency than other carotenoid soap compositions. For instance, compared to other carotenoid soap compositions, a composition of the invention may have greater than 90, 100, 110, 120, 130, 140, 150, 160, 170, 180, 190, or 200% increased pigmenting efficiency. In some embodiments, a composition may have greater than 100, 105, 110, 115, 120, 125, or 130% increased pigmenting efficiency compared to other carotenoid soap compositions.

In one embodiment, the composition of the invention is added to a poultry diet. As will be appreciated by one of skill in the art, the amount fed per day depends on the size and desired coloration. In some embodiments, a layer diet includes about 2 ppm of the composition of the invention, about 3 ppm, about 4 ppm, about 5 ppm, about 6 ppm, about 7 ppm, or about 8 ppm. In still another embodiment, a broiler diet contains about 20 ppm, about 25 ppm, about 30 ppm, about 35 ppm, about 40 ppm, about 45 ppm, or about 50 ppm of the composition of the invention.

(b) Methods for Improving Animal Health and Performance

Another aspect of the invention provides methods for improving animal health and performance by providing a composition of the invention to the animal of interest. Those of skill in the art will appreciate that the amount of composition provided to a particular animal can and will vary depending upon the species, sex, and age of the animal.

Furthermore, a variety of health and performance parameters may be affected by administration of a composition of the invention.

In some embodiments, a composition of the invention may be provided to poultry, such as laying chickens, broiler chickens, turkeys, and ducks. Examples of suitable health parameters may include, but are not limited to, body weight, body condition score, body temperature, food intake, antioxidant status, markers of oxidative stress, serum protein levels, serum mineral levels, immune system function (immune stimulation), health and diversity of gut microflora, fecal bacteria, bone and joint health, and so forth. Non-limiting examples of suitable performance parameters may include weight gain, feed:gain ratio, nutrient digestibility, feed conversion ratio, egg yield, egg quality, eggshell quality, yolk color, skin color, carcass quality, carcass yield, meat grade, meat yield, meat protein to fat ratio, and the like.

In some embodiments, a composition of the invention may be provided to dairy ruminants, such as dairy cattle, dairy sheep, and dairy goats. In a preferred embodiment, the dairy ruminant is a dairy cow. Non-limiting examples of suitable health parameters to be assessed may include body weight, body condition score, body temperature, food intake, antioxidant status, markers of oxidative stress, serum protein levels, serum mineral levels, immune system function, health and diversity of rumen microflora, fecal bacteria, and so forth. Suitable performance parameters may include, but are not limited to, milk yield, milk efficiency, milk fat, milk protein, somatic cell counts, FCM, ECM weight gain, feed:gain ratio, nutrient digestibility, feed conversion ratio, pregnancy rate, number of offspring, weight of offspring, and so forth.

In other embodiments, a composition of the invention may be fed to non-dairy ruminants, such as beef cattle, veal, and lambs. Examples of suitable health parameters may include but are not limited to body weight, body condition score, body temperature, food intake, antioxidant status, markers of oxidative stress, serum protein levels, serum mineral levels, immune system function, health and diversity of rumen microflora, fecal bacteria, bone and joint health, and so forth. Non-limiting examples of suitable performance parameters may include weight gain, feed:gain ratio, nutrient digestibility, feed conversion ratio, carcass quality, carcass yield, meat grade, meat yield, meat protein to fat ratio, and the like.

In still other embodiments, a composition of the invention may be provided to swine; that is, sows, starter piglets, grower pigs, finisher pigs, and boars. Non-limiting examples of health parameters may include body weight, body condition score, body temperature, food intake, antioxidant status, markers of oxidative stress, serum protein levels, serum mineral levels, immune system function, health and diversity of gut microflora, fecal bacteria, bone and joint health, and the like. Examples of suitable performance parameters may include but are not limited to weight gain, feed:gain ratio, nutrient digestibility, feed conversion ratio, wean to estrus interval, fertility rate, number of offspring, weight of offspring, farrowing rate, days to weaning, carcass quality, carcass yield meat grade, meat yield, meat protein to fat ratio, and the like.

In additional embodiments, a composition of the invention may be provided to horses. Non-limiting examples of health parameters may include body weight, body condition score, body temperature, food intake, antioxidant status, markers of oxidative stress, serum protein levels, serum mineral levels, immune system function, health and diversity of gut microflora, fecal bacteria, bone and joint health, and the like. Non-limiting examples of suitable performance parameters may include weight gain, feed:gain ratio, nutrient digestibility, feed conversion ratio, stride length, jump distance, speed, and the like.

In additional embodiments, a composition of the invention may be provided to aquaculture animals, such as fish, shrimp, oysters, mussels, and the like. Examples of suitable health parameters may include but are not limited to body weight, body condition score, food intake, antioxidant status, markers of oxidative stress, serum protein levels, serum mineral levels, immune system function, health and diversity of gut microflora, fecal bacteria, and so forth. Non-limiting examples of suitable performance parameters may include weight gain, feed:gain ratio, nutrient digestibility, feed conversion ratio, shell quality, carcass quality, carcass yield, meat grade, meat yield, meat protein to fat ratio, and the like.

In still further embodiments, a composition of the invention may be fed to companion animals such as cats, dogs, and the like. Examples of suitable health parameters may include, but are not limited to, body weight, body condition score, food intake, antioxidant status, markers of oxidative stress, serum protein levels, serum mineral levels, immune system function, body temperature, health and diversity of gut microflora, fecal bacteria, bone and joint health, and so forth. Non-limiting examples of suitable performance parameters may include weight gain, feed:gain ratio, nutrient digestibility, feed conversion ratio, mobility, agility, quality of life, and the like.

(c) Methods of Preserving

In other embodiments, the invention encompasses a method of preserving a product. In particular the method comprises adding a composition of the invention to a product to be preserved. This can be done by directly adding the composition of the invention to a product, or by way of feeding the composition of the invention to the source animal for a product. For instance, in one embodiment, a method of the invention encompasses preserving an animal feed or supplement. The method comprises combining the animal feed or supplement with a composition of the invention. In another embodiment, the method comprises contacting the composition of the invention with a product to be preserved.

Suitable amounts include those as detailed in Section IV(a) above.

EXAMPLES

The following examples illustrate various iterations of the invention.

Example 1: Effect on Egg Yolk Color of Layers

A trial was performed with laying hens in cages to compare the pigmenting efficiency of Xamacol 40 ("X-40") in comparison with a composition of the present invention—Xamacol ColorTek ("XCT") on egg yolk color of layers.

The trial lasted 7 weeks, including 3 weeks of xanthophylls depletion feeding the "white" basal diet, followed by 4 weeks of feeding the experimental diets. Animals (168 Isa Brown laying hens, 48 weeks old at the beginning of the trial) were already located in the trial room with the same cage mates from 18 weeks of age. Experimental feeds with pigments were provided after 3 weeks of xanthophylls depletion of birds while feeding the "white" basal diet. Feed and water were provided for ad libitum consumption. The basal diets were formulated to meet or exceed the nutrient requirements of laying hens. A single basal diet was formulated according to the expected feed consumption. Each feeding treatment was prepared from the addition of the corresponding amount of product, in a multi-step mixing schedule, to 100 kg of feed.

There were a total of 7 feeding treatments (including the "white" Control). Feeding treatments arose from the addition to the basal diet of the experimental product at the corresponding dose (Product X-40 or XCT to provide 4, 6 or 9 mg xanthophylls/kg complete feedingstuff), a negative control with no pigment addition was also included in the design.

Performance variables were checked and recorded per replicate every second week while feeding the experimental feeds (body weight, feed consumption, laying rate, egg weigh, incidence of broken, soft shelled or dirty eggs on a daily basis). Egg yolk color was assessed at the end of the xanthophylls depletion phase (−1 d & 0 d), weekly for three weeks (7 d, 14 d, 21 d) and daily during the $4^{th}$ week (24 d to 28 d) except two days when eggs were reserved for xanthophylls analysis (22 d & 23 d). All eggs laid on each single day were taken for egg yolk color assessment or xanthophylls analysis.

Results from the present trial were good according to Isa Brown standards (2010), with 4.7% improvements in laying rate (90.6% vs. 86.6%), 1.6% lower average egg weight (63.6 g vs. 64.6 g), 6.0% improvement in feed conversion ratio (FCR) (1.884 vs. 2.005), and 3% improvement in productivity (57.6 g vs. 55.9 g). The contrast for pigment effect (X-40 vs. XCT) was significant for egg weight (2.3% differences: 62.92 g vs. 64.37 g).

The analysis of eggs from week 4 demonstrated a significant effect of pigment and dose, with significant interactions pigment×dose (indicating that the slopes from the linear regressions were significantly different) for the variables CIE (Commission Internationale de L'Eclairage) a*, ratio CIE a*/b* and Roche Yolk Color Fan (RYCF). For each dose level, pigment XCT had better values than pigment X-40 for the variables CIE b*, ratio CIE a*/b* and RYCF. Lightness was less sensible to differences between pigments or dose. Pigment XCT had 1.6 points higher yellowness value as average (39.84 vs. 38.28) and 2 points higher intercept value. For CIE a*/b* and RYCF variables, pigment XCT 100 was 117% as efficient as pigment X-40. Results from non linear regressions including the values for 0 ppm offered similar conclusions: pigment XCT was 122% as efficient as pigment X-40 for the yellowness value and 118-119% as efficient for the ratio redness/yellowness and RYCF.

Egg yolk weight was not significantly affected by pigment or dose, while xanthophylls content of egg yolk was significantly affected by both factors, with significant or almost significant interactions when expressed as ppm or total content respectively. The interaction meant that the increase in xanthophylls content of egg yolk with dose was higher for pigment XCT: pigment XCT was 137-133% as efficient as pigment X-40. Deposition rate corrected for laying rate was significantly affected by pigment but not by dose (interaction was not significant): pigment XCT had 0.63 points higher deposition rate on average than pigment X-40 (3.28% vs. 2.65%), representing that pigment XCT was 124% as efficient as pigment X-40. Pigment XCT was approximately 119% as efficient as pigment X-40 for coloration of egg yolk, 135% as efficient for xanthophylls content of egg, and 124% as efficient for xanthophylls deposition rate.

Example 2: Effect on Egg Yolk Color of Layers

A trial was performed with laying hens in cages to compare the pigmenting efficiency of different yellow pigments from (X-40, XCT and Competitor Product 3 ("C3")) on egg yolk color of layers.

The trial lasted 9 weeks, including 5 weeks of xanthophylls depletion feeding the "white" basal diet, followed by 4 weeks of feeding the experimental diets. Animals (305 HyLine Brown laying hens, 23 weeks old at the beginning of the trial) were already located in the trial room with the same cage mates from 18 weeks of age. Experimental feeds with pigments were provided after 5 weeks of xanthophylls depletion of birds while feeding the "white" basal diet. Feed and water were provided for ad libitum consumption. The basal diets were formulated to meet or exceed the nutrient requirements of laying hens (Hy-Line, 2009). A single basal diet was formulated according to the expected feed consumption. Each feeding treatment was prepared from the addition of the corresponding amount of product, in a multi-step mixing schedule, to 64 or 74 kg of feed.

There were a total of 16 feeding treatments. Feeding treatments arose from the addition to the basal diet of the experimental products at the corresponding dose (X-40 or XCT to provide 2.5, 5, 10, 20, 40 and 80 mg xanthophylls/kg complete feedingstuff, or C3 to provide 2.5, 5, 10 and 20 mg xanthophylls/kg complete feedingstuff).

Performance variables were checked and recorded per replicate every second week while feeding the experimental feeds (body weight, feed consumption, laying rate, egg weigh, incidence of broken, soft shelled or dirty eggs on a daily basis). Egg yolk color was assessed at the end of the xanthophylls depletion phase (0 d), weekly for three weeks (7 d, 14 d, 21 d) and daily during the $4^{th}$ week (22 d to 28 d) except one day when eggs were reserved for xanthophylls analysis (25 d); xanthophylls analysis was also performed after depletion phase (−1 d). All eggs laid on each single day were taken for egg yolk color assessment or xanthophylls analysis.

No significant differences were detected among treatments, pigments or doses, for body weight (BW) at the beginning or end of the trial, or for the BW change. No significant effect of treatment or interaction treatment× period were detected for any of the performance variables, except for the incidence of unsaleable eggs among treatments, but these differences were not related with pigment or dose.

Egg yolk color after one week of feeding the experimental diets almost reached its final values obtained after four weeks on trial. Significant differences were detected at all weeks among X-40, XCT, and C3 up to 20 ppm and between X-40 and XCT up to 80 ppm, for almost all variables studied; interactions between pigments and doses were also significant denoting a different response among pigments at increasing doses.

Comparison of non linear regressions for all three pigments up to 10 or 20 ppm gave similar results, being XCT and C3 significantly more efficient than X-40 for yellowness (from 121% to 128%, with no differences among XCT and C3: 95% Confidence Limits overlapping), ratio redness/yellowness (for XCT 158% as efficient as X-40; for C3 117% to 120% as efficient as X-40; being XCT more efficient than C3 because 95% Confidence Limits did not overlap) and RYCF value (for XCT 159% to 161% as efficient as X-40; for C3 117% to 120% as efficient as X-40; being XCT more efficient than C3 because 95% Confidence Limits did not overlap). When the whole range of doses (up to 80 ppm) was used for comparison of X-40 and XCT, results were also similar to the ones obtained with lower inclusion levels: XCT was significantly more efficient than X-40 for yellowness (122%), ratio redness/yellowness (165%) and RYCF value (157%); also redness presented regression values with biological sense, being XCT 159% more efficient than X-40.

Egg yolk xanthophylls concentration and content and xanthophylls deposition rate were significantly higher for XCT (i.e. average corrected deposition rate % up to 20 ppm was 3.02, 3.64 and 3.18 for X-40, XCT and C3 respectively; and up to 80 ppm was 2.82 and 3.46 for X-40 and XCT respectively) although significant interactions were detected between pigments and doses for concentration, total content and deposition (either uncorrected or corrected for laying rate) of xanthophylls in egg yolk. Xamacol 40 at 2.5 ppm had the highest deposition rate % as a consequence of the low level of total xanthophylls detected in this diet compared to other pigments and consequently a lower xanthophyll intake, and not as a consequence of a higher concentration of TX in egg yolk. Xamacol 40 had lower deposition rates than other pigments at all doses except at 2.5 ppm. If the average corrected deposition rate % is calculated excluding the value of 2.5 ppm and up to 20 ppm for all pigments the results were 2.52, 3.54 and 3.17 for X-40, XCT and C3 respectively (ratio 100%, 141% and 126%), and up to 80 ppm for X-40 and XCT were 2.48 and 3.36 respectively (ratio 100% and 135%).

Total xanthophyll concentration and content in egg yolk increased at increasing doses of pigments in the diet, and the responses could be adjusted with linear regression. The improvement in efficiency compared with X-40 from the ratio of slopes of linear regressions for all pigments up to 10 ppm was 190% approximately for XCT, while for C3 the improvement did not reach statistical significance. When doses up to 20 ppm were considered, the improvement was 170% approximately for XCT and 147% approximately for C3.

Considering only X-40 and XCT for the whole range of doses (up to 80 ppm) the ratio of slopes indicated an improvement in efficiency on egg xanthophylls content and xanthophyll deposition rate of 125% for XCT.

Xamacol CT was more efficient than X-40. The improvement for color variables varied depending on the variable studied but not on the range of doses included in the comparison (up to 10, 20 or 80 ppm); approximate improvements were: 125% for yellowness, and 160% for ratio redness/yellowness and RYCF. The improvement for total xanthophylls concentration and content in egg yolk was 190% up to dose 10 ppm, 170% up to 20 ppm, and 125% up to 80 ppm. For the average corrected deposition rate % excluding the value of 2.5 ppm the improvement was 137% approximately.

Competitor product 3 was more efficient than X-40. The improvement varied depending on the variable studied but not on the range of doses included in the comparison (up to 10 or 20 ppm) for color variables; approximate improvements were: 125% for yellowness, and 120% for ratio redness/yellowness and RYCF. The improvement for total xanthophylls concentration and content in egg yolk was 139% but not significant up to dose 10 ppm, and 147% up to 20 ppm. For the average corrected deposition rate % excluding the value of 2.5 ppm the improvement was 126% approximately.

Xamacol CT was more efficient than C3. The improvement varied depending on the variable studied but not on the range of doses included in the comparison (up to 10 or 20 ppm) for color variables; approximate improvements were: 134% for ratio redness/yellowness and RYCF. The improvement for total xanthophylls concentration and content in egg yolk was 137% but not significant up to dose 10 ppm, and 117% but not significant up to 20 ppm.

Example 3: Effect on Broiler Chicken Pigmentation

A feeding trial was carried out to compare the pigmenting efficacy of two different yellow pigments from marigold (X-40 and XCT) in broiler chickens pigmentation and performance until 47 days of age. A total of 1,078 Ross 308 1-d old female chicks, from 1 to 47 days of age were used and allocated at random to the experimental treatments. The experimental design was completely randomized with 7 dietary treatments: T1, Basal diet (Negative Control); T2: Basal diet+Product X-40 30 ppm; T3: Basal diet+Product X-40 40 ppm; T4: Basal diet+Product X-40 50 ppm; T5: Basal diet+Product XCT 30 ppm; T6: Basal diet+Product XCT 40 ppm; T7: Basal diet+Product XCT 50 ppm. Treatments were replicated 7 times and were offered during Grower (22 to 35 days of age) and Finisher (36 to 47 days of age) phases. The animals were housed in pens of 22 broilers per pen at stocking density similar to that practiced commercially in the EU (30 kg/m$^2$).

Mash (Starter) and Pelleted (Grower and Finisher) feeds were fed ad libitum, and were based on wheat and soybean meal, with no added growth promoter or veterinary antibiotics. Starter feeds were fed from 0 to 21 days, grower feeds from 22 to 35 days and finisher feeds from 35 to 47 days of age. Paracox vaccine was administered at 4 days by drinking water and coccidiostat was added to the grower diets.

Observations included growth, body weight, feed intake, feed efficiency, EPEF (European Production Efficiency Factor), general health, and percent of mortality and culling. Also, skin pigmentation was measured on carcasses after chilling. Moreover, oxidation of biceps femoris muscle (TBARs Technique) and intestinal histology was evaluated.

The data were analyzed as a completely randomized design by General Lineal Methods (GLM) of Statistical Analysis Software (SAS). Significance was declared when probability P≤0.05, and near significant trend when 0.05<P≤0.10. Performance and skin color parameters were analyzed as 7 independent treatments and as a factorial design excluding the negative treatment. Skin color parameters were also analyzed by linear regression vs the ingested pigment using the GLM procedure of SAS v. 9.0 (SAS, 2002) and by non-linear regression by fitting the data to two different models using the NLIN procedure of SAS v. 9.0 (SAS, 2002).

The health of the animals was considered normal throughout the study, and no adverse events were noted. Performance of the animals was in accordance with trial conditions (broilers raised in floor pens and fed mash/pelleted diets). No significant differences were observed in body weight of animals between treatments, between types of pigment or between the different dosages used at any of the ages studied. As expected, no significant differences in performance were observed from 0 to 21 days, as all animals received a common diet. No significant differences were observed thereafter, between the type of pigments (X-40 vs XCT) or between different dosages tested.

There were 20 deaths/culls (1.86%) between 0 and 21 days, 8 death/culls (0.74%) between 21 and 35 days, and 34 death/culls (3.15%) between 35 and 47 days (Table 10). An unexpected significant effect in mortality during the finisher period (35 to 47 days) was detected due to the type of pigment. No significant differences were observed in mortality between dosages.

Skin pigmentation was measured on foot, breast (in two different areas; 1: axilla, 2: central breast) and thigh in chilled carcasses of broilers at 47 days of age. Taking into account the lack of raw materials supplying natural pigments in the basal diet, there was a clear difference between negative controls and the rest of experimental treatments, and control animals always exhibited the paler colors. Differences between dosages were also detected, and color always got darker with increasing dosages of pigment, regardless the area evaluated.

Differences between pigments were clearly detected by the RCF and the Spectrophotometer in all the evaluated areas. Broilers receiving the pigment XCT exhibited increased Roche levels in foot ($7.0^a$ vs $6.4^b$; P<0.0001), in breast ($7.1^a$ vs $6.5^b$ and $7.9^a$ vs $6.9^b$, for Point 1 and 2, respectively; P<0.0001) and thigh ($6.8^a$ vs $6.2^b$; P<0.0001) than birds fed on the pigment X-40. Also, a* and b* values of breast and thigh of carcasses of pigment XCT birds were always significantly higher than the values for pigment X-40 (1.48 vs 1.14 and 28.09 vs 26.05 for a* and b* in Breast Point 1, respectively; P<0.05; 2.11 vs 1.68 and 33.41 vs 30.27 for a* and b* in Breast Point 2, respectively; P<0.05; 0.90 vs 0.75, P=0.10 and 25.89 vs 24.60, P=0.0002; for a* and b* in Thigh, respectively). The effect of level inclusion of the pigments in the diet was also clear and significant. Roche color fan and a* and b* values increased and L* values decreased in all the areas evaluated as the dosage of pigment augmented.

In general, linear equations differed between pigments, and the slopes of the equations for pigment XCT were higher than the slopes for pigment X-40 for a* value in breast 2 (+25.7%; P<0.001), for b* value in breast (+13.8%; P=0.0655), breast 2 (+27.8%; P<0.0001) and thigh (+8.5%; P=0.0491) and for RCF values in foot (+7.6%; P=0.0384), breast area 2 (+9.8%; P=0.0044) and thigh (+7.1%; P=0.0565). Non-linear color saturation functions were also evaluated, and the K values (pigment concentration needed to achieve half of maximum pigmentation) for pigment X-40 were higher than the K values for pigment XCT.

The effect of treatment on TBARS level in the Biceps femoris muscle of broilers of 47 days of age after 0 and 10 days of refrigerated storage was also evaluated. No significant differences in lipid oxidation of meat samples stored 0 or 10 days at 4° C. were detected between treatments, between the types of pigments (X-40 vs XCT) or between different dosages tested.

The effect of treatment on villus height, crypt depth and muscular layer thickness measured on five GIT sections was also evaluated. No significant differences were detected between the negative control and the other treatments in any of the evaluated histological parameters. In general, no significant differences between pigments were detected in the evaluated areas. There was a clear difference between negative controls and the rest of experimental treatments in skin pigmentation, and control animals always exhibited the paler colors in all the areas evaluated. Differences between pigments were clearly detected by the RCF and the Spectrophotometer in all the evaluated areas. Broilers receiving the pigment XCT exhibited increased Roche levels, a* and b* values than birds fed on the pigment X-40. In general, linear equations differed between pigments, and the slopes of the equations for pigment XCT were higher than the slopes for pigment X-40 for a* value in breast 2 (+25.7%), for b* value in breast (+13.8%), breast 2 (+27.8%) and thigh (+8.5%) and for RCF values in foot (+7.6%), breast area 2 (+9.8%) and thigh (+7.1%). In general, the non-linear color saturation functions differed between pigments, and the K values for pigment X-40 were higher than the K values for pigment XCT.

Example 4: Effect on Broiler Chicken Pigmentation

A trial was performed with broiler chickens in floor pens to compare the pigmenting efficiency of different yellow pigments (X-40, XCT and C3) on broiler coloration.

The trial lasted 6 weeks, including 3 weeks of feeding the "white" basal diet, followed by 3 weeks of feeding the experimental diets. Animals (1223 one day old Ross 308 female broiler chickens) were randomly allocated in 56 pens upon arrival. Experimental feeds with pigments were provided after 3 weeks of feeding the "white" basal diet. Feed and water were provided for ad libitum consumption. The basal diets were formulated to meet or exceed the nutrient requirements of chickens (Ross, 2006). Two basal diets were formulated according birds' age (starter for 3 weeks and grower thereafter). Each feeding treatment was prepared from the addition of the corresponding amount of product, in a multi-step mixing schedule.

There were a total of 10 feeding treatments. Feeding treatments arose from the addition to the basal diet of the experimental products at the corresponding dose (X-40 or XCT provide 20, 40, 60 and 80 mg xanthophylls/kg complete feedingstuff, or C3 to provide 40 mg xanthophylls/kg complete feedingstuff).

Performance variables were checked and recorded per replicate every third week; litter quality was subjectively evaluated at the end of the trial. Broiler coloration was assessed at the slaughterhouse on carcasses cooled for one day.

Neither pigments nor dose affected performance or litter quality.

Xamacol CT reached better coloration than X-40 for lightness of pectoral pterilium (60.65 vs. 61.09), yellowness of axilar apterium (28.78 vs. 28.03), and lightness, redness and ratio redness/yellowness of foot pad (65.60 vs. 66.16, 5.27 vs. 4.36 and 0.11 vs. 0.09 for lightness, redness and ratio redness/yellowness respectively). Differences in other variables were not significant, as well as interactions pigments×dose.

Linear regressions on redness and ratio redness/yellowness of foot pad presented significant differences in intercepts, being XCT 0.9 points higher for redness and 0.02 points higher for ratio redness to yellowness than X-40. Improvement in efficiency measured as the ratio of slopes (for linear regressions) or parameter k (for non linear regressions) ranged from 103% for yellowness of pectoral pterilium and fan color of tarsus, to 109% for fan color of skin, and 120% for redness and ratio redness/yellowness of foot pad. However, none of these improvements reached significance.

Coloration obtained with the competitor (C3) at 40 ppm did not significantly differ from that obtained with X-40 or XCT at 40 ppm for any variable studied but for lightness of foot pad (lower value for C3 than X-40 or XCT; $64.3^d$, $66.4^b$ and $65.8^{bcd}$, respectively) and yellowness of foot pad (lower value for C3 than X-40, not for XCT; $43.6^{de}$, $47.7^c$ and $47.2^{cd}$, respectively).

Coefficients of variation of X-40 were higher compared to XCT for redness of pectoral pterilium and foot pad ($90.3^a$ vs. $78.1^b$; $62.5^a$ vs. $52.2^b$, respectively); however the CV of X-40 was lower compared to XCT for ratio redness/yellowness of foot pad ($0.09^b$ vs. $0.11^a$), but not in other variables. The lowest CV were obtained by fan colors of skin, followed by lightness and yellowness in any location, and fan color of foot pad. Redness and ratio redness/yellowness had much higher CV. The CV obtained in pectoral pterilium, axilar apterium, or foot pad were of similar ranges.

Example 5: Stability Studies

Tests were performed to compare the stability of a composition of the invention containing a free flow agent against X-40. One study measured the reduction in total xanthophylls ("TX") for XCT with a free flow agent in an opened bag at room temperature. Accordingly, the results represent degradation in open bag conditions (exposure to oxygen, moisture, etc). The results are shown in TABLE A. A similar study was conducted at elevated temperatures (50° C.). The results are shown in TABLE B. TABLE C shows the degradation of TX at room temperature for both XCT and X-40 in an oxygen permeable dark bag. TABLE D shows the results of XCT against X-40 where both are mixed with a feed at room temperature in oxygen permeable dark bags. No post-manufacture encapsulation was used for XCT in any of the examples.

TABLE A

Stability of XCT with and without free flow agent (FFA) at room temperature in an oxygen permeable bag.

| Stability (opened bag) at room temp. | 1 month | | 3 months | | 6 months | | 9 months | |
| --- | --- | --- | --- | --- | --- | --- | --- | --- |
| | TX (mg/g) | % stab. | TX (mg/g) | % stab. | TX (mg/g) | % stab. | TX (mg/g) | % stab. |
| XCT without FFA | 88.98 | Quant. | 83.94 | 94% | 81.46 | 96% | 79.36 | 93% |
| XCT with FFA | 74.30 | Quant. | 74.49 | Quant. | 66.23 | 92% | 68.55 | 95% |
| XCT without FFA | 99.15 | Quant. | 91.32 | 92% | 89.65 | 90% | 85.23 | 86% |
| XCT with FFA | 85.51 | Quant. | 77.11 | 90% | 72.86 | 86% | 69.26 | 82% |

TABLE B

Stability of XCT with and without FFA at 50° C. in impermeable bag.

| Stability (closed bag) at 50° C. | 12 weeks | | 18 weeks | | 6 months | | 9 months | |
| --- | --- | --- | --- | --- | --- | --- | --- | --- |
| | TX (mg/g) | % stab. | TX (mg/g) | % stab. | TX (mg/g) | % stab. | TX (mg/g) | % stab. |
| XCT without FFA | 101.6 | Quant. | 97.3 | 98% | 95.0 | 96% | 89.2 | 90% |
| XCT with FFA | 83.7 | 99% | 84.0 | 99% | 80.4 | 95% | 72.9 | 86% |
| XCT without FFA | 94.4 | Quant. | 93.8 | Quant. | 85.7 | Quant. | 81.9 | 96% |
| XCT with FFA | 79.3 | Quant. | 69.8 | 97% | 67.4 | 93% | 65.9 | 91% |

*quant. = no degradation is detected.

TABLE C

Stability of XCT against X-40 at room temperature in an oxygen permeable dark bag.

| Stability (opened bag) at room temp. | 1 month | | 3 months | | 4 months | | 6 months | |
|---|---|---|---|---|---|---|---|---|
| | TX (ppm) | % stab. | TX (ppm) | % stab. | TX (ppm) | % stab. | TX (ppm) | % stab. |
| Xamacol 40 | 26.6 | 62% | 25.4 | 60% | 24.0 | 56% | 20.5 | 48% |
| XCT | 99.0 | Quant. | 99.2 | Quant. | 91.3 | 92% | 89.6 | 90% |

*quant. = no degradation is detected.

TABLE D

Stability of XCT against X-40 mixed with feed at room temperature in oxygen permeable dark bags.

| Stability (opened bag) at room temp. | 1 month | | 3 months | | 4 months | | 6 months | |
|---|---|---|---|---|---|---|---|---|
| | TX (ppm) | % stab. | TX (ppm) | % stab. | TX (ppm) | % stab. | TX (ppm) | % stab. |
| X-40 mixed with Feed | 382 | 96% | 248 | 63% | 192 | 50% | 117 | 30% |
| XCT mixed with Feed | 339 | 93% | 303 | 83% | 270 | 80% | 315 | 87% |

Example 6: Microscopy Comparisons with Xamacol 40

Figure 2A:
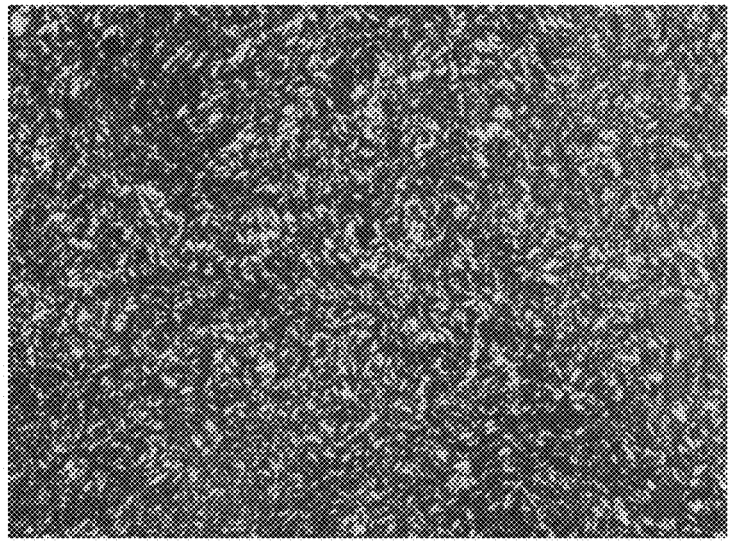
FIGS. 2A-B show the results of polarizing microscopy at 100 magnifications.
Figure 2B:
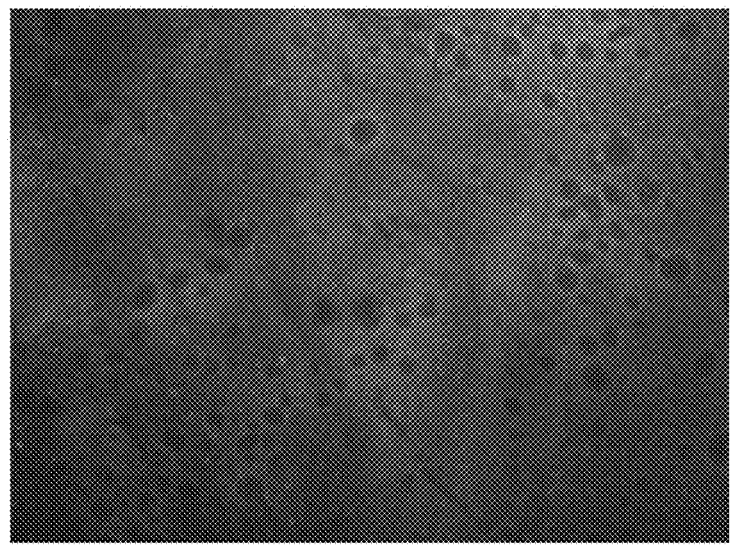
Figure 3A:
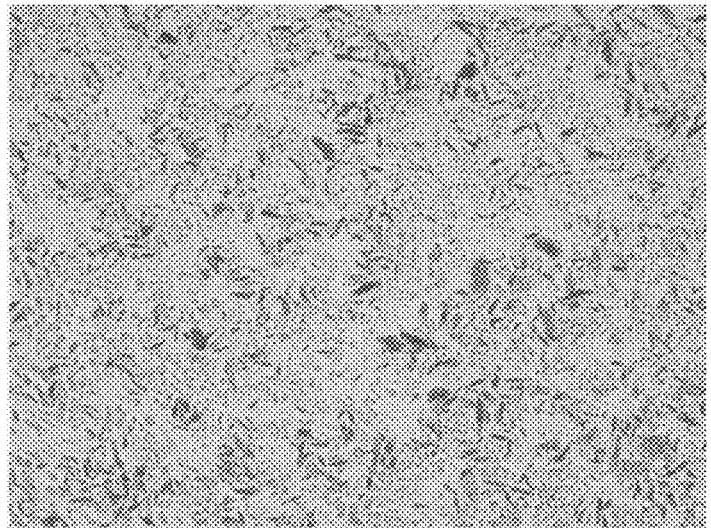
FIGS. 3A-B show the results of optical microscopy at 400 magnifications.
Figure 3B:
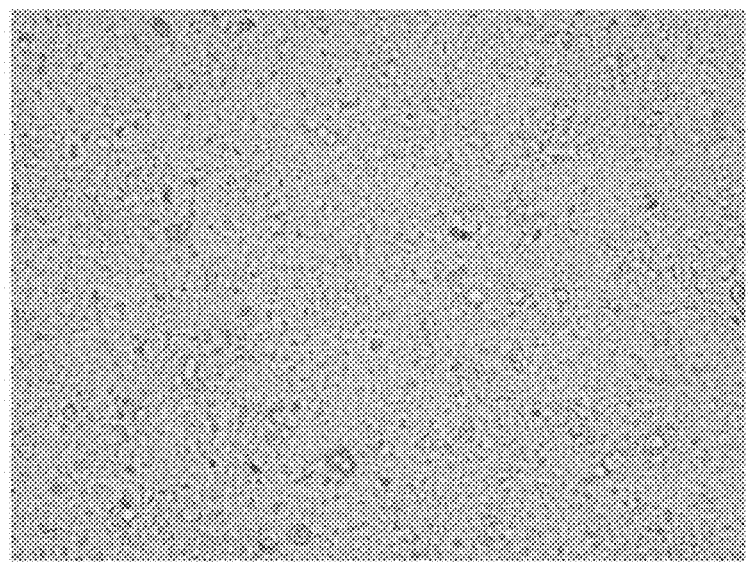

Xamacol ColorTek, (XCT) as prepared as described herein was analyzed by Polarizing and Optical Microscopy. FIG. 2A shows the Xamacol 40 (X-40) soap under Polarizing Microscope at 100 magnifications. FIG. 2B shows XCT under Polarizing Microscope at 100 magnifications. The lutein nano-particles observed in X-40 soap are shown as isotropic material by POM. FIG. 1B shows that the particle size for XCT is too small to be analyzed. FIG. 3A. shows Xamacol 40 under an optical microscope at 400 magn. FIG. 3B shows XCT under an optical microscope at 400 magnifications.

Example 7: Differential Scanning Calorimetry

Figure 4:
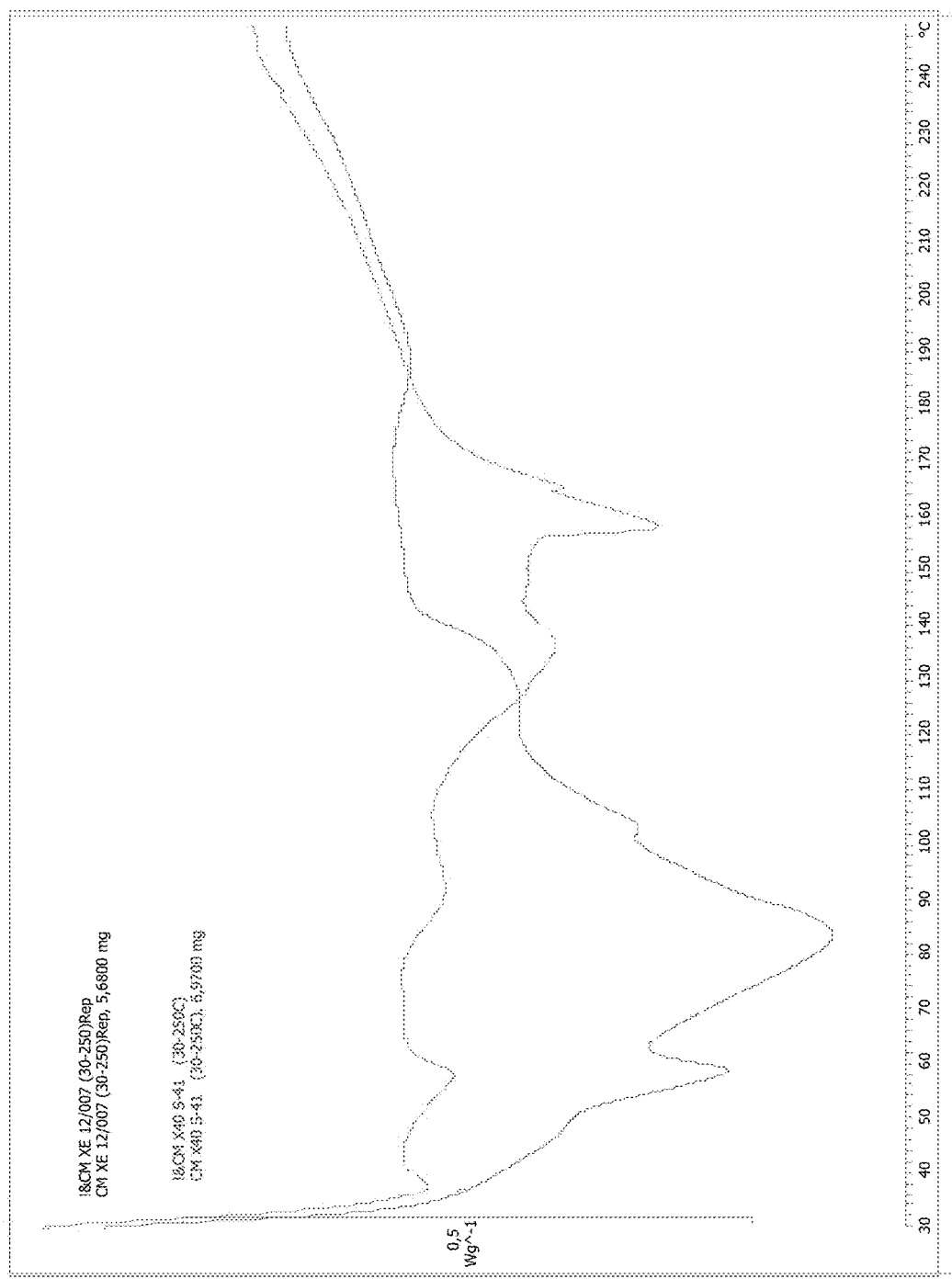
FIG. 4 shows the DSC curves of XCT and X-40.
Figure 5A:
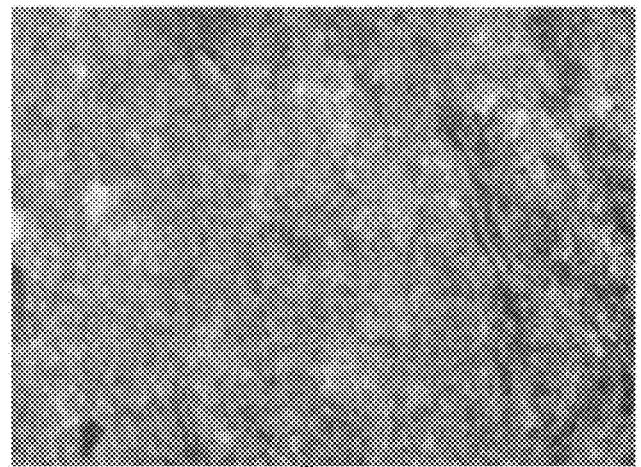
FIG. 5A-D shows melting of X-40.
Figure 5B:
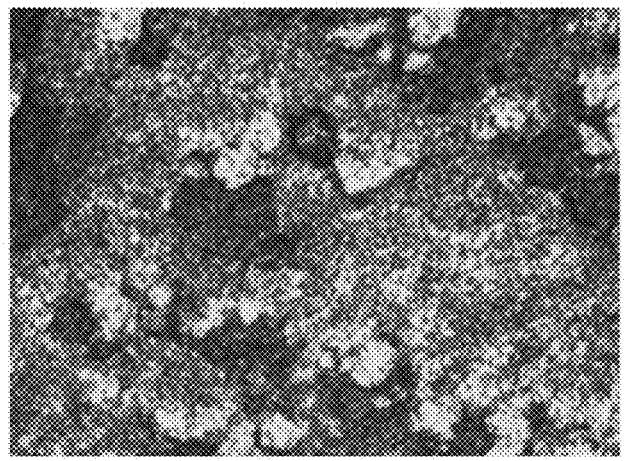
Figure 5C:
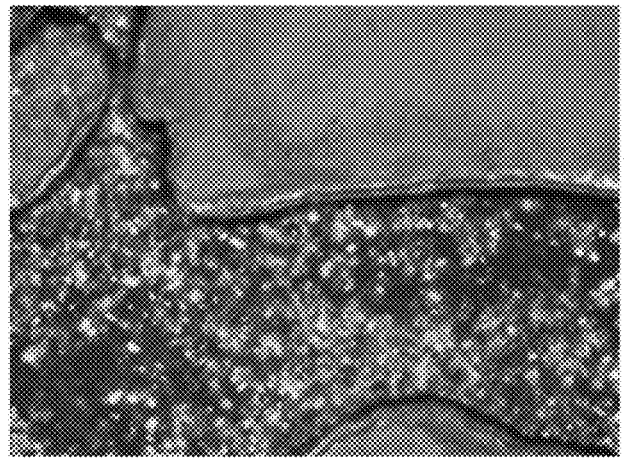
Figure 5D:
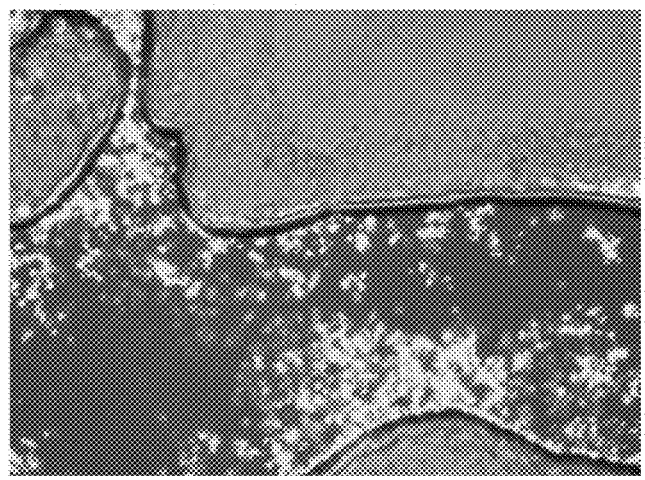

The composition was compared to Xamacol 40 with by Differential Scanning calorimetry at 10° C./min in order to determine the phase transitions. Endothermic processes are shown as negative peaks or valleys and exothermic processes are shown as positive peaks. FIG. 4 shows a red curve for X-40 and a black curve for XCT. In the case of Xamacol 40 soap appears a thin endothermic peak at 158° C. that could correspond with the melting point of lutein crystals.

In order to determine what it is happening in each transition, both samples were observed under a Polarizing Microscope equipped with a heating device with the objective of visualizing the phase transitions in soap samples at different temperatures. The first endothermic valley for both samples was a small melting at 58-60° C. that not produce changes in the soap. After that, a new wide endothermic peak stars (for XCT it starts at 62-64° C. and for X-40 it starts at 78-80° C.). In this process the majority of the soap is melted. This transition is overlapped with another endothermic peak (it starts more or less at 110° C.) that corresponds to the lutein nano-particles melting in both Xamacol 40 and XCT. This process finishes in both cases at 145° C. For XCT no more transitions were observed. For Xamacol 40, a part of the lutein micro-crystals were melted before 150° C. Finally, X-40 sample was heated until 200° C. to study the last endothermic peak. By microscope the melting of lutein micro-crystals was observed more or less at 180-190° C. The last endothermic thin peak corresponds to the melting point of some lutein micro-crystals that belongs to X-40 soap. Part of the lutein micro-crystals melt before 150° C. Lutein nano-particles melt between 110-150° C. or they could be solved by the melted soap. There is an important difference between X-40 soap DSC thermogram and XCT corresponding to the micro-crystals melting at 160-170° C. Wide endothermic peaks may be due to the melting of amorphous particles and narrow endothermic peaks are due to pure crystals melting.

By DSC, the most important difference is between 70-120° C. where XCT has a large endothermic peak and X-40 has a very small one.

After studying the DSC curves, it can be concluded that the saponification of marigold oleoresin to obtain XCT is not performed above the lutein melting point. The main reason crystals are obtained at 70-80° C. is the low soap movement coupled with enough viscosity to allow organization of the lutein molecules. But at 130-140° C., the high movement of soap molecules doesn't allow for crystallization. Photographing the melting of X-40 shows that at 80° C. only lutein crystals (both nano and micro-particles) were observed. At 150° C. only lutein micro-crystals were observed. At 200° C. the melting of the lutein micro-crystals was visualized. Movement at 100° C. makes obtaining a photo difficult. Photos are shown at FIGS. 5A-D.

Example 8: X-Ray Diffraction

Three samples of a composition of the invention (XCT), Xamacol 40 soap and pure lutein were analyzed by X-ray diffraction (XRD) in order to determine the crystallinity of lutein in Xamacol 40 and XCT.

The crystalline part of X-40 presents 4 peaks at 4.44, 6.57, 6.85 and 8.89 (4.44×2). Among the peaks there are two groups. The first can be grouped together as broad peaks (4.44, 6.85 and 8.89°2θ) that correspond to a crystal phase with very small size <30 nm. The sharper peak at 6.57°2θ is due to a crystal particle greater than 150 nm.

The crystalline part of XCT is represented by 2 peaks, 4.69 and 6.96°2θ. The peak at 4.69 is the same as the peak at 4.44 in Xamacol 40. This peak is due to a crystal size lower than 30 nm.

Example 9: Manufacturing Process XCT

A 50% aqueous solution of KOH was added to a reagent container in a continuous flow apparatus. Marigold oleoresin was added to a second reagent container in a continuous flow reactor. The marigold oleoresin was heated to a temperature of 60° C. The KOH solution was pumped into the continuous flow apparatus at a feed rate of about 46 kg/hour. Marigold oleoresin was pumped into the continuous flow reactor at a feed rate of about 154 kg/hour. The KOH was heated through a plates heat exchanger prior to entry into the static mixer. The temperature of the KOH was increased to about 90° C. The KOH and the marigold oleoresin were mixed in a static mixer which was jacketed with a jacket temperature of 140° C. The residence time through the static mixer was about 21 seconds. Prior to entry in another static mixer, the solution was sent through a rotor-stator type homogenizer. After the rotor-stator homogenizer, the solution was passed through a second static mixer which was jacketed with a jacket temperature of 140° C. The residence time in the second static mixer was about 72 seconds. The solution was then passed through a piston flow reactor with a jacket temperature of 140° C. The residence time in the piston flow reactor was about 8 minutes. Following the piston flow reactor, the solution was passed through an atomizer, followed by a dryer. $SiO_2$ was blown onto the atomized product. The product is not encapsulated.

Example 10: Comparative Manufacture for X-40

Figure 6:
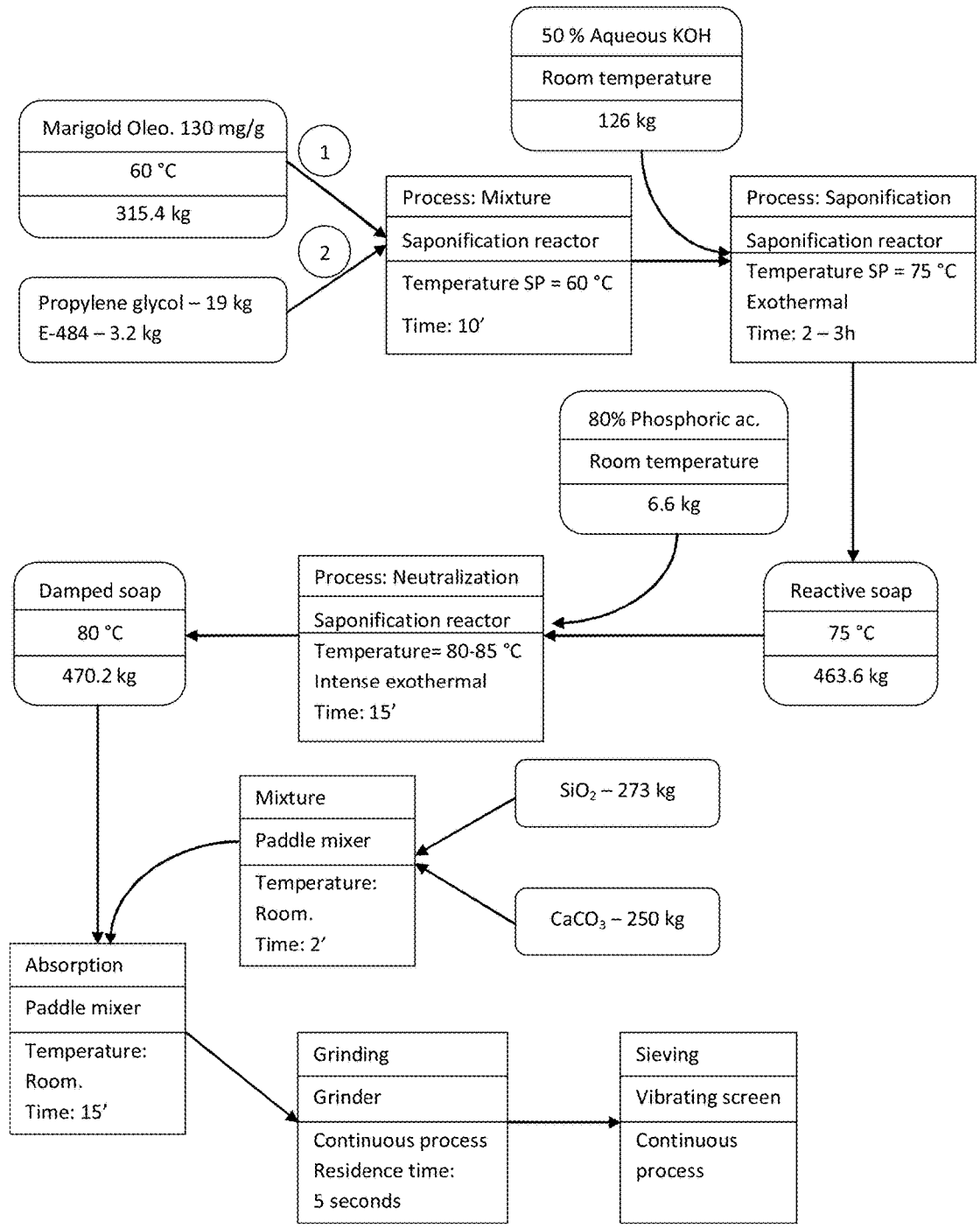
FIG. 6. provides a schematic for a comparative X-40 process.

Marigold oleoreisn, E-484 (glyceryl polyethyleneglycol ricinoleate) and propylene glycol were mixed together inside a saponification reactor. The temperature in the saponification reactor ranged from 58° C. to about 63° C. The time lapse for this step was about 10'. Aqueous sodium hydroxide was then poured into the saponification reactor. The reaction between the marigold oleoresin and the potassium hydroxide was allowed to occur for 2 to 3 hours. The temperature during this time was 75-80° C. Phosphoric acid was then added to the saponification reactor to quench excess potassium hydroxide. The temperature rose from 5 to 10° C. because of the exothermic nature of this reaction. The soap was poured into a paddle mixer loaded with calcium carbonate and silicon dioxide. The soap was adsorbed by the free flow agent. The total time for this is about 20' including loading and mixing. The mixer was discharged and passed through a grinder in order to disaggregate lumps. The product is sieved through a vibrating screen. A schematic is shown in FIG. 6. TABLE E Shows physical properties of the final product prepared by this process and by the process of the invention. The product of this process is referred to as X-40 throughout the application.

TABLE E

Comparison of physical properties between XCT and X-40

| Physical Property | XCT | X-40 |
|---|---|---|
| Bulk aspect | Yellow-brown powder | Orange-yellow fine powder |
| Xanthophyll crystal size | 99% below 0.5 microns | 64% below 0.5 microns |
| Particle aspect | Spheroid to elongated particles | Heterogeneous |
| Particle distribution | 100% <0.85 mm 98% >0.105 mm | 95% <0.85 mm There isn't a specification about the maximum content of very fine particles |
| Particle strength | withstands pressure up to 100 g/cm$^2$ | withstands pressure up to 100 g/cm$^2$ |
| Melting point | Above 90° C. | Does not melt completely |
| Solid excipients | Talc/SiO$_2$ | CaCO$_3$/SiO$_2$ |
| Maximum solid excipients content | Max 12% | 67% |
| Dustiness | 84 | 50.7 |
| Bulk density (g/ml) | 0.44-0.53 | 0.6-0.8 |
| Max. Moisture (%) | 2 | 8 |
| Xanthophyll content (mg/g) | 100.0-104.0 | 40-42 |
| Min. all trans xanthophylls (%) | 82.0 | 88.0 |

Example 11: Stability Study with Ethoxyquin

Compositions of the invention (XCT) were studied with different amounts of ethoxyquin (ETQ). The samples were prepared as described in Example 9. The samples were measured by using a validated analytic method to determine total xanthophylls. Total xanthophylls were analyzed for each sample at the beginning of the study. All samples were stored in an oxygen permeable dark plastic bag at 25° C. All samples were held in the same conditions (darkness, oxygen, temperature, light, and time).

As can be seen in TABLE F, there were no difference between products with different amounts of ethoxyquin. Instead, the compositions manufactured in accordance with the present invention were more stable and had more effect than that produced by the addition of ethoxyquin.

TABLE F

Stability Study with Ethoxyquin

| XCT stability with different ETQ content | Initial | 15 days | | 1 month | | 3 months | | 6 months | | 9 months | |
|---|---|---|---|---|---|---|---|---|---|---|---|
| | | TX | % stab | TX | % stab | TX | % stab | TX | % stab | TX | % stab. |
| XCT (3% ETQ) | 91.96 | 90.1 | 98% | 88.5 | 96% | 81.2 | 88% | 78.6 | 85% | 75.8 | 82% |
| XCT (3% ETQ) | 83.39 | 81.6 | 98% | 80.1 | 96% | 74.3 | 89% | 74.1 | 89% | 73.7 | 88% |
| XCT (0.7% ETQ) | 89.37 | 83.0 | 93% | 84.0 | 94% | 80.8 | 90% | 78.9 | 88% | 78.0 | 87% |
| XCT (ETQ free) | 102.35 | 94.2 | 92% | 91.0 | 89% | 91.6 | 90% | 91.0 | 89% | 91.6 | 89% |
| XCT (ETQ free) | 92.7 | | 0% | 89.8 | 97% | 81.2 | 88% | 75.6 | 82% | 73.8 | 80% |

Example 12: Comparative Stability Study

Several comparative studies were conducted under different temperature conditions, with pure composition or mixed with a vitamin mineral premix. Stability studies were conducted as described in Example 11. The compositions were tested against compositions prepared as described in Example 10 (X-40), competitor 1, and competitor 2. Competitor 2 was so degraded that measurements taken after 30 days were discontinued. The results under different conditions and as mixed with a vitamin premix are shown in TABLES G-I.

TABLE G

Stability Study - Room Temperature, Open Bag

| Room Temperature Open Bag | Initial | TX Initial | 15 days TX | % stab. | 30 days TX | % stab. |
|---|---|---|---|---|---|---|
| XCT | 100.1 | 99.0 | 103.0 | Quant. | 95.9 | 98% |
|  | 98.4 |  | 100.7 |  | 97.9 |  |
|  | 98.5 |  | 101.5 |  | 98.5 |  |
| X-40 | 42.5 | 42.3 | 34.1 | 80% | 29.2 | 70% |
|  | 42.4 |  | 34.0 |  | 29.8 |  |
|  | 41.9 |  | 33.8 |  | 30.0 |  |
| Competitor 1 | 22.5 | 23.2 | 21.5 | 97% | 20.8 | 88% |
|  | 24.5 |  | 23.2 |  | 19.1 |  |
|  | 21.8 |  | 23.0 |  | 21.5 |  |
| Competitor 2 | 18.7 | 19.1 | 13.1 | 65% | 7.4 | 40% |
|  | 19.5 |  | 11.9 |  | 7.5 |  |
|  | 19 |  | 12.1 |  | 7.8 |  |

| Room Temp. Open Bag | 45 days TX | % stab. | 60 days TX | % stab. | 90 days TX | % stab. | 4 months TX | % stab. | 6 months TX | % stab. |
|---|---|---|---|---|---|---|---|---|---|---|
| XCT | 97.6 | Quant | 95.6 | 98% | 97.7 | 97% | 97.5 | 98% | 94.0 | 95% |
|  | 99.4 |  | 96.1 |  | 96.7 |  | 96.8 |  | 94.4 |  |
|  | 99.9 |  | 98.8 |  | 93.8 |  | 95.4 |  | 94.3 |  |
| X-40 | 29.4 | 71% | 29.4 | 70% | 29.3 | 70% | 29.3 | 68% | 29.0 | 69% |
|  | 30.0 |  | 29.7 |  | 29.7 |  | 28.2 |  | 29.0 |  |
|  | 30.4 |  | 30.2 |  | 29.6 |  | 28.3 |  | 29.5 |  |
| Competitor 1 | 22.2 | 92% | 17.1 | 77% | 19.0 | 78% | 17.6 | 79% | 17.5 | 78% |
|  | 20.9 |  | 17.9 |  | 19.2 |  | 19.3 |  | 17.2 |  |
|  | 20.7 |  | 18.3 |  | 16.4 |  | 18.1 |  | 19.4 |  |
| Competitor 2 |  |  |  |  | Discontinued |  |  |  |  |  |

TABLE H

Comparative Stability Study, 45° C., Open Bag

| 45° C. open bag | Initial | TX Initial | 15 days TX | % stab. | 30 days TX | % stab. | 45 days TX | % stab. | 60 days TX | % stab. | 90 days TX | % stab. |
|---|---|---|---|---|---|---|---|---|---|---|---|---|
| XCT | 100.1 | 99.0 | 101.4 | Quant | 100.0 | 98% | 92.2 | 94% | 89.7 | 92% | 86.5 | 87% |
|  | 98.4 |  | 104.2 |  | 96.1 |  | 93.0 |  | 91.7 |  | 86.7 |  |
|  | 98.5 |  | 98.4 |  | 96.2 |  | 94.8 |  | 92.6 |  | 84.1 |  |
| X-40 | 42.5 | 42.3 | 31.4 | 75% | 29.1 | 69% | 27.2 | 65% | 24.8 | 59% | 19.3 | 46% |
|  | 42.4 |  | 31.8 |  | 29.1 |  | 27.4 |  | 25.2 |  | 20.2 |  |
|  | 41.9 |  | 32.5 |  | 29.6 |  | 27.8 |  | 24.3 |  | 19.5 |  |
| Competitor 1 | 22.5 | 23.2 | 19.0 | 82% | 15.4 | 65% | 10.9 | 44% | 9.0 | 39% | 9.6 | 42% |
|  | 24.5 |  | 19.1 |  | 14.6 |  | 9.6 |  | 8.8 |  | 10.0 |  |
|  | 21.8 |  | 18.7 |  | 15.5 |  | 10.2 |  | 9.3 |  | 9.8 |  |
| Competitor 2 | 18.7 | 19.1 | 4.2 | 21% |  |  |  | discontinued |  |  |  |  |
|  | 19.5 |  | 3.9 |  |  |  |  |  |  |  |  |  |
|  | 19 |  | 4.0 |  |  |  |  |  |  |  |  |  |

TABLE I

Comparative Stability Study, 45° C., Open Bag with a Vitamin Mineral Premix

| RT open bag, Vitamin Mineral Premix | Initial | TX Initial | 15 days TX | % stab. | 30 days TX | % stab. |
|---|---|---|---|---|---|---|
| XCT + Vitamin Mineral Premix | 2.1 | 2.08 | 2.0 | 96% | 1.9 | 92% |
|  | 2.1 |  | 2.0 |  | 1.9 |  |
|  | 2.1 |  | 2.0 |  | 1.9 |  |
| X-40 + Vitamin | 2.0 | 1.91 | 1.4 | 70% | 1.3 | 64% |

TABLE I-continued

Comparative Stability Study, 45° C., Open Bag with a Vitamin Mineral Premix

| Mineral Premix | 1.8 | | 1.3 | | 1.2 | |
| --- | --- | --- | --- | --- | --- | --- |
| | 1.9 | | 1.3 | | 1.2 | |
| Competitor 1 + Vitamin Mineral Premix | 3.7 | 3.74 | 3.7 | 99% | 4.0 | Quant. |
| | 3.6 | | 3.5 | | 4.1 | |
| | 3.9 | | 3.9 | | 3.9 | |
| Competitor 2 + Vitamin Mineral Premix | 2.0 | 2.01 | 1.1 | 59% | 0.9 | 44% |
| | 2.1 | | 1.2 | | 0.9 | |
| | 2.0 | | 1.2 | | 0.9 | |

| RT open bag, Vitamin Mineral Premix | 45 days | | 60 days | | 90 days | | 4 months | | 6 months | |
| --- | --- | --- | --- | --- | --- | --- | --- | --- | --- | --- |
| | TX | % stab. | TX | % stab. | TX | % stab. | TX | % stab. | TX | % stab. |
| XCT + Vitamin | 1.8 1.9 | 92% | 1.7 1.8 | 86% | 1.7 1.7 | 80% | 1.8 1.7 | 83% | 1.5 1.5 | 75% |

TABLE I-continued

Comparative Stability Study, 45° C., Open Bag with a Vitamin Mineral Premix

| Competitor 2 + Vitamin Mineral Premix | Discontinued |
| --- | --- |

*quant = no degradation is detected.

Example 13: Closed Bag Stability Studies

Total xanthophylls were studied in closed bag conditions to simulate packing. All samples were manufactured as described in Example 9. The samples (with or without a free flow agent) were stored in impermeable aluminum sealed plastic bag at 25° C. All samples were run under the same conditions of low oxygen content, temperature, and darkness. All formulations showed good stability at 24 months, as shown in TABLE J. The samples had approximately 18% silicon dioxide as a free flow agent (FFA).

TABLE J

Stability of XCT and Silicon Dioxide

| | Initial | 15 days | | 1 month | | 2 months | | 3 months | |
| --- | --- | --- | --- | --- | --- | --- | --- | --- | --- |
| Closed bag with low oxygen | TX (mg/g) | TX (mg/g) | % stab. | TX (mg/g) | % stab. | TX (mg/g) | % stab. | TX (mg/g) | % stab. |
| XCT without FFA | 85.05 | 85.5 | Quant. | 89.0 | Quant. | 81.8 | 96% | 83.9 | 94% |
| XCT with FFA | 72.29 | 73.6 | Quant. | 74.3 | Quant. | 69.9 | 97% | 74.5 | Quant. |
| XCT without FFA | 99.45 | 99.0 | Quant. | 99.1 | Quant. | 99.2 | Quant. | 91.3 | 92% |
| XCT with FFA | 84.53 | 84.6 | Quant. | 85.5 | Quant. | 79.4 | 94% | 77.1 | 90% |

Stability of XCT and Silicon Dioxide in Closed Bag

| | 6 months | | 9 months | | 12 months | | 18 months | | 24 months | |
| --- | --- | --- | --- | --- | --- | --- | --- | --- | --- |
| Closed bag with low oxygen | TX (mg/g) | % stab. | TX (mg/g) | % stab. | TX (mg/g) | % stab. | TX (mg/g) | % stab. | TX (mg/g) | % stab. |
| XCT without FFA | 81.5 | 96% | 79.4 | 93% | 79.5 | 93% | 79.8 | 94% | 74.5 | 88% |
| XCT with FFA | 66.2 | 92% | 68.6 | 95% | 69.1 | 96% | 65.4 | 90% | 63.7 | 88% |
| XCT without FFA | 89.6 | 90% | 85.2 | 86% | 79.5 | 80% | 83.8 | 84% | 78.8 | 79% |
| XCT with FFA | 72.9 | 86% | 69.3 | 82% | 65.7 | 78% | 66.4 | 79% | 65.8 | 78% |

TABLE I-continued

Comparative Stability Study, 45° C., Open Bag with a Vitamin Mineral Premix

| Mineral Premix | 1.9 | | 1.8 | | 1.6 | | 1.7 | | 1.6 | |
| --- | --- | --- | --- | --- | --- | --- | --- | --- | --- | --- |
| X-40 + Vitamin Mineral Premix | | | | | Discontinued | | | | | |
| Competitor 1 + Vitamin Mineral Premix | 3.3 3.5 3.4 | 90% | 3.0 2.6 3.2 | 77% | 2.4 2.7 2.5 | 68% | 2.6 2.7 2.9 | 74% | 2.5 2.5 2.6 | 67% |

Example 14: Powder Formulation

The below represents an Exemplary powder formulation for the XCT process expressed as percent weight.

TABLE K

Exemplary Powder Formulation

| XCT | Composition |
| --- | --- |
| marigold soap | 75%-95% |
| SiO$_2$ | 0%-5% |
| Talc | 2%-10% |
| Stearic acid | 0%-7% |

TABLE K-continued

| Exemplary Powder Formulation | |
|---|---|
| XCT | Composition |
| moisture | 0.3%-1% |
| ETQ | 0.6% |

Example 15: Ethoxyquin-free formulation

The below represents and Exemplary powder formulation without ethoxyquin for the XCT process.

TABLE L

| Exemplary Powder Formulation without Antioxidant | |
|---|---|
| XCT powder ETQ free | Composition |
| marigold soap | 76%-95% |
| SiO$_2$ | 0%-5% |
| Talc | 2%-10% |
| Stearic acid | 0%-8% |
| KOH | 0.1%-1% |
| moisture | 0.3%-1% |

Example 16: Liquid Formulation

Liquid formulations are made in a similar fashion to powder formulations. However, instead of the marigold soap being sprayed into an atomizer, it was sprayed into water. The water was maintained at 15-30° C. With the addition of soap the temperature was increased to 40-50° C. The mixture was mixed over the course of one hour with an ultraturrax. The liquid product was heated at 70-80° C. for 6-9 hours to achieve isomerization to the desired levels of trans lutein and trans-zeaxanthin. After cooling the liquid product is finished.

TABLE M

| Exemplary Liquid Formulation | |
|---|---|
| XCT liquid | Composition |
| marigold soap | 12%-17% |
| ETQ | 0.6% |

TABLE M-continued

| Exemplary Liquid Formulation | |
|---|---|
| XCT liquid | Composition |
| E-484 | 1% |
| Water | 82%-87% |

Example 17: Stability Studies with Liquid Formulation

The liquid formulation is a stable emulsion of marigold soap in water. The stability of a liquid formulation, the stability is mainly due to low contact with oxygen. The results are shown in TABLE N.

TABLE N

| Stability Study with Liquid Formulations | | | | | | | |
|---|---|---|---|---|---|---|---|
| | Initial | 3 months | | 6 months | | 12 months | |
| Stability at RT | TX (mg/g) | TX (mg/g) | % stab. | TX (mg/g) | % stab. | TX (mg/g) | % stab. |
| Xamacol 15 (X-40 in liquid) | 15.7 | — | — | 16.4 | Quant. | 16.3 | Quant. |
| XCT 12/006 liquid pH 12.5 | 16 | 16.4 | Quant. | 15.4 | 96% | 16.3 | Quant. |
| XCT 12/006 liquid pH 13 | 15.9 | 15.9 | Quant. | 17.5 | Quant. | 15.8 | 99% |

*quant = no degradation is detected.

Example 18: Comparative Studies Against Products

Figure 7A:
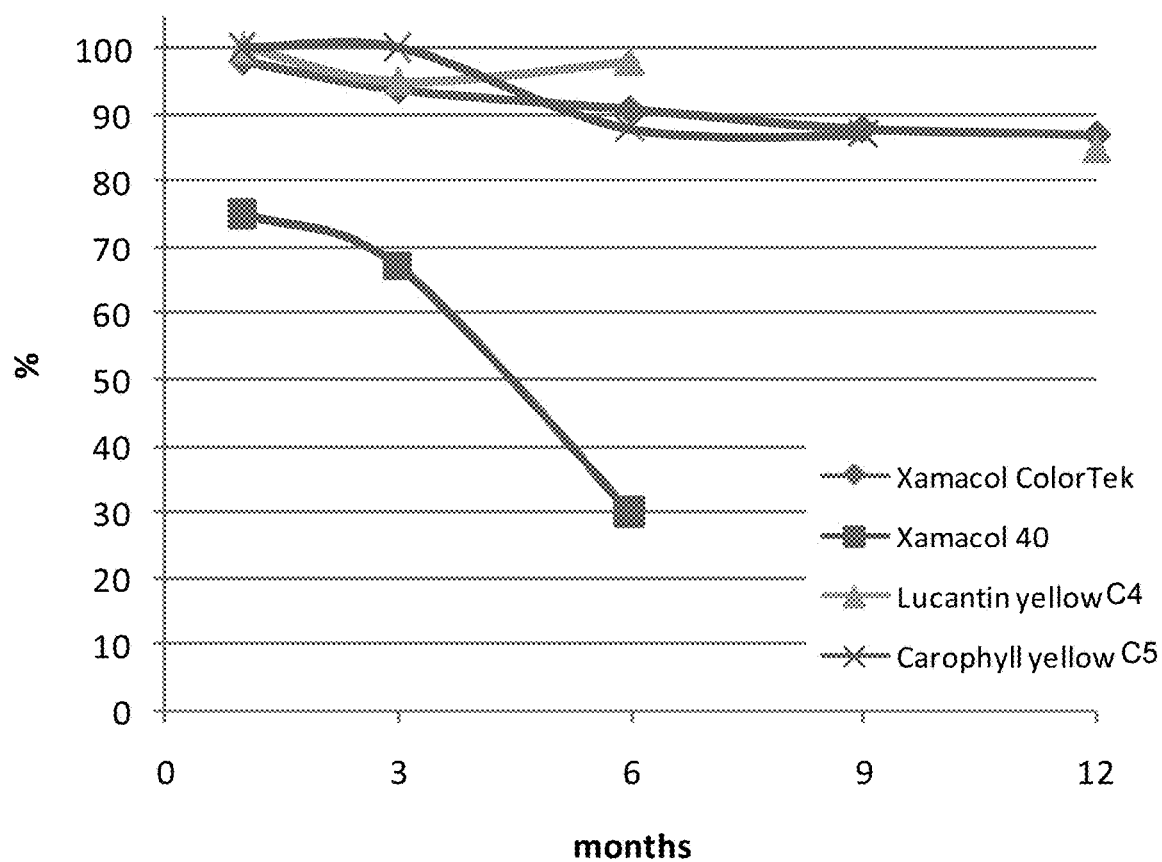
FIGS. 7A-B shows comparative stability studies between XCT, X-40, Competitor Product 3, Competitor Product 4, Competitor Product 5, and Competitor Product 6.
Figure 7B:
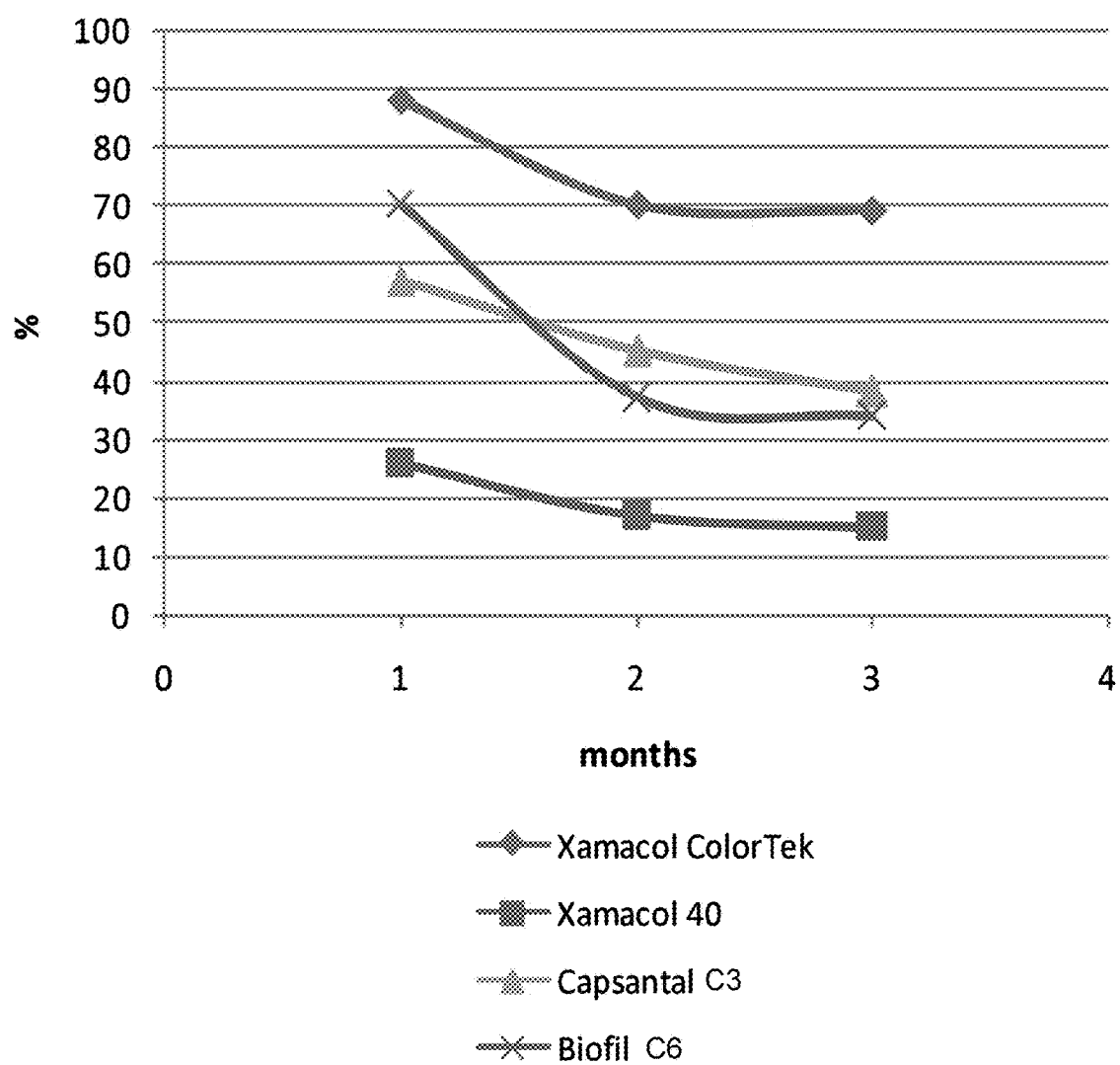
Figure 8A:
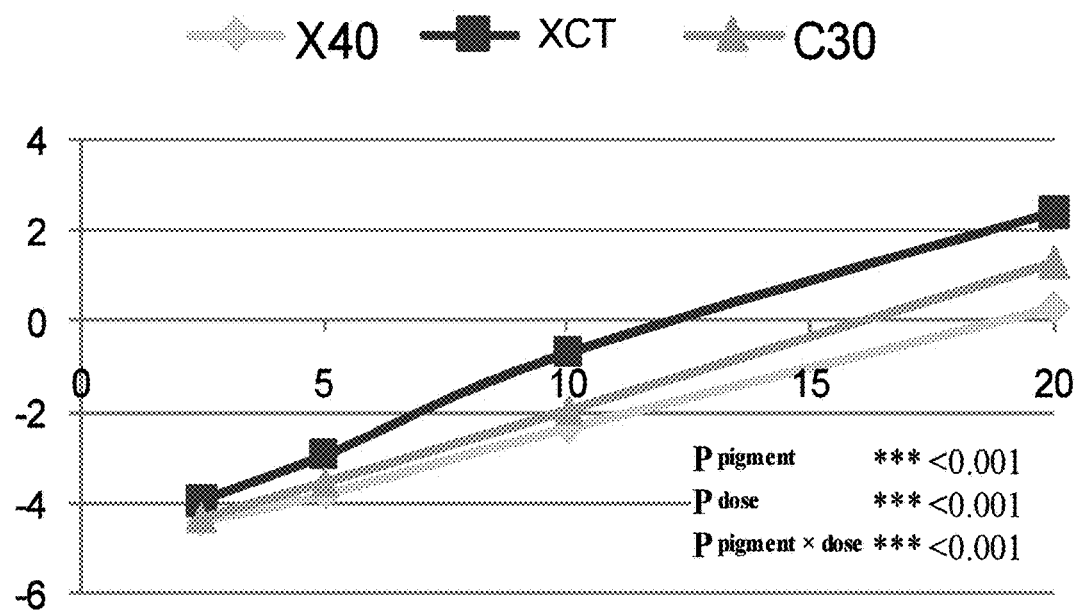
FIGS. 8A-D show the results of Minolta color analysis and DSM/Roche color fan for studies where no red pigment is added against alternative products.
Figure 8B:
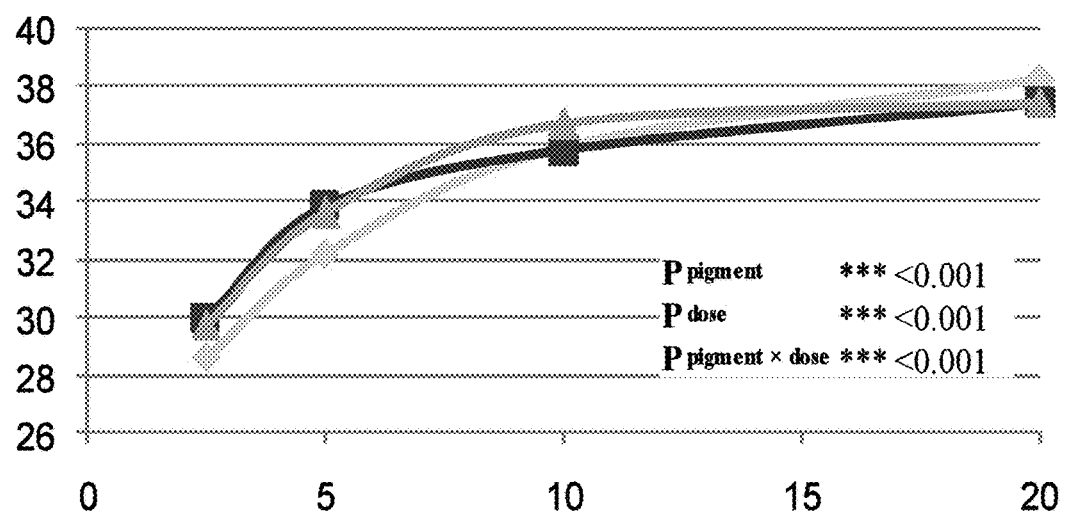
Figure 8C:
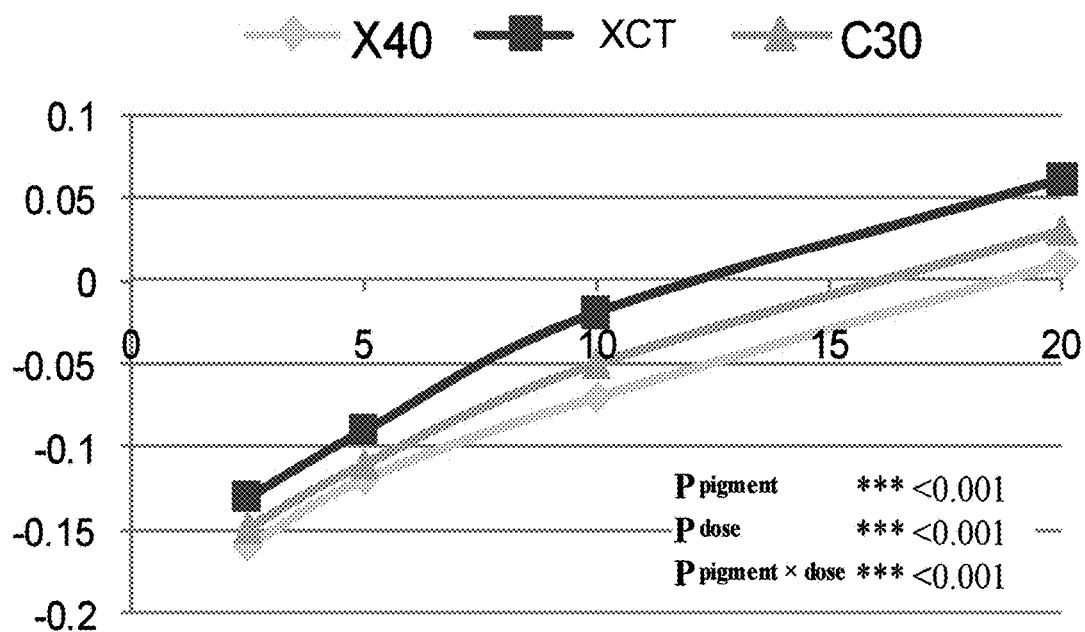
Figure 8D:
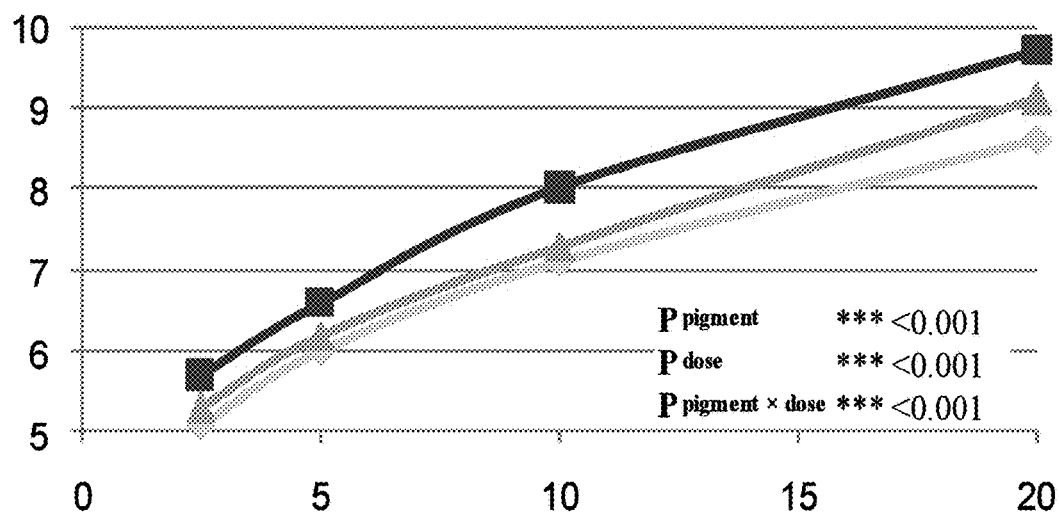

Stability studies were conducted as described in Examples 5 and 11 and compared to apo-ester products. The below table provides the results of these studies against Competitor 4 (C4) and Competitor 5 (C5). For the apo-ester column. Where two values are present, the first is C4 and the second is C5. FIG. 7A shows the results against C4 and C5. FIG. 7B shows the results against C3 and C6.

TABLE O

| Comparitive Study With Apo Ester | | | | |
|---|---|---|---|---|
| Storage conditions | Time (months) | XCT % | X40 % | Apo-ester %* |
| Open bag | 25° C. | 1 | 98 | 75 | 100-100 |
| | | 3 | 94 | 67 | 95-100 |
| | | 6 | 91 | 30 | 98-88 |
| | | 9 | 88 | — | 87 (C5) |
| | | 12 | 87 | — | 85 (C4) |
| Open bag - ETQ low | 25° C. | 6 | 92.5 | — | 90-98 |
| Open bag - ETQ free | 25° C. | 6 | 87.5 | — | — |
| Open bag | 50° C. | 6 | 94 | 67 | 90-95 |
| Open bag | 75° C. | 48 h | 100 | 55 | 100 (C4) |
| In vitamin premix - open bag | 25° C. | 3 | 76 | — | 81-96 |
| | 25° C. | 3 | 69 | 15 | — |
| In feed - open bag | 25° C. | 3 | 97.5 | 60-65 | 100-100 |
| | 45° C. | 1 | 100 | — | 100-100 |
| Closed bag | 25° C. | 12 | 100 | 100 | 100 (C4) |

Example 19: Yellow Pigments of Egg Yolk Color of Layers

A trial was performed with laying hens in cages to compare the pigmenting efficiency of different yellow pigments (A, B and C) on egg yolk color of layers. The trial lasted 9 weeks, including 5 weeks of xanthophylls depletion feeding the "white" basal diet, followed by 4 weeks of feeding the experimental diets.

Animals: 305 HyLine Brown laying hens, 23 weeks old at the beginning of the trial.

Feed and water were provided for ad libitum consumption. The basal diets were formulated to meet or exceed the nutrient requirements of laying hens (Hy-Line, 2009). A single basal diet was formulated according to the expected feed consumption. Each feeding treatment was prepared from the addition of the corresponding amount of product.

There were a total of 16 feeding treatments (6 replicates of 3 hens/cage per treatment). Feeding treatments arose from the addition to the basal diet of the experimental products at the corresponding dose (Product A or B to provide 2.5, 5, 10, 20, 40 and 80 mg xanthophylls/kg complete feedingstuff, or Product C to provide 2.5, 5, 10 and 20 mg xanthophylls/kg complete feedingstuff).

Performance variables were checked and recorded per replicate every second week while feeding the experimental feeds (body weight, feed consumption, laying rate, egg weigh, incidence of broken, soft shelled or dirty eggs on a daily basis). Egg yolk color was assessed at the end of the xanthophylls depletion phase (0 d), weekly for three weeks (7 d, 14 d, 21 d) and daily during the 4th week (22 d to 28 d) except one day when eggs were reserved for xanthophylls analysis (25 d); xanthophylls analysis was also performed after depletion phase (−1 d). All eggs laid on each single day were taken for egg yolk color assessment or xanthophylls analysis.

Assessment of the color was done using a Minolta colorimeter. The colorimeter describes color in the CIE L*a*b* L* indicates the lightness representing dark to light on a scale of (0-100). The a* (redness) value gives the degree of the red-green color with a higher positive a* value indicating more red color. The b* (yellowness) value indicates the degree of yellow-blue color with a higher positive b* value indicating more yellow color. Results are shown in FIGS. 8A-8D. Linear regression on the variables for all pigment doses up to 20 ppm, and during the fourth week of the experimental diets showed that XCT was 121% as efficient as X-40 for yellowness. XCT was 159% as efficient as X-40 for the RYCF.

Figure 9A:
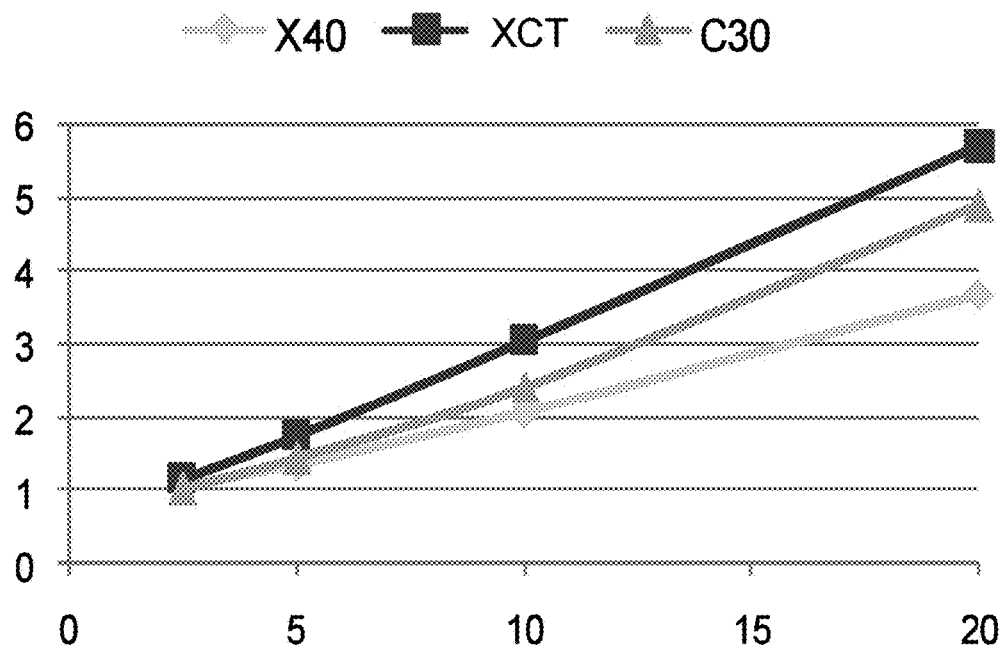
FIGS. 9A-B show the total xanthopylls in egg when XCT is administered against alternative products.
Figure 9B:
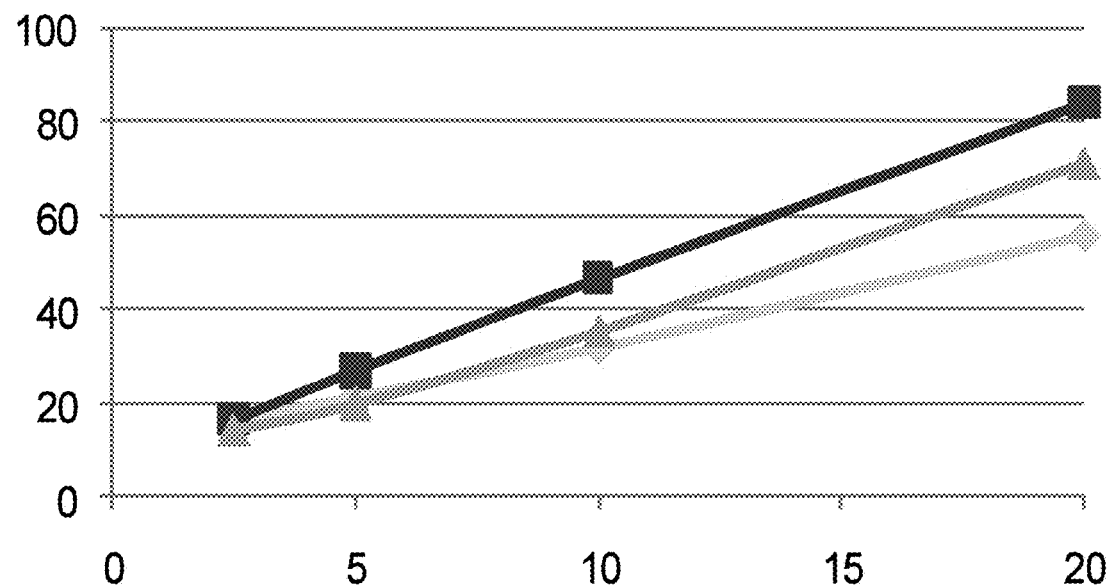
Figure 10A:
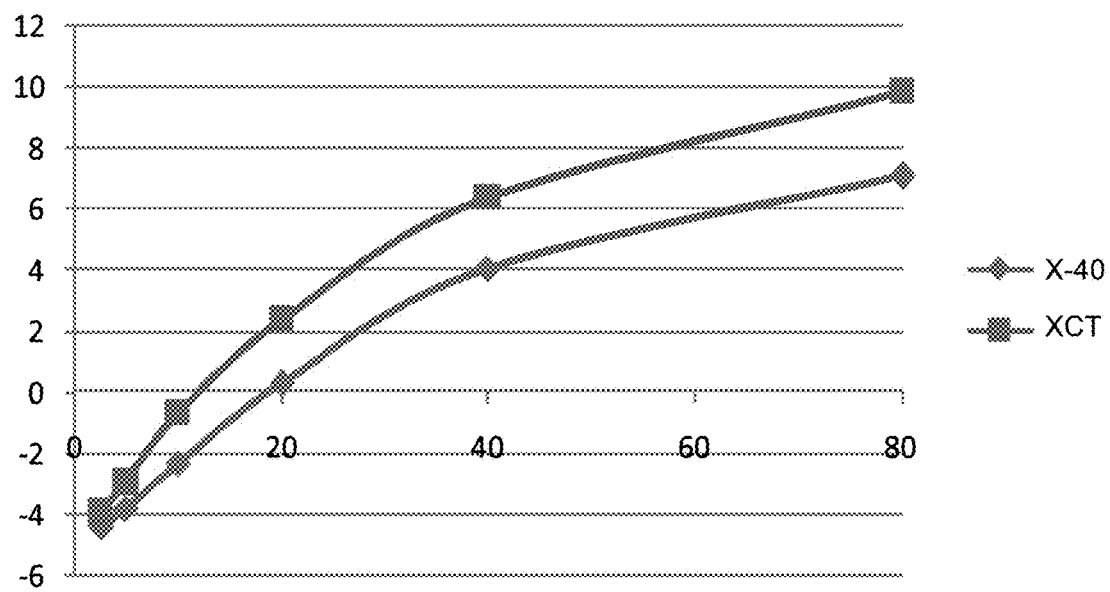
FIGS. 10A-D show the results of Minolta color analysis and DSM/Roche color fan for studies where no red pigment is added against alternative products.
Figure 10B:
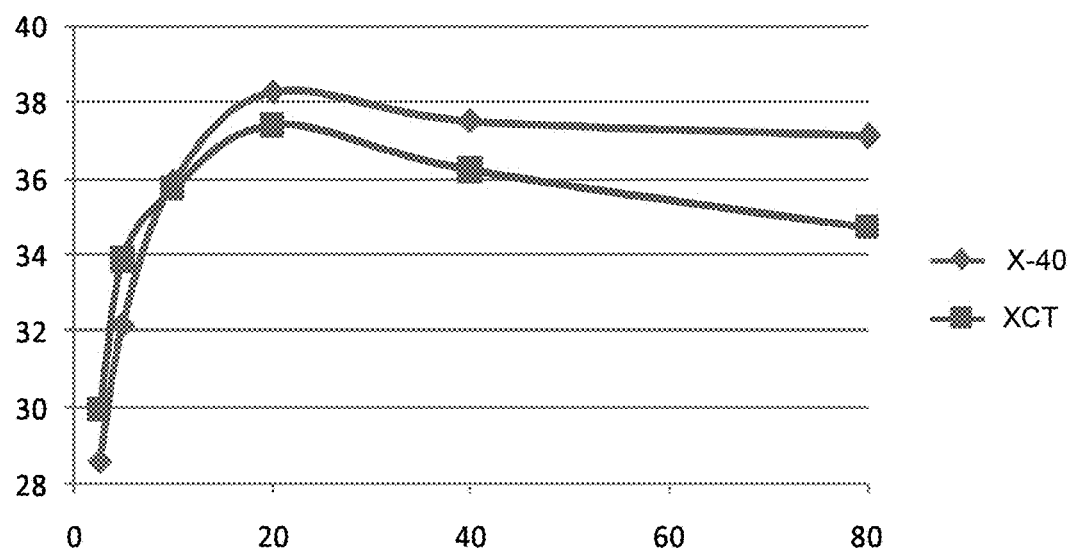
Figure 10C:
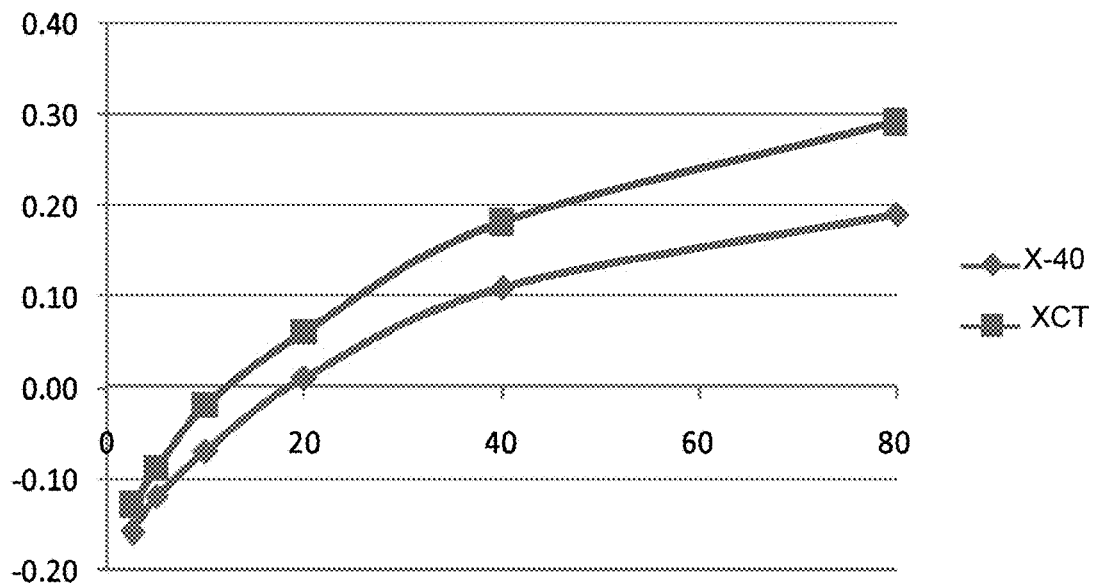
Figure 10D:
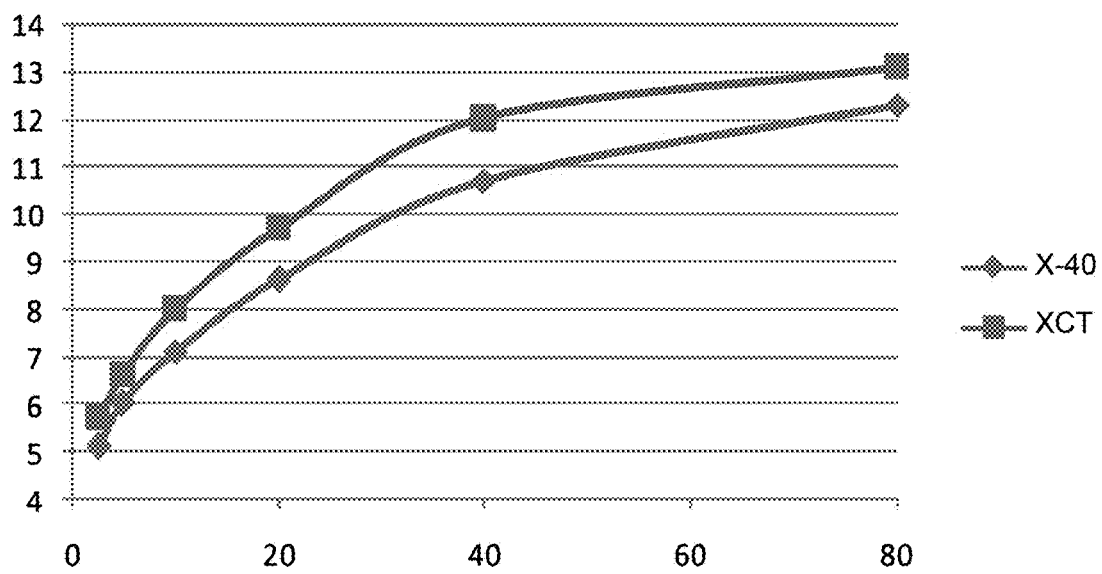

Total xanthophyll content of the egg yolks is shown in FIGS. 9A and 9B. Linear regression analysis shows that at day 25, XCT was 172% as efficient as X-40 for egg xanthophylls concentration.

Example 20: Layer Trials with No Red Pigment Added

A trial was performed with laying hens in cages to determine the comparative efficacy of Xamacol ColorTek vs. apoester (C4) in imparting yellow color to egg yolk.

The trial lasted 9 weeks, including 5 weeks of xanthophylls depletion feeding the "white" basal diet, followed by 4 weeks of feeding the experimental diets.

Animals: 216 Hy-line W-36 laying hens, 57 weeks old at the beginning of the trial.

This study was conducted at MRP battery facility. The house was environmentally controlled. Feed and water were provided for ad libitum consumption. All rations were designed to meet or exceed all dietary recommendations for W-36 (based on Hy-line guide 2009-11).

There were a total of 9 treatments with 24 pen (cage) replicates per treatment. Each cage had one hen. TABLE P shows the treatments.

TABLE P

| Treatments | Description |
|---|---|
| 1 | T1: "0" pigment supplementation (control) |
| 2 | T2: 2 ppm XCT |
| 3 | T3: 4 ppm XCT |
| 4 | T4: 6 ppm XCT |
| 5 | T5: 9 ppm XCT |
| 6 | T6: 12 ppm XCT |
| 7 | T7: 2 ppm of Apo-ester (C4) |
| 8 | T8: 4 ppm Apo-ester (C4) |
| 9 | T9: 6 ppm Apo-ester (C4) |

Results are shown in FIGS. 10A-10D. Linear regression on the variables for all pigment doses up to 80 ppm, and during the fourth week of the experimental diets showed that XCT was 159% as efficient for redness value than X-40, that XCT was 122% for yellowness value as X-40, XCT was 165% as efficient as X-40 for the ratio of redness/yellowness, that XCT was 157% as efficient as X-40 for RYCF.

Figure 11A:
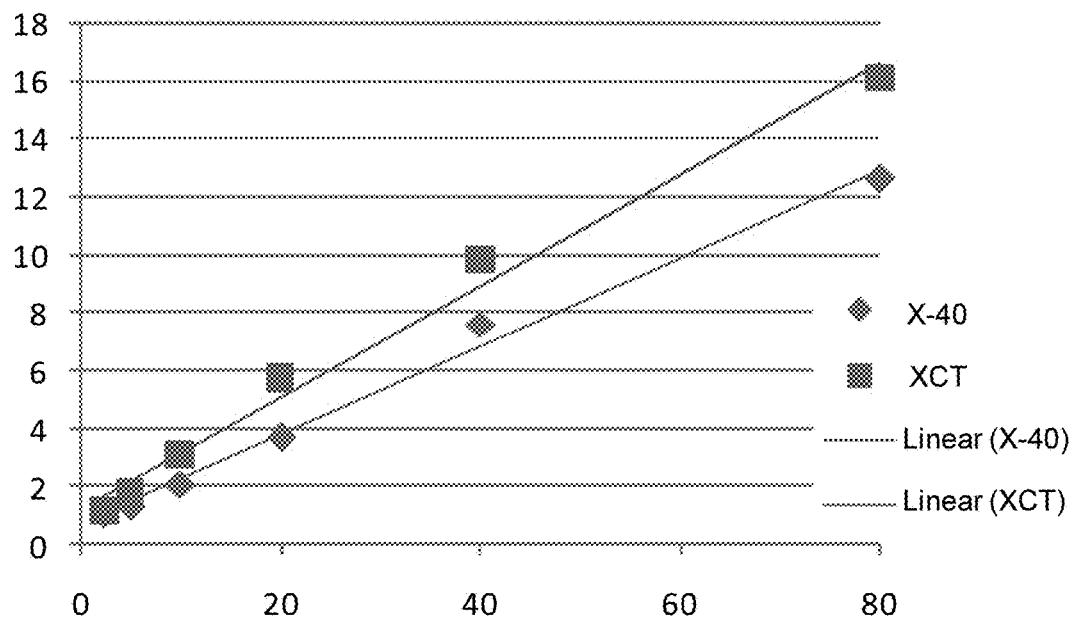
FIGS. 11A-B show the total xanthopylls in egg when XCT is administered against alternative products.
Figure 11B:
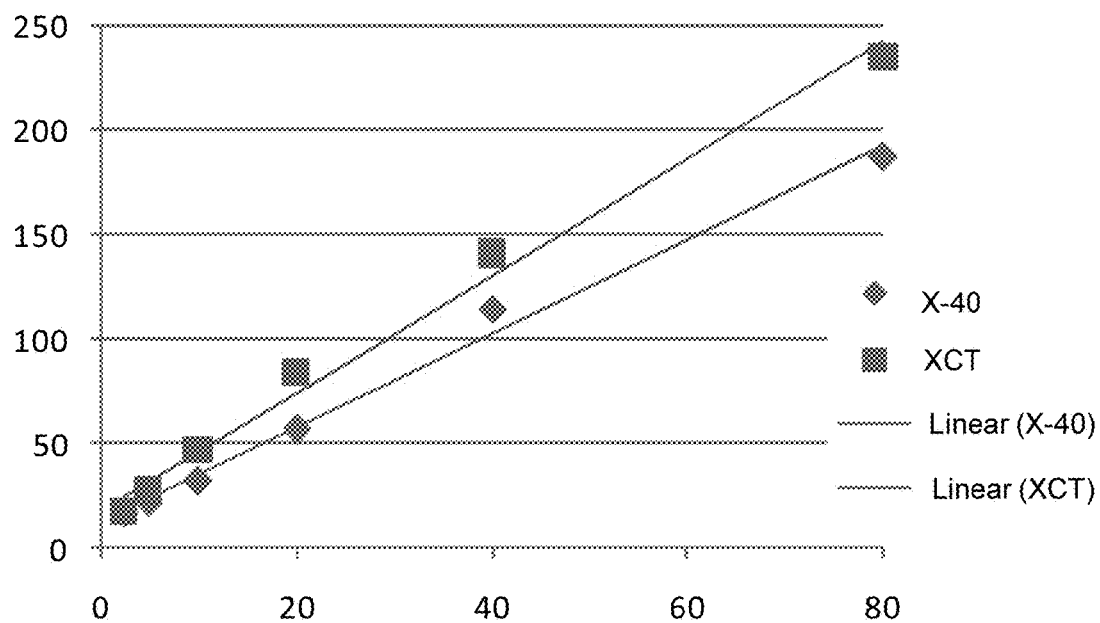
Figure 12A:
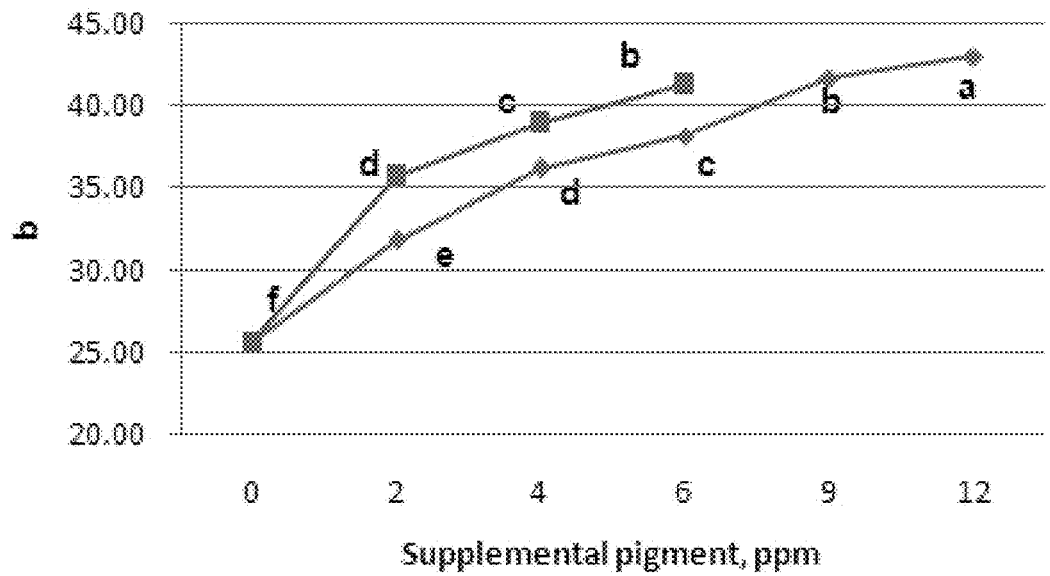
FIG. 12A-D show the total xanthopylls in egg when XCT is administered against apo-ester (β-apo-8'-carotenoic acid ethyl ester).
Figure 12B:
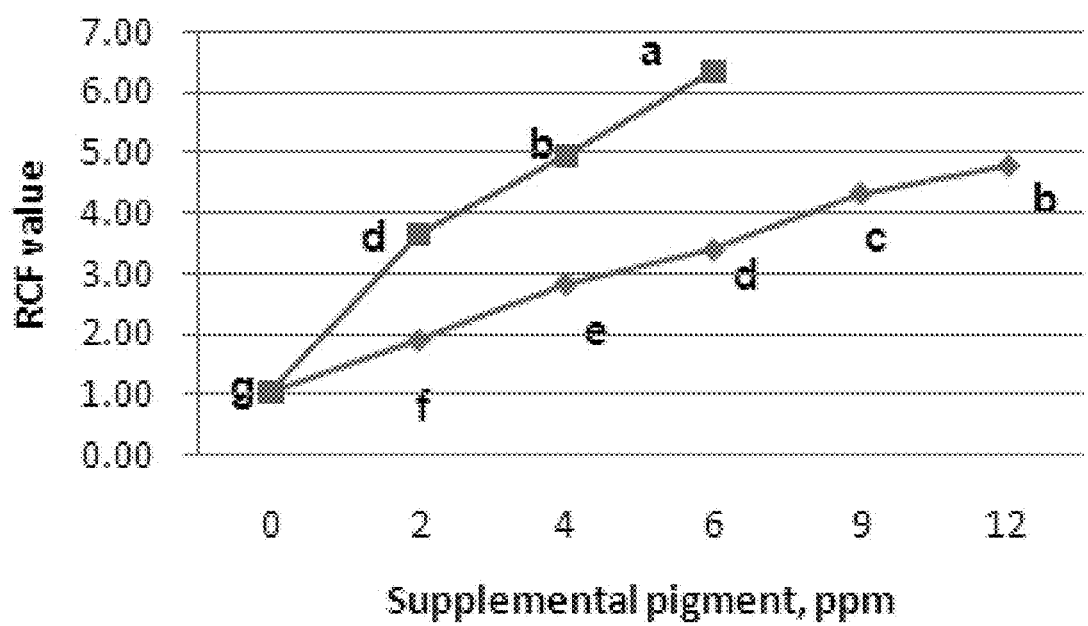
Figure 12C:
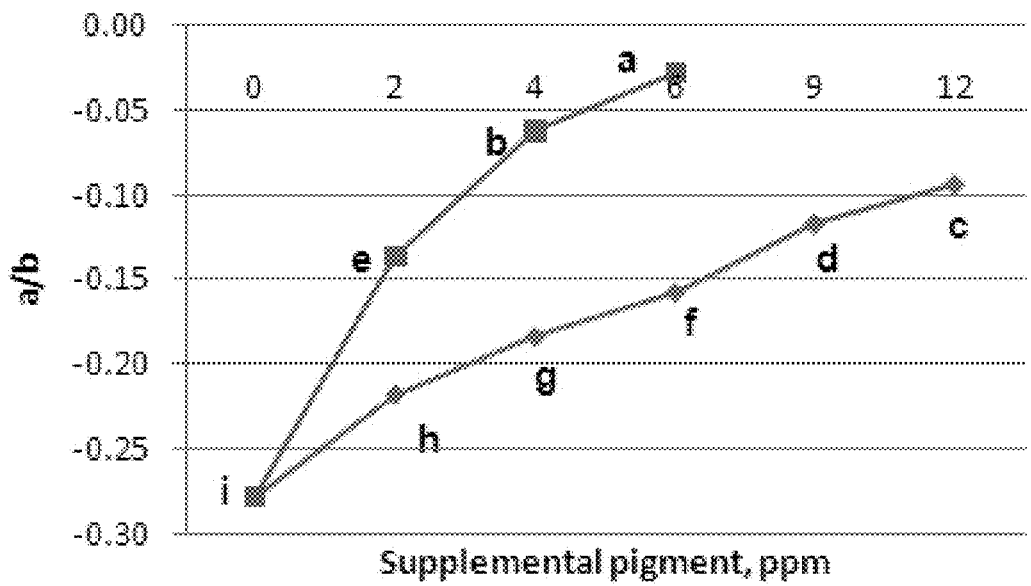
Figure 12D:
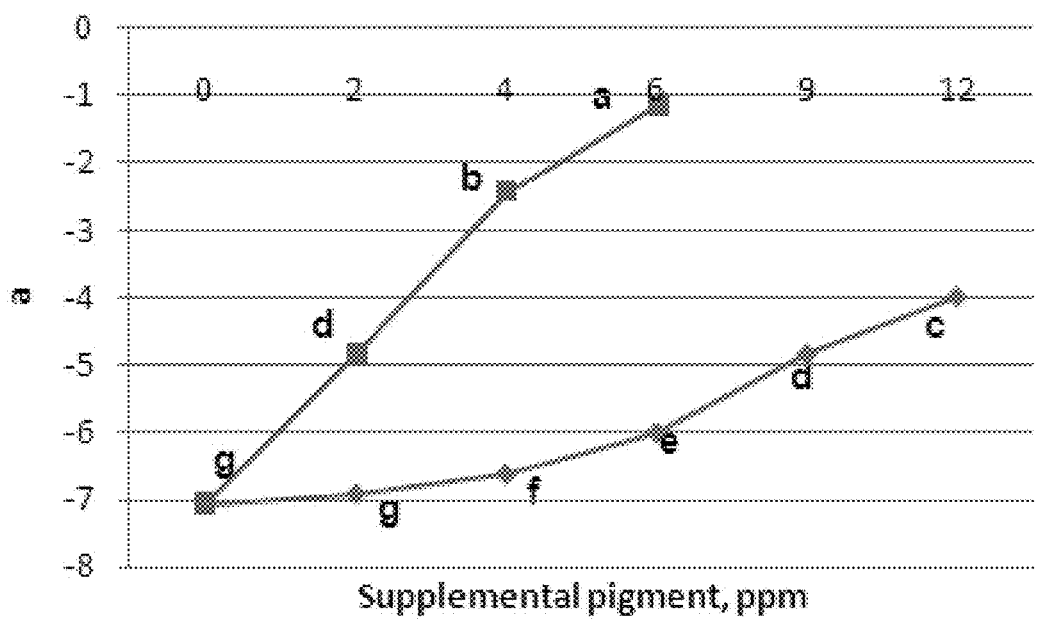

Total xanthophyll content is shown in FIGS. 11A-11B. Linear regression of egg xanthophyll content and xanthophyll deposition rate showed that XCT was 126% as efficient as X-40 of egg xanthophyll concentration, and XCT was 124% as efficient as X-40 for egg xanthophyll content. XCT was 131% more efficient than competitor product 3 in redness/yellowness ratio, 133% more efficient than competitor product 3 for RYCF, and 117% more efficient than competitor product 3 for total xanthophylls in egg yolk.

Similar comparisons were made with Ester products. Results are shown in FIGS. 12A-12D.

Example 21: Layer Trials with Synthetic Red Pigment Added

A trial was performed with laying hens in cages to compare the pigmenting efficiency of 2 yellow pigments (A and B) when red pigment from synthetic origin (C) was added on egg yolk color of layers.

The trial lasted 7 weeks, including 3 weeks of xanthophylls depletion feeding the "white" basal diet, followed by 4 weeks of feeding the experimental diets.

Animals: 360 Hy-line (Isa brown plus), 32 wk old at the beginning of the trial.

Feed and water were provided for ad libitum consumption. The basal diets were formulated to meet or exceed the nutrient Hy-line 2009 requirements of laying hens (Isa Brown, 2009-10). A single basal diet was formulated according to the expected feed consumption. Each feeding treatment was prepared from the addition of the corresponding amount of product.

There were a total of 10 feeding treatments (6 replicates of 6 hens/cage per treatment).

Performance variables were checked and recorded per replicate every second week while feeding the experimental feeds (body weight, feed consumption, laying rate, egg weigh, incidence of broken, soft shelled or dirty eggs on a daily basis). Egg yolk color was assessed at the end of the xanthophylls depletion phase (0 d), weekly for three weeks (7 d, 14 d, 21 d) and more frequently during the 4th week (25 d to 28 d). All eggs laid on each single day were taken for egg yolk color assessment.

Figure 13:
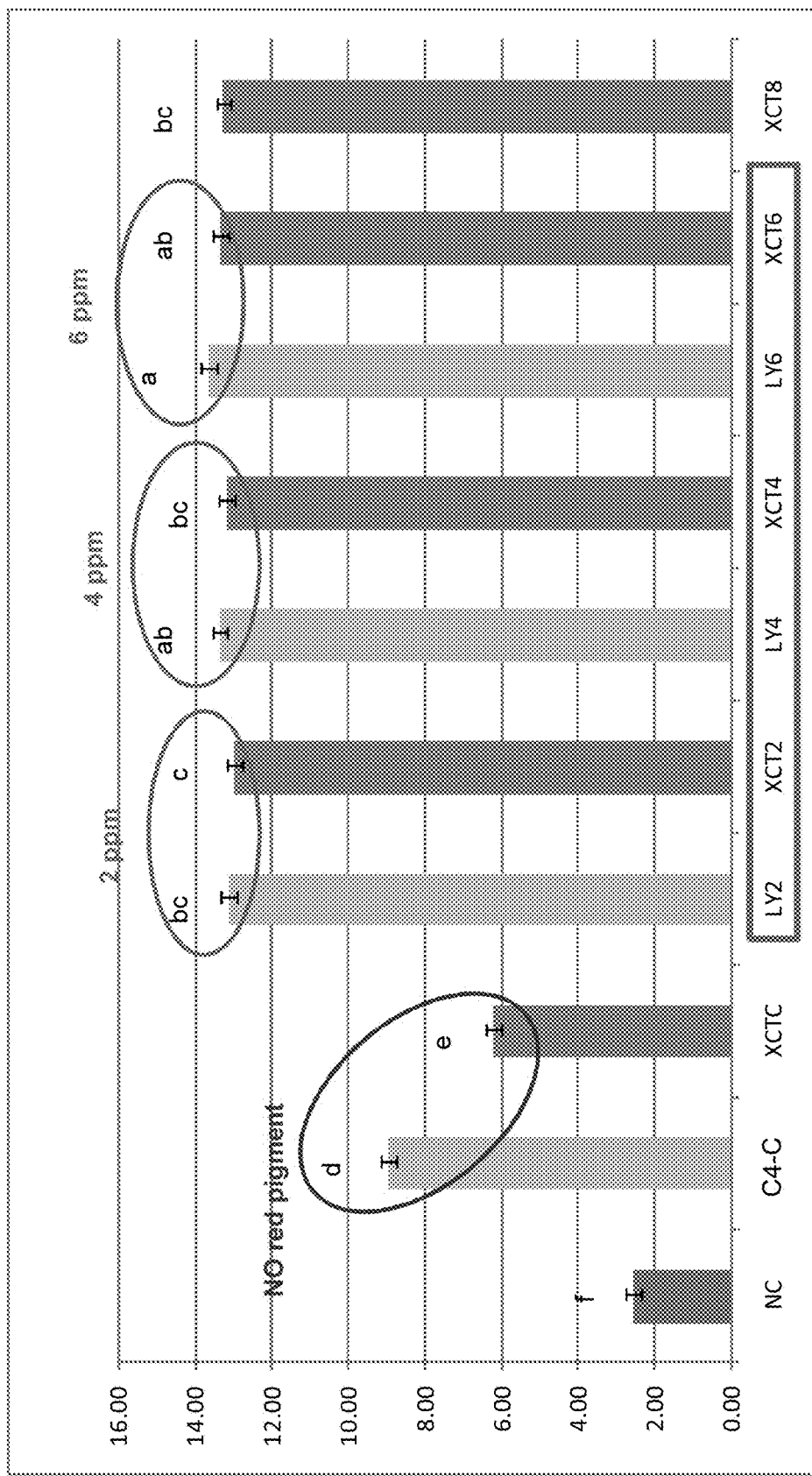
FIG. 13 shows DSM/Roche color fan results when synthetic red dye is added.

Color Fan analysis was conducted with DSM Yolk Color Fan (also known as Roche Color Fan). The analysis has 15 scales of color index used to distinguish yolk color density. The method consists of assessing yolk as a visual comparison and estimation of carotenoids. Result of the yolk color fan show that when red pigment is added, the CXT is comparable to multiple competitors. FIG. 13 shows the result of color fan analysis with red pigment and without red pigment. The differences are not detectable to consumers.

Example 22: Layer Trial with Natural Red Pigment Added

A trial was performed with laying hens in cages to compare the pigmenting efficiency of 2 yellow pigments (A and B) when red pigment from natural origin (C) was added on egg yolk color of layers.

The trial lasted 7 weeks, including 3 weeks of xanthophylls depletion feeding the "white" basal diet, followed by 4 weeks of feeding the experimental diets.

Animals: 240 commercial brown laying hens were used (Hy-line Brown) at 38 wks old at the beginning of the trial.

Feed and water were provided for ad libitum consumption. The basal diets were formulated according to Hy-line Brown recommendation (Hy-Line International Red Book, 2009). A single basal diet was formulated according to the expected feed consumption. Each feeding treatment was prepared from the addition of the corresponding amount of product.

There were a total of 10 feeding treatments (24 replicates of 1 hen/cage per treatment).

Performance variables were checked and recorded per replicate every second week while feeding the experimental feeds (body weight, feed consumption, laying rate, egg weigh, incidence of broken, soft shelled or dirty eggs on a daily basis). Egg yolk color was assessed at the end of the xanthophylls depletion phase (0 d), weekly for three weeks (7 d, 14 d, 21 d) and more frequently during the 4th week (25 d to 28 d). All eggs laid on each single day were taken for egg yolk color assessment.

Performance variables were checked and recorded per replicate every second week while feeding the experimental feeds (body weight, feed consumption, laying rate, egg weigh, incidence of broken, soft shelled or dirty eggs on a daily basis). Egg yolk color was assessed at the end of the xanthophylls depletion phase (0 d), weekly for three weeks (7 d, 14 d, 21 d) and more frequently during the 4th week (25 d to 28 d). All eggs laid on each single day were taken for egg yolk color assessment.

Figure 14:
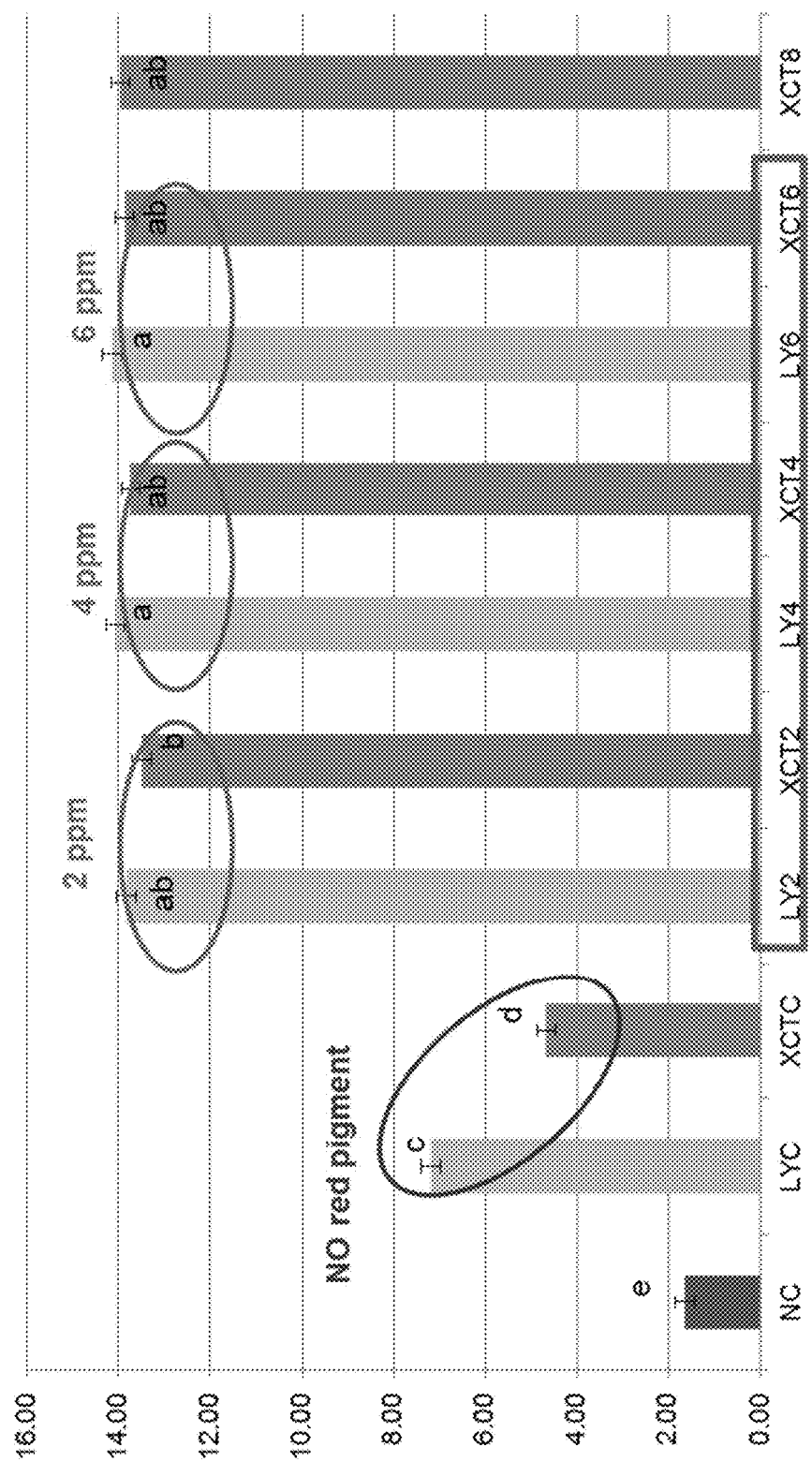
FIG. 14 shows DSM/Roche color fan results when natura red dye is added.

Color Fan analysis was conducted with DSM/Roche Yolk Color Fan (also known as Roche Color Fan). The analysis has 15 scales of color index used to distinguish yolk color density. The method consists of assessing yolk as a visual comparison and estimation of carotenoids. Result of the yolk color fan show that when red pigment is added, the CXT is comparable to multiple competitors. FIG. 14 shows the result of color fan analysis with red pigment and without red pigment. The differences are not detectable to consumers.

Example 23: Spectroscopic Studies

Figure 15A:
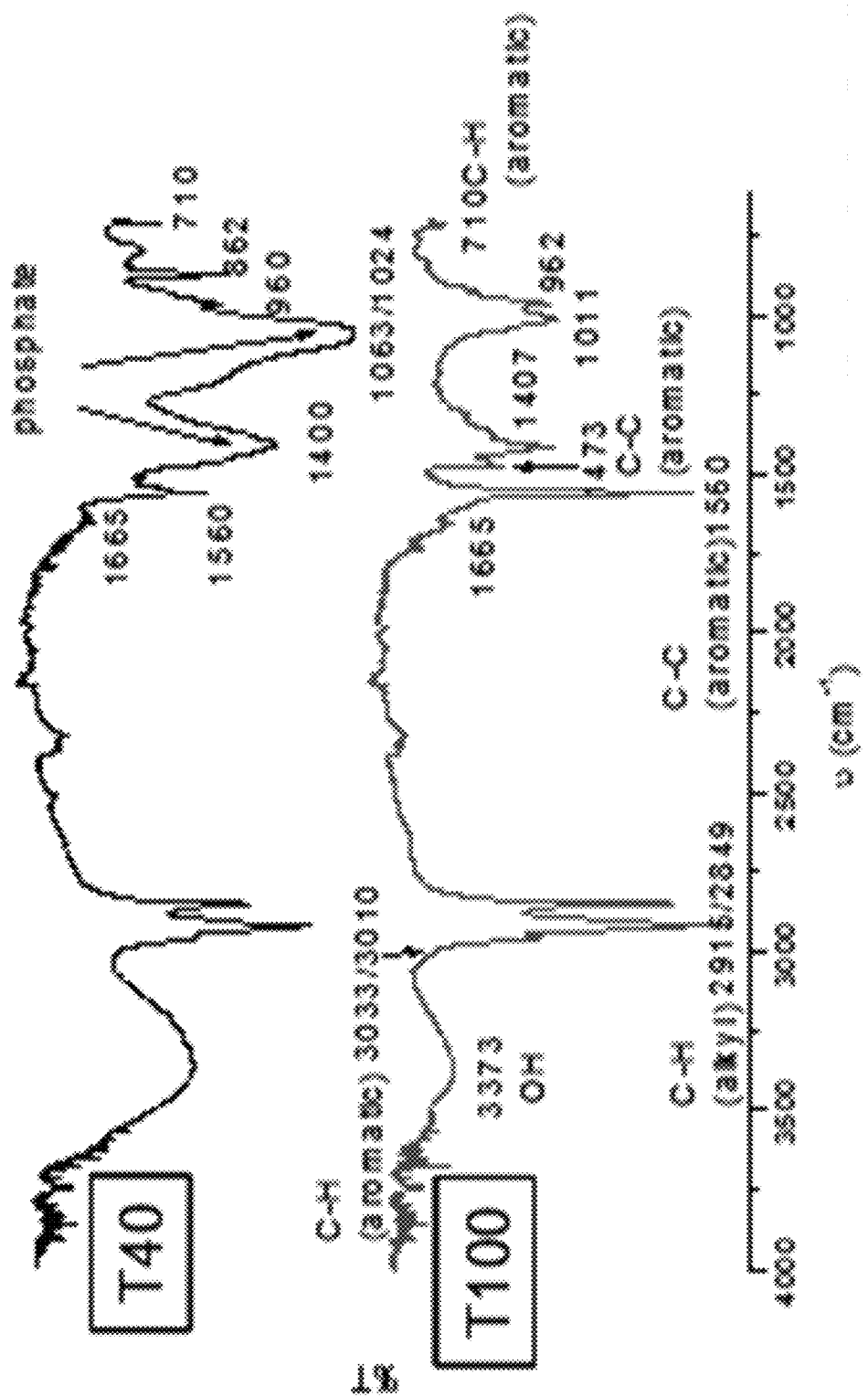
FIGS. 15A-C show the results of various spectroscopic studies.
Figure 15B:
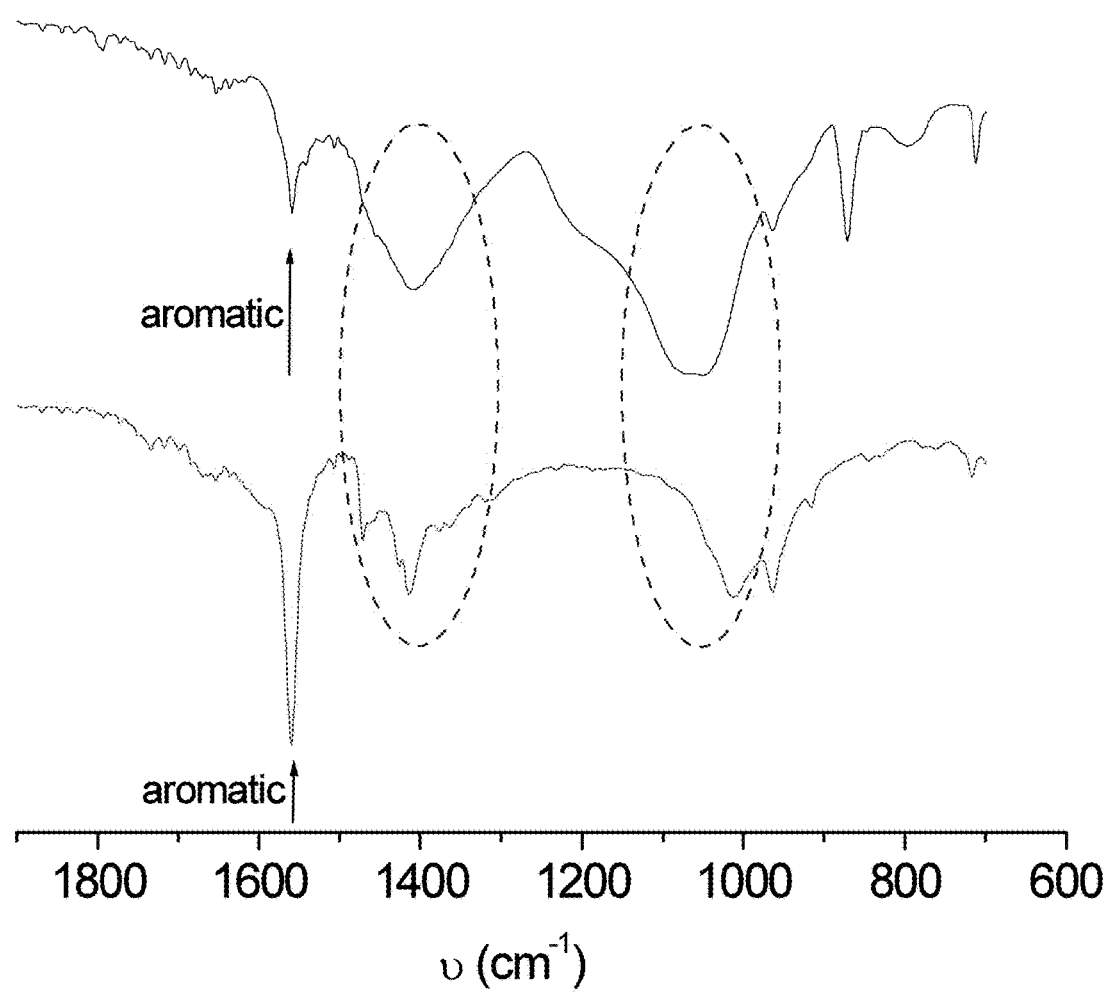

Spectroscopic studies were performed with X-40 and XCT. FIG. 15A shows a side by side of the FTIR spectra. X-40 and XCT have similar characteristics with bands corresponding to vibration modes of aromatic and aliphatic functional groups. The =C—H stretches (3033 and 3010 cm$^{-1}$), C—H out of the ring plane (710 cm$^{-1}$) and C—C stretches in the aromatic ring (1560, 1473 cm$^{-1}$) indicate the presence of unsaturated moieties in the structure. In addition the bands corresponding to —C—H stretches of the alkyl groups (2915/2849 cm$^{-1}$) are present in both samples indicating the existence of aliphatic groups. In the case of T40 FTIR spectrum, the intense bands at 1400, 1063 and 1024 cm$^{-1}$, corresponding to phosphate groups, are overlapped with some bands in the fingerprint region of molecule. FIG. 15B shows an expanded region from region from 1800 to 600 cm$^{-1}$ The bottom and top lines are the same as FIG. 15A.

Figure 15C:
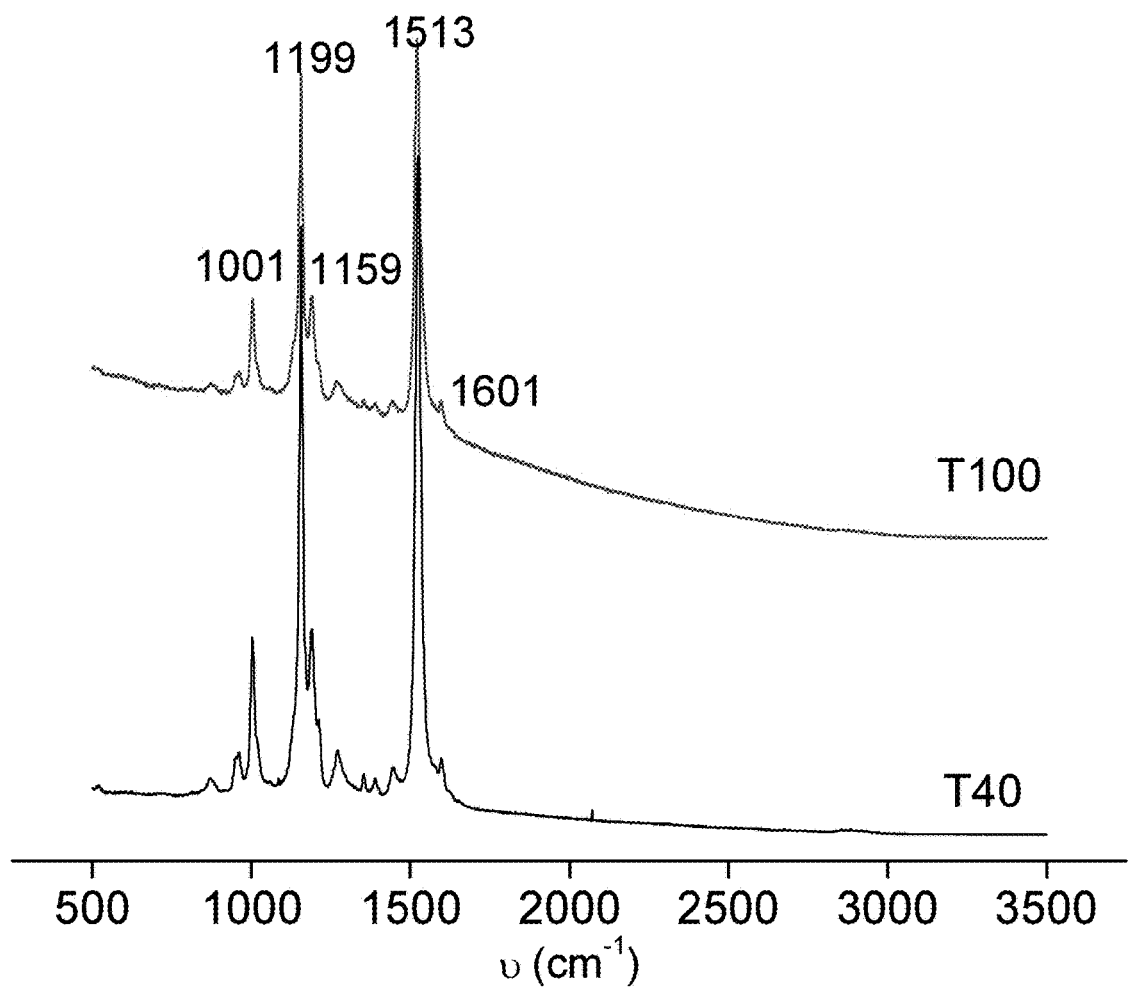

FIG. 15C shows the Raman spectra of X-40 (black) against XCT (red).

Example 24: Thin Layer Chromatography

Figure 16A:
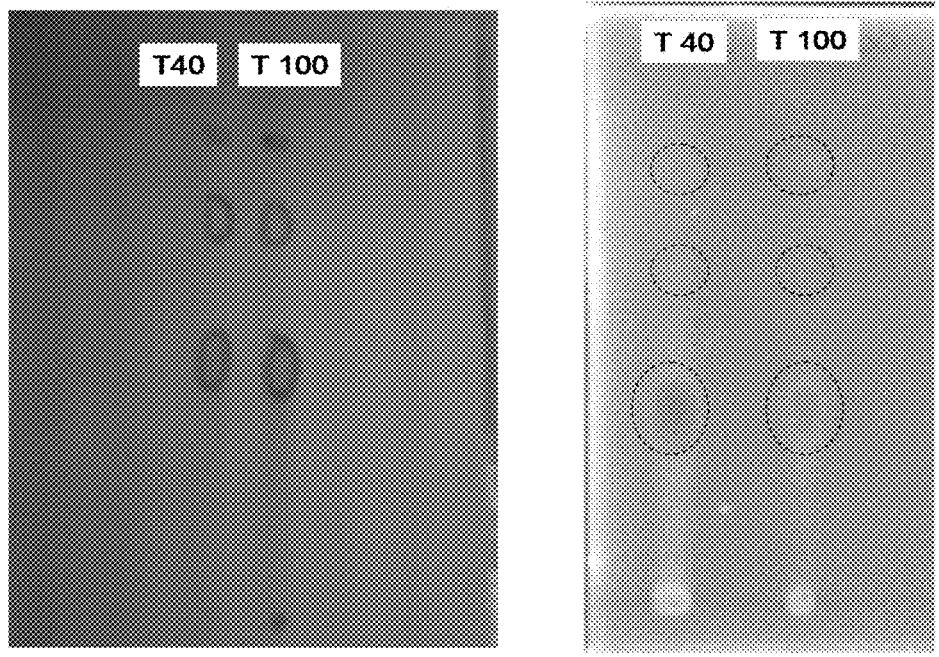
FIGS. 16A-C show the results of Thin Layer Chromatography (TLC) of X-40 and XCT.
Figure 16B:
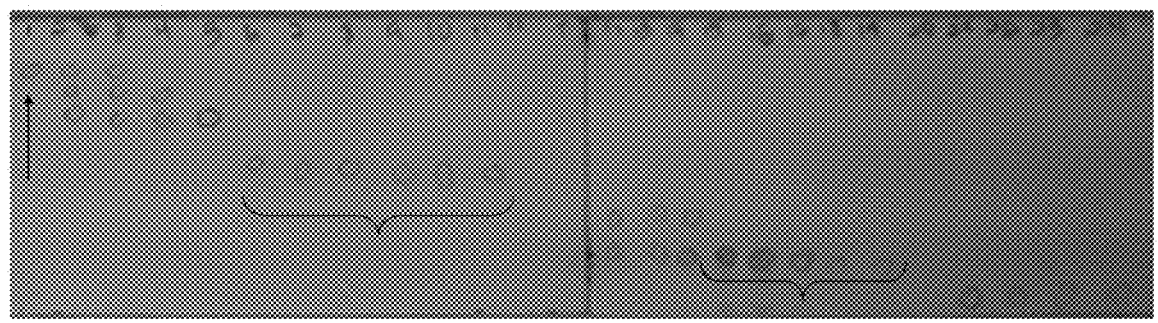

Samples of XCT and X-40 were dissolved in chloroform and centrifuged for discarding the white precipitate. Thin Layer Chromatography (TLC) was carried out in a mobile phase of hexane:ethyl acetate (1:1 v/v). TLC plates were developed by irradiating with UV and visualized using $I_2$ exposure. The initial TLC, shown in FIG. 16A showed three principal compounds. Silica gel chromatography columns were used to separate compounds from the mixture samples. The initial fractions were eluted using 2:1 hexane:ethyl acetate as a solvent (fractions 1-5). The polarity of the solvent mixture was then increased to ethyl acetate (fractions 6 to 14), and finally 20% methanol in ethyl acetate (fractions 15 to 19). FIG. 16B shows the results for X-40.

Figure 16C:
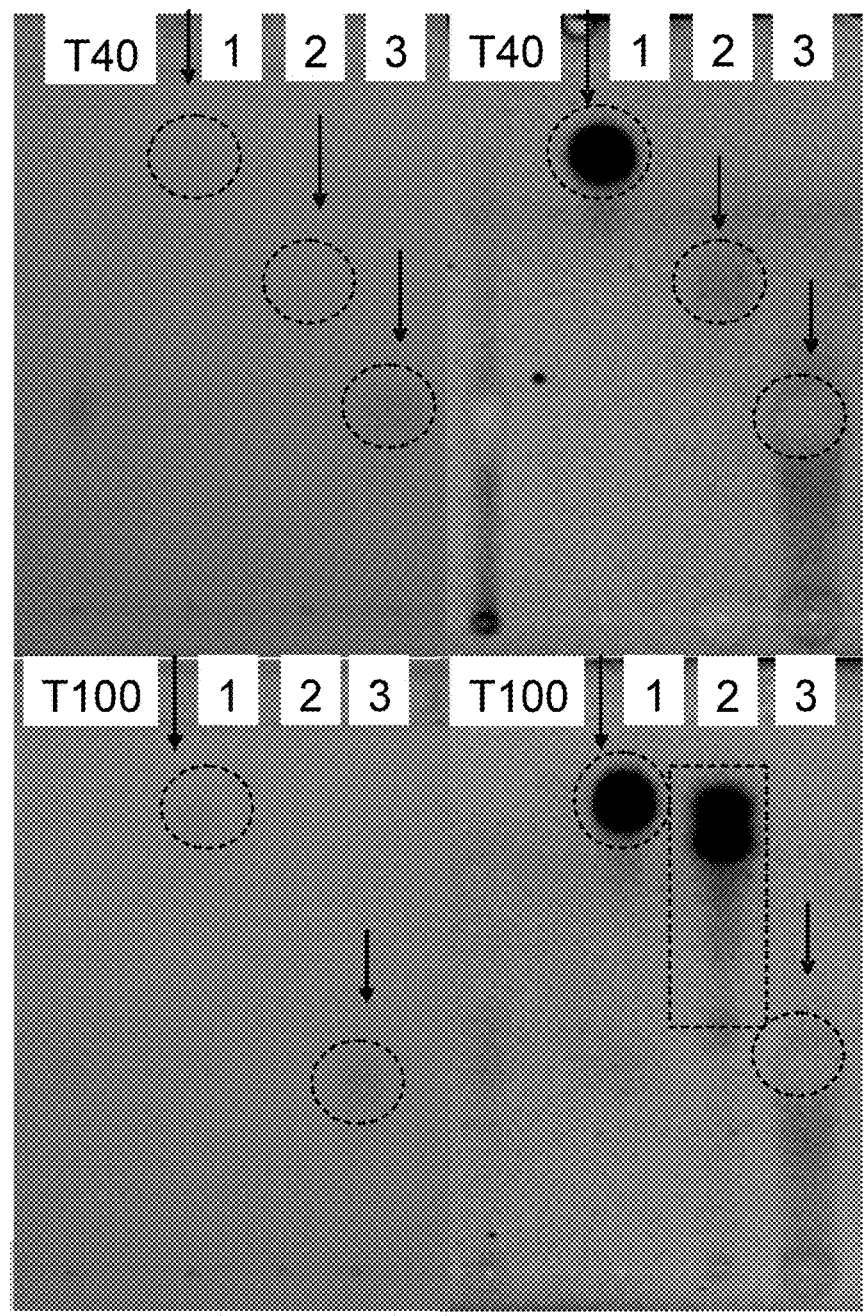

From the TLC is possible to conclude that the proportions of principal compounds are not the same for X-40 and XCT. The principal compound is number 3 for both samples, as also was corroborated for the amount isolated in pure form by column chromatography of X-40 and XCT. In the case of XCT compound 2 was not successfully purified from column, as is shown in FIG. 16C, while others are present in fraction 2. For XCT the amount of compound 2 is significantly less than in X-40. In addition, the amount of compound 3 purified from column was higher for XCT than for X-40.

What is claimed is:

1. A composition, the composition comprising soap derived from the saponification of a natural carotenoid-containing oleoresin, the soap comprising non-esterified xanthophyll particles and oleoresin components from the original natural carotenoid-containing oleoresin, wherein 90% of the non-esterified xanthophyll particles are less than 0.5 microns across the largest diameter and wherein the composition comprises at least 75 mg of non-esterified xanthophyll per gram of soap.

2. The composition of claim 1, wherein at least 95% of the non-esterified xanthophyll particles are less than 0.5 microns across the largest diameter.

3. The composition of claim 2, wherein at least 99% of the non-esterified xanthophyll particles are less than 0.5 microns across the largest diameter.

4. The composition of claim 1, wherein at least 60% of the non-esterified xanthophyll is the all-trans isomer.

5. The composition of claim 4, wherein at least 80% of the non-esterified xanthophyll is the all-trans isomer.

6. The composition of claim 1, wherein the composition comprises at least 100 mg of non-esterified xanthophyll per gram soap.

7. The composition of claim 1, wherein the composition further comprises less than about 15% of a free flow agent.

8. The composition of claim 1, wherein the natural carotenoid-containing oleoresin is marigold oleoresin.

9. The composition of claim 1, wherein the non-esterified xanthophyll particles comprise lutein.

10. The composition of claim 1, wherein the non-esterified xanthophyll particles comprise zeaxanthin.

11. The composition of claim 1, wherein the non-esterified xanthophyll particles comprise at least lutein and zeaxanthin.

12. The composition of claim 1, wherein the soap is derived from the saponification of a natural carotenoid-containing oil produced from the natural carotenoid-containing oleoresin.

13. The composition of claim 1, wherein the composition retains greater than 98% of the initial non-esterified total xanthophyll concentration when stored at room temperature in an oxygen permeable dark bag for one month.

14. The composition of claim 1, wherein the composition retains greater than 90% of the initial non-esterified total xanthophyll concentration when stored at room temperature, in an oxygen permeable dark bag, mixed with animal feed or animal feed ingredients, for one month.

15. An animal feed, the animal feed comprising the composition of claim 1.

16. A method of increasing the pigmenting efficacy of an animal feed, the method comprising combining the animal feed with a composition of claim 1.

17. The method of claim 16, wherein the animal feed is an egg laying fowl feed or aquaculture feed.

18. A method of increasing the carotenoid content of egg yolk, the method comprising administering a composition of claim 1 to egg laying fowl.

19. The method of claim 18, wherein the egg laying fowl are chickens or ducks.

20. A method of increasing the carotenoid content of skin in a subject, the method comprising administering a composition of claim 1 to the subject.

21. A method of increasing the carotenoid content of an animal feed, the method comprising combining a composition of claim 1 with the animal feed.

22. The method of claim 21, wherein the carotenoid is a xanthophyll.

23. The method of claim 21, wherein the xanthophyll is lutein.

* * * * *